US012257069B2

(12) United States Patent
Martinot

(10) Patent No.: US 12,257,069 B2
(45) Date of Patent: *Mar. 25, 2025

(54) SYSTEM COMPRISING A SENSING UNIT AND A DEVICE FOR PROCESSING DATA RELATING TO DISTURBANCES THAT MAY OCCUR DURING THE SLEEP OF A SUBJECT

(71) Applicant: Sunrise SA, Namur (BE)

(72) Inventor: Pierre Martinot, Namur (BE)

(73) Assignee: Sunrise SA, Namur (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/406,895

(22) Filed: Jan. 8, 2024

(65) Prior Publication Data

US 2024/0138759 A1 May 2, 2024

Related U.S. Application Data

(63) Continuation-in-part of application No. 17/664,942, filed on May 25, 2022, now Pat. No. 11,864,910, (Continued)

(30) Foreign Application Priority Data

Mar. 28, 2019 (BE) .................................. 2019/0028
Jul. 30, 2019 (EP) ..................................... 19189095

(51) Int. Cl.
*A61B 5/00* (2006.01)
*A61B 5/06* (2006.01)
*A61B 5/11* (2006.01)

(52) U.S. Cl.
CPC ............ *A61B 5/4818* (2013.01); *A61B 5/067* (2013.01); *A61B 5/1114* (2013.01);
(Continued)

(58) Field of Classification Search
CPC ... A61B 5/4818; A61B 5/1114; A61B 5/1121; A61B 5/4812; A61B 2562/0219
See application file for complete search history.

(56) References Cited

U.S. PATENT DOCUMENTS 3,801,758 A 4/1974 Shand et al.
6,107,922 A 8/2000 Bryuzgin
(Continued)

FOREIGN PATENT DOCUMENTS

CA 2163855 A1 6/1996
CN 1602970 A 4/2005
(Continued)

OTHER PUBLICATIONS

Abraham, et al., Phrenic Nerve Stimulation for the Treatment of Central Sleep Apnea, Jacc: Heart Failure, 3(5):360-369 (May 2015).
(Continued)

Primary Examiner — May A Abouelela
Assistant Examiner — Yasmeen S Warsi
(74) Attorney, Agent, or Firm — Greenberg Traurig, LLP; Christopher C. Bolten; Robert D. Ward

(57) ABSTRACT

The present invention relates to devices, systems and methods for detecting disturbances that may occur during the sleep of a subject using measurements and assessments of mandibular rotation and movement of a sleeping subject. A sensing unit may be positioned onto the exterior of the subject's mandible and may generate data measurements corresponding to mandibular rotation and movement. For example, measurements by an accelerometer and gyroscope corresponding to rotation and movement of the mandible provide the necessary information to arrive at an accurate assessment of sleep stages, sleep indicators and/or other sleep related information which may be used to make recommendations regarding sleep conditions and/or disor-
(Continued)

ders. A report may be generated including such sleep stages, sleep indicators and/or other sleep related information as well as any recommendations regarding sleep conditions and/or disorders for use for diagnosing sleep events such as obstructive sleep apnea (OSA).

30 Claims, 30 Drawing Sheets

Related U.S. Application Data which is a continuation of application No. 17/598,184, filed as application No. PCT/EP2020/058822 on Mar. 27, 2020.

(52) U.S. Cl.
CPC .......... *A61B 5/1121* (2013.01); *A61B 5/4557* (2013.01); *A61B 5/4812* (2013.01); *A61B 5/6814* (2013.01); *A61B 5/7264* (2013.01); *A61B 5/7267* (2013.01); *A61B 2562/0219* (2013.01); *A61B 2562/0223* (2013.01)

(56) References Cited

U.S. PATENT DOCUMENTS

| | | | |
|---|---|---|---|
| 7,680,538 B2 | 3/2010 | Durand et al. |
| 7,949,403 B2 | 5/2011 | Palermo et al. |
| 8,545,416 B1 | 10/2013 | Kayyali et al. |
| 8,548,770 B2 | 10/2013 | Yuen et al. |
| 9,014,819 B2 | 4/2015 | Lee et al. |
| 9,180,267 B2 | 11/2015 | Bowditch et al. |
| 9,415,216 B2 | 8/2016 | Mashiach |
| 9,504,828 B2 | 11/2016 | Mashiach et al. |
| 9,643,022 B2 | 5/2017 | Mashiach et al. |
| 9,750,977 B2 | 9/2017 | Yuen et al. |
| 10,029,098 B2 | 7/2018 | Papay |
| 10,092,219 B2 | 10/2018 | Arnold et al. |
| 10,311,745 B2 | 6/2019 | Arnold et al. |
| 10,354,135 B2 | 7/2019 | Herscovici-Cohen et al. |
| 10,381,109 B2 | 8/2019 | Hong et al. |
| 10,695,528 B2 | 6/2020 | Soulet et al. |
| 10,700,774 B2 | 6/2020 | Panther et al. |
| 10,755,814 B2 | 8/2020 | Bradley |
| 10,814,137 B2 | 10/2020 | Mashiach et al. |
| 11,033,738 B2 | 6/2021 | Steier |
| 11,191,970 B2 | 12/2021 | Mashiach et al. |
| 11,298,258 B2 | 4/2022 | Bedford |
| 11,752,327 B2 | 9/2023 | Martinot |
| 11,864,910 B2 | 1/2024 | Martinot |
| 11,992,671 B2 | 5/2024 | Martinot |
| 2007/0156182 A1 | 7/2007 | Castel et al. |
| 2007/0273366 A1 | 11/2007 | Ansay et al. |
| 2008/0033304 A1 | 2/2008 | Dalal et al. |
| 2009/0275031 A1 | 11/2009 | Tanner et al. |
| 2011/0230702 A1 | 9/2011 | Honour |
| 2011/0308528 A1 | 12/2011 | Ciardullo |
| 2013/0096843 A1 | 4/2013 | Yuen et al. |
| 2013/0226020 A1 | 8/2013 | Holley et al. |
| 2014/0278139 A1 | 9/2014 | Hong et al. |
| 2016/0022203 A1 | 1/2016 | Arnold et al. |
| 2016/0128624 A1 | 5/2016 | Matt |
| 2016/0296165 A1 | 10/2016 | Moore et al. |
| 2016/0325143 A1 | 11/2016 | Yuen et al. |
| 2017/0035350 A1 | 2/2017 | Allessie |
| 2017/0265801 A1 | 9/2017 | Patwa et al. |
| 2017/0347946 A1 | 12/2017 | Arnold et al. |
| 2018/0000563 A1 | 1/2018 | Shanjani et al. |
| 2018/0110960 A1 | 4/2018 | Youngblood et al. |
| 2018/0116863 A1 | 5/2018 | Shah et al. |
| 2018/0117317 A1 | 5/2018 | Oku et al. |
| 2018/0126107 A1 | 5/2018 | Valster et al. |
| 2018/0261324 A1 | 9/2018 | Bradley |
| 2018/0272118 A1 | 9/2018 | Goldwasser et al. |
| 2019/0021651 A1 | 1/2019 | Hanssen et al. |
| 2019/0142625 A1 | 5/2019 | Goff et al. |
| 2019/0229802 A1 | 7/2019 | Panther et al. |
| 2019/0247650 A1 | 8/2019 | Tran |
| 2020/0015737 A1 | 1/2020 | Van Pee et al. |
| 2020/0016401 A1 | 1/2020 | Papay et al. |
| 2020/0129762 A1 | 4/2020 | Toong et al. |
| 2020/0155840 A1 | 5/2020 | Giannoukos et al. |
| 2020/0155846 A1 | 5/2020 | Toong et al. |
| 2020/0163794 A1 | 5/2020 | Goff et al. |
| 2020/0353244 A1 | 11/2020 | Yamazaki |
| 2021/0162211 A1 | 6/2021 | Chase et al. |
| 2021/0260369 A1 | 8/2021 | Steier |
| 2023/0414940 A1 | 12/2023 | Martinot |

FOREIGN PATENT DOCUMENTS

| | | | |
|---|---|---|---|
| CN | 101566328 A | 10/2009 |
| CN | 103167828 A | 6/2013 |
| CN | 205493840 U | 8/2016 |
| CN | 106163391 A | 11/2016 |
| CN | 107205721 A | 9/2017 |
| CN | 107405486 A | 11/2017 |
| CN | 107440680 A | 12/2017 |
| CN | 107518952 A | 12/2017 |
| CN | 107614056 A | 1/2018 |
| CN | 108451503 A | 8/2018 |
| DE | 202013105962 U1 | 1/2014 |
| DE | 102016120583 B3 | 4/2018 |
| EP | 3253443 B1 | 11/2018 |
| EP | 3801758 A1 | 4/2021 |
| FR | 2655072 A1 | 5/1991 |
| JP | 2004187961 A | 7/2004 |
| JP | 2007502670 A | 2/2007 |
| JP | 2014158607 A | 9/2014 |
| JP | 2017533752 A | 11/2017 |
| KR | 20130134268 A | 12/2013 |
| KR | 20170083483 A | 7/2017 |
| RU | 2015154805 A | 6/2017 |
| RU | 2628064 C2 | 8/2017 |
| WO | WO-2009012298 A2 | 1/2009 |
| WO | WO-2020035852 A2 | 2/2020 |
| WO | WO-2020193778 A1 | 10/2020 |
| WO | WO-2020261226 A1 | 12/2020 |
| WO | WO-2022069748 A2 | 4/2022 |

OTHER PUBLICATIONS

Allen, et al., Using Electrical Stimulation, A Guideline for Allied Health Professionals, Jan. 2014.
Ayappa et al. "The upper airway in sleep: physiology of the pharynx," Sleep Medicine Review, 7(1):9-33 (2003).
Benjafield, et al., Estimation of the global prevalence and burden of obstructive sleep apnoea: a literature-based analysis, The lancet Respiratory Medicine, 7(8):687-98 (Aug. 2019).
Berquin et al. "Brainstem and hypothalamic areas involved in respiratory chemoreflexes: a Fos study in adult rats," Brain Research, 857:30-40 (2000).
Boon, et al., Upper Airway Stimulation for Obstructive Sleep Apnea: Results from the ADHERE Registry, Otolaryngology-Head and Neck Surgery, 159(2):379-385 (Aug. 2018).
CES 2021 Innovation Award product, Sunrise, accessed at https://www.ces.tech/innovation-awards/honorees/2021/honorees/s/sunrise.aspx.
Decker, et al., Functional electrical stimulation and respiration during sleep, J. Appl. Physiol., 75(3):1056-1061 (Sep. 1993).
Dotan, et al., Parameters affecting pharyngeal response to genioglossus stimulation in sleep apnoea, Eur. Respir. J., 38(2):338-347 (Aug. 2011).
Eastwood, et al., Bilateral hypoglossal nerve stimulation for treatment of adult obstructive sleep apnoea, Eur. Respir. J., 55(1):1901320 (Jan. 2020).
Eastwood, et al., Treating Obstructive Sleep Apnea with Hypoglossal Nerve Stimulation, Sleep, 34(11):1479-1486 (Nov. 2011).
Edmonds, et al., The Effects of Transcutaneous Electrical Stimulation During Wakefulness and Sleep in Patients with Obstructive Sleep Apnea, Am. Rev. Respir. Dis., 146(4):1030-1036 (Oct. 1992).

(56) References Cited

OTHER PUBLICATIONS

Europe's 100 hottest young scaleups of 2021, awarded by The Next Web (TNW), accessed at thenextweb.com (2021).
Extended EP Search Report dated Mar. 11, 2021 in EP Patent Application Serial No. 20199684.0 (0230).
French Ministry of Health-Sunrise-relating to coverage under Article L. 165-1 of the Social Security Code for the diagnosis of obstructive sleep apnea-hypopnea syndrome, Jun. 17, 2021, accessed at, https://www.legifrance.gouv.fr/jorf/id/JORFTEXT000043699634.
Friedman, et al., Targeted Hypoglossal Nerve Stimulation for the Treatment of Obstructive Sleep Apnea: Six-Month Results, The Laryngoscope, 126(11):2618-2623 (Nov. 2016).
Gestreau et al. "Differential Brainstem Fos-Like Immunoreactivity after Laryngeal-induced Coughing and Its Reduction by Codeine," The Journal of Neuroscience, 17(23):9340-9352 (Dec. 1997).
Giannasi, et al., Effects of Neuromuscular Electrical Stimulation on the Masticatory Muscles and Physiologic Sleep Variables in Adults with Cerebral Palsy: A Novel Therapeutic Approach, PloS one, 10(8):e0128959 (Aug. 2015).
Goding, et al., Hypoglassal nerve Stimulation and Airway Changes Under Fluoroscopy, Otolaryngology-Head and Neck Surgery, 146(6):117-1022 (Jun. 2012).
Guilleminault, et al., The Effect of Electrical Stimulation on Obstructive Sleep Apnea Syndrome, Chest, 107(1):67-73 (Jan. 1995).
Guo-Ping, et al., Mandibular distraction osteogenesis for improving respiratory function in patients with micrognathia complicated by obstructive sleep apnea syndrome, Chinese Journal of Clinical Rehabilitation, 9(6):195-198 (Feb. 2005).
Heiser, et al., Functional Outcome of tongue motions with selective hypoglossal nerve stimulation in patients with obstructive sleep apnea, Sleep and Breathing, 20(2):553-60 (May 2016).
Heiser, et al., Selective upper airway stimulation for obstructive sleep apnea: a single center clinical experience, Eur. Arch. Oto-Rhino-Laryngology, 274(3):1727-1734 (Mar. 2017).
Henke et al. "Load compensation and respiratory muscle function during sleep," J. Appl. Physiol., 72(4):1221-1234 (1992).
Hida, et al., Effects of submental stimulation for several consecutive nights in patients with obstructive sleep apnoea, Thorax, 49(5):446-452 (May 1994).
Hida, et al., The Effect of Submental Electrical Stimulation on Sleep Disordered Breathing in Patients with Obstructive Apnea, Sleep, 16:S96-S97 (Dec. 1993).
Hofauer, et al., Effects of upper-airway stimulation on sleep architecture in patients with obstructive sleep apnea, Sleep Breath, 21(4):901-908 (Dec. 2017).
Hofauer, et al., Patient experience with upper airway stimulation in the treatment of obstructive sleep apnea, Sleep and Breathing, 23(1);235-241 (Mar. 2019).
Hollowell et al. "Activation of masseter muscles with respiratory resistance loading," J. Appl. Physiol., 67(1):270-275 (1989).
Hollowell et al. "Mandible position and activation of submental and masseter muscle during sleep," J. Appl. Physiol., 71(6):2267-2273 (1991).
Hollowell et al. "Respiratory-related recruitment of the masseter: response to hypercapnia and loading," J. Appl. Physiol., 70(6):2508-2513 (1991).
Hu, et al., Percutaneous Biphasic Electrical Stimulation for Treatment of Obstructive Sleep Apnea Syndrome, IEEE Transactions on Biomedical Engineering, 55(1):181-187 (Jan. 2008).
International Search Report & Written Opinion dated Apr. 8, 2022 in Int'l PCT Patent Appl. Serial No. PCT/EP2021/077190 (0210).
International Search Report & Written Opinion dated Aug. 21, 2020 in Int'l PCT Patent Appl. Serial No. PCT/EP2020/058822 (0110).
Isono, et al., Effects of tongue electrical stimulation on pharyngeal mechanics in anaesthetized patients with obstructive sleep apnoea, Eur. Respir. J., 14(6):1258-1265 (1999).
Kelly et al. "Diagnosis of Sleep Apnoea Using a Mandibular Monitor and Machine Learning Analysis: One-Night Agreement Compared to in-Home Polysomnography," Frontiers in Neuroscience, 16:1-10 (Mar. 2022).
Kezirian, et al., Hypoglossal nerve stimulation improves obstructive sleep apnoea, J. Sleep Res., 23(1):77-83 (Feb. 2014).
Lewis, et al., Implantation of the Nyxoah Bilateral Hypoglossal Nerve Stimulator for Obstructive Sleep Apnea, Laryngoscope Investigative Otolaryngology, 46(6):703-707 (Dec. 2019).
Liang, et al., Distraction osteogenesis for treatment of temporomandibular joint ankylosis accompanying with mandibular micrognathia and obstructive sleep apnea syndrome, Journal Peking University (Health Sci), 34:112-116 (Dec. 2002).
Lin, et al., Development of the Miniaturized Wireless Inertial measurement Unit WB-4: Pilot Test for Mastication Analysis, IEEE/SICE International Symposium on System Integration, Sendai, Japan, pp. 420-425 (Dec. 2010).
Martinot et al. "Artificial Intelligence Analysis of Mandibular Movements Enables Accurate Detection of Phasic Sleep Bruxism in OSA Patients: A Pilot Study," Nature and Science of Sleep, vol. 13., 1449-1459 (Aug. 2021).
Martinot et al. "Bruxism Relived under CPAP Treatment in a Patient With OSA Syndrome," Chest, 157(3):e59-e62 (2020).
Martinot et al. "Clinical validation of a mandibular movement signal based system for the diagnosis of pediatric sleep apnea," Pediatric Pulmonology, pp. 1-10 (Feb. 2021).
Martinot et al. "Mandibular Movements As Accurate Reporters of Respiratory Effort during Sleep: Validation against Diaphragmatic Electromyography," Frontiers in Neurology, 8(353):1-8 (Jul. 2017).
Martinot et al. "Mandibular Movements Identify Respiratory Effort in Pediatric Obstructive Sleep Apnea," J. Clin Sleep Med. 11(5):567-574 (2015).
Martinot et al. "Mandibular position and movements: Suitability for diagnosis of sleep apnoea," Respirology, pp. 1-8 (Aug. 2016).
Martinot et al. "Monitoring mandibular movements to detect Cheyne-Stokes Breathing," Respiratory Research 18:66 pp. 1-9 (2017).
Martinot et al. "Persistent Respiratory Effort After Adenotonsillectomy in Children with Sleep-Disordered Breathing," Sleep Respiratory—Laryngoscope, pp. 1-8 (2017).
Martinot et al. "The key role of the mandible in modulating airflow amplitude during sleep," Respiratory Physiology & Neurobiology, 279:103447 pp. 1-6 (May 2020).
Maurer, et al., Operative technique of upper airway stimulation: an implantable treatment of obstructive sleep apnea, Operative Techniques in Otolaryngology-Head and Neck Surgery, 23(3):227-233 (Sep. 2012).
Medical Advisory Secretariat, Oral Appliances For Obstructive Sleep Apnea: An Evidence-Based Analysis, *Ontario Health Technology Assessment Series*, 9(5):1-51 (Sep. 2009).
Merrill et al. "Origin of the Expiratory Inhibition of Nucleus Tractus Solitarius Inspiratory Neurones," Brain Research, 263:43-50 (1983).
Miki, et al., Effects of Electrical Stimulation of the Genioglossus on Upper Airway Resistance in Anesthetized Dogs, Am. Rev. Respir. Dis., 140(5):1279-84 (1989).
Miki, et al., Effects of Submental Electrical Stimulation During Sleep on Upper Airway Patency in Patients with Obstructive Sleep Apnea, Am. Rev. Respir. Dis., 140(5):1285-1290 (1989).
Moore et al. "How the brainstem controls orofacial behaviors comprised of rhythmic action," Trends in Neuroscience—Cell Press, pp. 1-11 (2014).
National Sleep Foundation's 2022 SleepTech Award, AYO and Sunrise Win National Sleep Foundation's 2022 SleepTech Award, accessed at https://www/thensf.org/avo-and-sunrise-win-national-sleep-foundations-2022-sleeptech-award.
Oliven, et al., Improved Upper Airway Patency Elicited by Electrical Stimulation of The Hypoglossus Nerves, Respiration, 63(4):213-216 (1996).
Oliven, et al., Sublingual electrical stimulation of the tongue during wakefulness and sleep, Respiration Physiology, 127(2-3):217-226 (Sep. 2001).
Oliven, et al., Upper airway response to electrical stimulation of the genioglossus in obstructive sleep apnea, J. Appl. Physiol, 95(5):2023-2029 (Nov. 2003).
Peek et al. "Machine Learning-based Sleep Staging in Patients with Sleep Apnea Using a Single Mandibular Movement Signal," Am. Journal of Respiratory and Critical Care Medicine, vol. 204:10, 1227-1230 (Nov. 2021).

(56) References Cited

OTHER PUBLICATIONS

Pepin et al. "Assessment of Mandibular Movement Monitoring With Machine Learning Analysis for the Diagnosis of obstructive Sleep Apnea," JAMA network Open, pp. 1-12 (Jan. 2020).
Polese, et al., Portable monitoring devices in the diagnosis of obstructive sleep apnea: current status, advantages, and limitations, J. Bras. Pneumol., 36(4):498-505 (2010).
Schwartz, et al., Electrical Stimulation of the Lingual Musculature in Obstructive Sleep Apnea, J. Appl. Physiol, 81(2):643-652 (Aug. 1996).
Schwartz, et al., Therapeutic Electrical Stimulation of the Hypoglossal Nerve in Obstructive Sleep Apnea, Arch. Otolaryngol. Head Neck Surg., 127(10):1216-1223 (Oct. 2001).
SLEEP 2022, "Sunrise unveils ground-breaking home sleep apnea test at SLEEP 2022," accessed at https://www.prnewswire.com/news-releases/sunrise-unveils-ground-breaking-home-sleep-apnea-test-at-sleep-2022-301543710.html.
Sunrise FDA 510(k) Approval on Device for Sleep Apnea Testing Based on Mandibular Movement (Dec. 22, 2022), available at https://www.accessdatta.fda.gov/cdrh_docs/pdf22/K222262.pdf.
Tamura et al. "Mandibular Advancement Improves the Laryngeal View during Direct Laryngoscopy Performed by Inexperienced Physicians," Anesthesiology, 100(3):598-601 (Mar. 2004).
The Big Squeeze Awards, "Disruptive Innovation of the Year," awarded by Startups.be & Scale-Ups.eu, accessed at https://www.startups.be/the-big-squeeze (2021).
Sunrise Receives FDA Clearance for Its At-home Sleep Apnea Test, BusinessWire, Feb. 1, 2023, accessed at https://www.businesswire.com/news/home/20230213005361/rn/Sunrise-Receives-FDA-Clearance-for-Its-At-home-Sleep-Apnea-Test.
Woodson, et al., Randomized Controlled Withdrawal Study of Upper Airway Stimulation on OSA: Short- and Long-term Effect, Otolaryngology-Head and Neck Surgery, 151(5):880-887 (Nov. 2014).

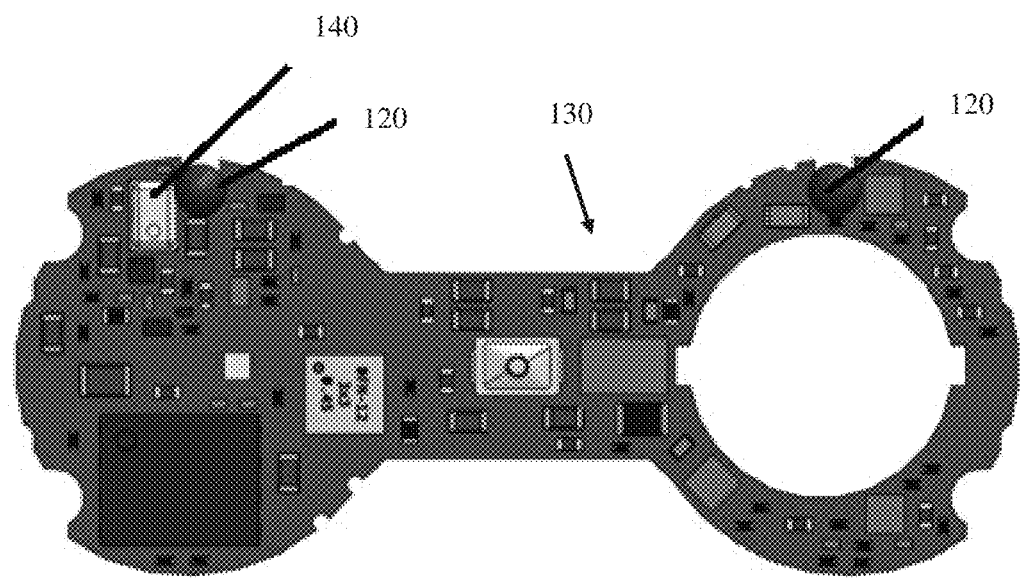
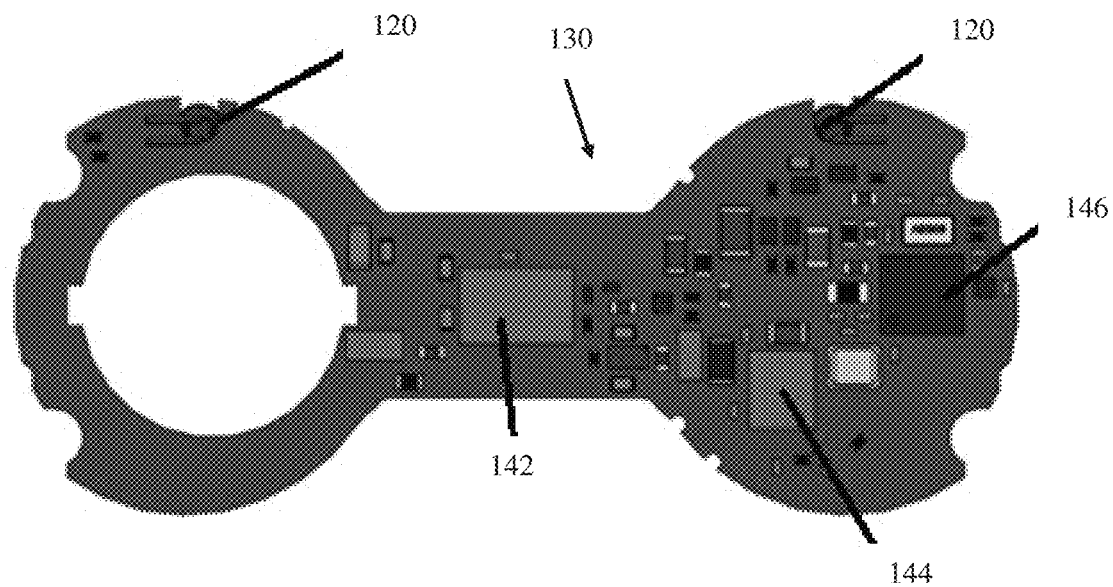
Fig. 1C

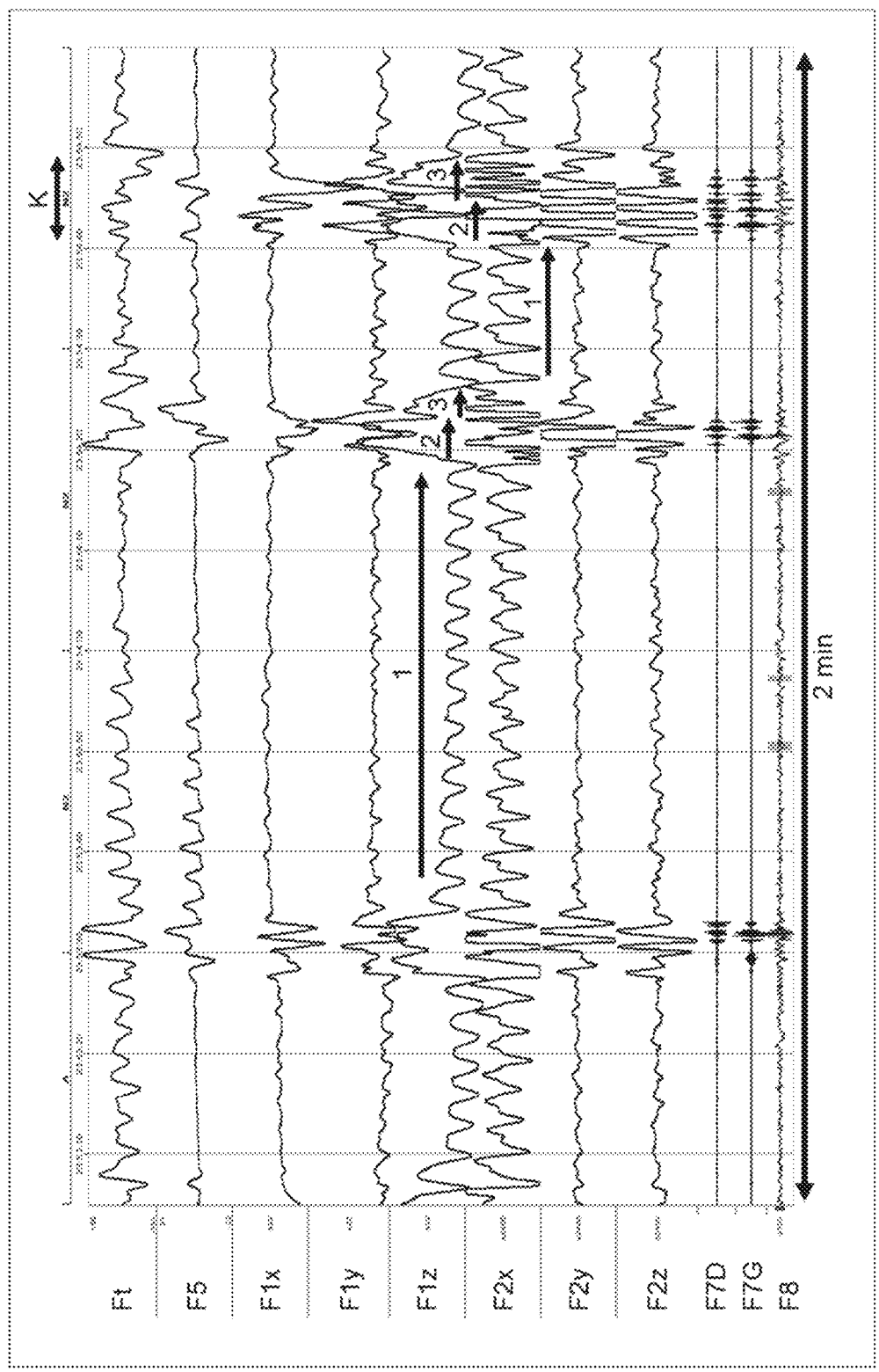

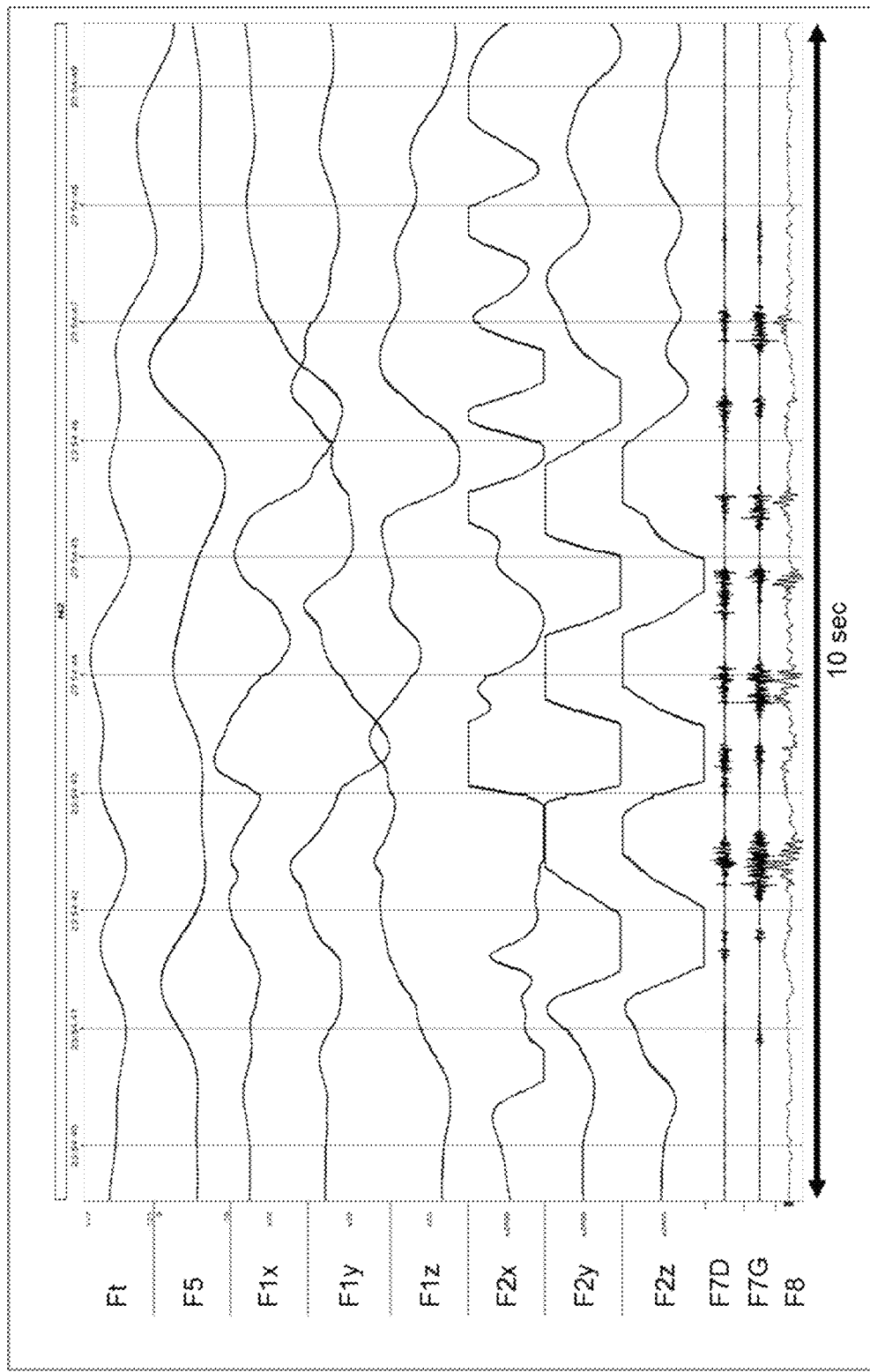

sun✶rise

Sleep Study Report of Doe John

Summary

AHI             17.9

0      Non-OSA     5     Mild     15     Moderate     30     Severe

Patient Information

| | | | |
|---|---|---|---|
| ID | 0001 | Sex | Male |
| Last Name | Doe | Height | 5 ft 7 in |
| First Name | John | Weight | 165 lbs |
| Date of Birth | 01/03/1985 | BMI | 26.0 |
| Age | 37 yrs | Neck Circ. | 14 in |
| Email | john.doe@example.com | | |
| Phone Number | +32 123 45 67 89 | | |

| | |
|---|---|
| Smoking | Former smoker |
| High Blood Pressure | No |
| Complaints | I snore – I often wake up during the night – I feel unusually tired during the day |
| ESS | 12 - Mild |
| ISI | 9 - Mild |

Referring Physician Information

| | |
|---|---|
| Last Name | Doe |
| First Name | John |
| Email | john.doe@example.com |
| Phone Number | +32 123 45 67 89 |

Patient Comments

| | |
|---|---|
| Alcohol Before Study? | No |
| Stimulants or Sedatives Before Study? | No |
| Medical Treatment Impacting Sleep? | No |
| Additional Comment | -- |

Recording Information

| | |
|---|---|
| Study Date (end) | 12/30/2022 |
| Start Time | 12:27 am |
| End Time | 6:54 am |
| Total Recording Time | 6 hrs, 27 min |
| Rejected Recording | 2% |
| Analysis Duration | 6 hrs, 20 min |
| Reliability | Reliable |

Sleep/Wake States

| | |
|---|---|
| TST | 5 hrs, 53 min |
| Sleep Start | 12:46 am |
| Sleep End | 6:52 am |
| Wake | 8% |
| SE | 92% |
| WASO | 14 min |
| Sleep Latency | 18 min |
| REM Latency | 48 min |

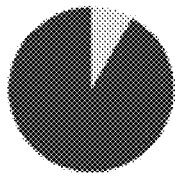

Sleep Stages (% of TST)

| | |
|---|---|
| REM | 21% |
| Light NREM | 62% |
| Deep NREM | 17% |

Fig. 22A sun✳rise                                              Sleep Study Report of Doe John

Respiratory Events

|  |  | Supine | Non-Sup. | REM | NREM |
|---|---|---|---|---|---|
| AHI | 17.9 | 21.9 | 13.4 | 23.5 | 16.4 |
| RDI | 24.2 | | | | |
| OAHI | 17.4 | | | | |
| CAHI | 0.5 | | | | |
| ORDI | 23.7 | 22.0 | 18.9 | 22.7 | 23.9 |

Above indices are calculated with hypopnea rule 1A.

| RERA Index | 6.3 |
| Respiratory Effort | 66% of TST |
| AHI (with hypopnea rule 1B) | 3.2 |

Awakenings and Arousals Events

| Awakening Index | 1.2 |
| ArI | 23.2 |

Oxygen Saturation

| ODI 3% | 3.0 |
| ODI 4% | 1.1 |
| Mean | 94% |
| Min | 90% |
| Max | 100% |
| Sleep Time < 90% | 0% of TST |
|  | 0 min |
| Sleep Time < 88% | 0% of TST |
|  | 0 min |

Pulse Rate (bpm)

| Mean | 69 |
| Min | 55 |
| Max | 91 |

Position

| Position Changes Index | 2.2 |
| Supine | 53% of TST |
| Non-Supine | 47% of TST |

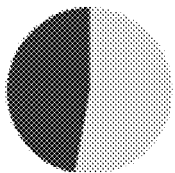

Interpretation

Impressions

Moderate OSA with an AHI of 17.9, a supine AHI of 21.9 and a REM AHI of 23.5 per sleep hour.
66% of sleep time spent with increased respiratory effort.

Recommendations

Consider a trial of Continuous Positive Airway Pressure (CPAP). Would recommend an auto titrating device with a range of pressure between 6 and 12 cm H2O, and with heated humidification. Nasal mask to fit. Follow up with referring physician. Download CPAP data in a short term to check for efficacy and compliance. Consider a Mandibular Advancement Device (MAD) if CPAP is unsuccessful. Follow-up home sleep apnea test (HSAT) at the end of the titration phase should be conducted to ensure objectively that the MAD controls both snoring and sleep apnea in all sleep positions and sleep stages.
This patient should avoid alcohol or sedating medications before bed.

Fig. 22B

SYSTEM COMPRISING A SENSING UNIT AND A DEVICE FOR PROCESSING DATA RELATING TO DISTURBANCES THAT MAY OCCUR DURING THE SLEEP OF A SUBJECT

CROSS REFERENCE TO RELATED APPLICATIONS

This application is a continuation-in-part of U.S. patent application Ser. No. 17/664,942, filed May 25, 2022, now U.S. Pat. No. 11,864,910, which is a continuation of U.S. patent application Ser. No. 17/598,184, filed Sep. 24, 2021, which is a U.S. National Phase under 35 U.S.C. § 371 of International Patent Application Serial No. PCT/EP2020/058822, filed Mar. 27, 2020, which claims the benefit of European Patent Application Serial No. 19189095.3, filed Jul. 30, 2019, and Belgian Patent Application Serial No. 2019/0028, filed Mar. 28, 2019, the entire contents of each of which are incorporated herein by reference.

FIELD OF THE INVENTION

The present invention relates to devices, systems and methods for detecting disturbances that may occur during the sleep of a subject.

BACKGROUND

The most common methodology issued for the assessment of sleep disorders and more specifically sleep disordered breathing is the in-lab polysomnography (PSG). This testing requires an overnight stay in a dedicated facility supervised by trained technicians. However, this method is expensive, time-consuming and is unable to keep pace with demand. Multiple physiological signals are recorded during PSG testing by different types of sensor (e.g. EEG, EMG, ECG, thermistor, pressure, video). Data from these sensors are later reviewed by a health care professional.

Alternative systems are considered in the art, US 2017/0265801 relates to a bruxism detection system for detection of teeth grinding and tapping. This system includes a chin mounted accelerometer that senses and records acceleration changes at the beginning and the end of jaw clenching. Data from the accelerometer is processed to distinguish bruxism related motion from other movements of the head by comparison to accelerometer threshold values.

US 2017/0035350 also relates to a bruxism detection system. This system includes two masseter mounted accelerometer, the first accelerometer being attached to the skin of the left masseter muscle and the second being attached to the skin of the right masseter muscle. Bruxism is detected when the recorded data of the two accelerometers is substantially equal.

US 2007/273366 relates to a sleep disorder detector system. This system includes a device for measuring distances by detection of emitted magnetic fields. The device can be mounted on a support arranged to be applied onto the head so as to measure movements of the mouth. Data from the device is processed to detect sleep respiratory disorders such as snoring.

A problem with the known systems is that the movement of the head of a subject wearing the sensing unit and that of their mandible are considered separately from one another. The same applies to the positions of the head and of the mandible, which are calculated from the accelerometer measured movements. However, data from an accelerometer is limiting and can be affected by movements of other body parts, such as the chest or trachea during breathing. Thus, the link between these various movements and positions is not taken sufficiently into consideration to analyse sleep disturbances, which can have a negative impact on a diagnosis to be based on the measured data streams.

In fact, a mandibular movement may be induced by either respiratory or non-respiratory movements. Thus, a movement of the head when the human being is sleeping may cause a movement of their mandible. The mandible may be considered as both a mechanical linkage with the tracheal tug or an effector of the brain control. Thus, mandibular movement may be passively induced by the breathing movements of the tracheal tug, or directly controlled by the brain. The tug is the traction exerted by the thorax on the head of the human being. This traction is at the respiratory frequency of that human being, because the thorax is moved with respiration because the respiratory muscles are controlled by the brain. Thus, if the head moves at the respiratory frequency, the mandible, which is attached to the head, will follow the movement imposed by the head, at the respiratory frequency. This is a passive movement that follows that of the head. The mandibular movement may equally be controlled directly and actively by the brain, even when the head may not move, or most often does not move. The brain controls the mandibular movements by stimulating a group of jaw muscles. It is therefore useful to be able to make a distinction between a mandibular movement controlled by the brain or by the attachment with tracheal tug. There is a need for a system that can more accurately interpret signals from the brain and more accurately identify sleeping disorders.

SUMMARY OF THE INVENTION

An object of the invention is to provide a system of a sensing unit and of a data processing device for associating in time the measurements of the movements and positions of the head and of the mandible of a subject during the analysis of the measured data.

In particular, the present invention concerns a system (equivalently, a combination) comprising a sensing unit and a processing unit for processing data relating to disturbances that may occur during the sleep of a subject, which sensing unit includes gyroscope adapted to measure movements of the mandible of a subject. The inventors have surprisingly found that the use of a gyroscope allows to capture mandibular spin and therefore to assess the activity of the brainstem which controls the mandibular motion during sleep.

In some embodiments, the present invention concerns a system comprising a sensing unit and a device for processing data, e.g. processing unit, relating to disturbances that may occur during sleep of a subject, which sensing unit includes an accelerometer adapted to measure movements of the head and/or of the mandible of a subject and a gyroscope adapted to measure movements of the mandible of that subject. The sensing unit is adapted to produce measurement signals based on the measurements effected and the processing unit includes first and second inputs for receiving a first, respectively a second, time stream of measurement signals coming from the accelerometer, respectively the gyroscope.

Thus provided herein is a system for characterizing sleep disorders in a subject having a head and a mandible comprising a gyroscope, a data analysis unit which are connected by a data link. In particular embodiments, the system is characterized in that it comprises:

a gyroscope configured for measuring rotational movements of the mandible of the subject;

a data analysis unit and a data link, the data link being configured for sending measured rotational movement data from the gyroscope to the data analysis unit;

wherein the data analysis unit comprises a memory unit which is configured for storing N mandible movement classes, wherein N is an integer larger than one, and wherein at least one of the N mandible movement classes is indicative of a sleep disorder event;

wherein each $j^{th}$ ($1 \leq j \leq N$) mandible movement class comprises of a $j^{th}$ set of rotational values, each $j^{th}$ set of rotational values being indicative of at least one rate, rate change, frequency, and/or amplitude of mandibular rotations associated with the $j^{th}$ class;

wherein the data analysis unit comprises a sampling element configured for sampling the measured rotational movement data during a sampling period, thereby obtaining sampled rotational movement data;

wherein the data analysis unit is configured to derive a plurality of measured rotational values from the sampled rotational movement data; and, wherein the data analysis unit is further configured for matching the measured rotational values with the N mandible movement classes.

In some embodiments, the system comprises an accelerometer that is adapted to measure accelerations, the accelerations being indicative of movements and/or positions of the head and/or mandible of the subject, the data link further being configured for sending measured acceleration data from the accelerometer to the data analysis unit;

wherein each $j^{th}$ ($1 \leq j \leq N$) mandible movement class comprises of a $j^{th}$ set of acceleration values, each $j^{th}$ set of acceleration values being indicative of at least one mandibular movement or head movement associated with the $j^{th}$ class;

wherein the sampling element is configured for sampling the measured acceleration data during a sampling period, thereby obtaining sampled acceleration data;

wherein the data analysis unit is configured to derive a plurality of measured acceleration values from the sampled acceleration data; and, wherein the data analysis unit is further configured for matching the measured acceleration values with the N mandible movement classes.

In some embodiments, the system further comprises a magnetometer, the magnetometer being adapted to measure magnetic field data, variations in magnetic field data being indicative of movements of the head and/or of the mandible of said subject, the data link further being configured for sending measured magnetic field data from the accelerometer to the data analysis unit;

wherein each $j^{th}$ ($1 \leq j \leq N$) mandible movement class comprises a $j^{th}$ set of magnetic field data values, each $j^{th}$ set of magnetic field data values being indicative of at least one rate or rate change of mandibular movement or head movement associated with the $j^{th}$ class;

wherein the data analysis unit comprises a sampling element configured for sampling the measured magnetic field data during a sampling period, thereby obtaining sampled magnetic field data;

wherein the data analysis unit is configured to derive a plurality of measured magnetic field values from the sampled magnetic field data; and, wherein the data analysis unit is further configured for matching the measured magnetic field values with the N mandible movement classes.

In some embodiments, the gyroscope, and optionally the accelerometer and/or the magnetometer or a part thereof are comprised in a sensing unit, the sensing unit being mountable on the mandible of the subject.

In some embodiments, one or more of the N mandible movement classes are characterized by a predetermined frequency range.

In some embodiments, the analysis unit is configured for identifying a movement of the head of the subject based on the gyroscope data, on the accelerometer data, and/or the magnetometer data.

In some embodiments, at least one of the N mandible movement classes is indicative of the subject being awake, and a plurality of the N mandible movement classes is indicative of the subject being asleep.

In some embodiments, at least one of the N mandible movement classes is indicative of the subject being in an N1 sleeping state; and wherein at least one of the N mandible movement classes is indicative of the subject being in a REM sleeping state; optionally wherein at least one of the N mandible movement classes is indicative of the subject being in an N2 sleeping state and/or wherein at least one of the N mandible movement classes is indicative of the subject being in an N3 sleeping state.

In some embodiments, one or more of the N mandible movement classes are indicative of an obstructive apnoea, an obstructive hypopnoea, a respiratory effort linked to arousal, a central apnoea, and/or a central hypopnoea.

In some embodiments, one of the N mandible movement classes is indicative of bruxism, and wherein the measured rotational movement data is indicative of a mandibular movement amplitude of at least 1 mm, at a frequency established in a range of 0.5 to 5 Hz during at least three respiratory cycles when the movement is phasic, or beyond 1 mm in a sustained, tonic manner for at least 2 seconds.

Further provided is a method for assisting in the characterization of sleep disorders in a subject having a mandible, comprising the steps:

receiving, by a data analysis unit and via a data link, rotational movement data from a gyroscope positioned on the mandible of the subject;

storing, by means of a memory unit comprised in the data analysis unit, N mandible movement classes, wherein N is an integer larger than one, and wherein at least one of the N mandible movement classes is indicative of a sleep disorder event;

wherein each $j^{th}$ ($1 \leq j \leq N$) mandible movement class consists of a $j^{th}$ set of rotational values, each $j^{th}$ set of rotational values being indicative of at least one rate, rate change, frequency, or amplitude of mandibular rotations associated with the $j^{th}$ class;

sampling, by means of a sampling element comprised in the data analysis unit, the rotational movement data during a sampling period, thereby obtaining sampled rotational movement data;

deriving, by means of the data analysis unit, a plurality of measured rotational values from the sampled rotational movement data; and, matching, by means of the data analysis unit, the measured rotational values to the N mandible movement classes.

In some embodiments, the method further comprises the steps of:

measuring accelerations by means of an accelerometer, the accelerations being indicative of movements and/or positions of the head and/or mandible of the subject;

sending, by means of the data link, measured acceleration date from the accelerometer to the data analysis unit;

wherein each $j^{th}$ ($1 \leq j \leq N$) mandible movement class comprises of a $j^{th}$ set of acceleration values, each $j^{th}$ set of acceleration values being indicative of at least one mandibular movement or head movement associated with the $j^{th}$ class;

sampling, by means of a sampling element, the measured acceleration data during a sampling period, thereby obtaining sampled acceleration data;

deriving, by means of the data analysis unit, a plurality of measured acceleration values from the sampled acceleration data; and, matching, by means of the data analysis unit, the measured acceleration values with the N mandible movement classes.

In some embodiments, the method further comprises the steps of:

measuring, by means of a magnetometer, magnetic field data, the variations in magnetic field data being indicative of movements of the head and/or of the mandible of said subject;

sending, by means of the data link, measured magnetic field data from the magnetometer to the data analysis unit;

wherein each $j^{th}$ ($1 \leq j \leq N$) mandible movement class comprises of a $j^{th}$ set of magnetic field data values, each $j^{th}$ set of magnetic field data values being indicative of at least one rate or rate change of mandibular movement or head movement associated with the $j^{th}$ class;

sampling, by means of a sampling element comprised in the data analysis unit, the measured magnetic field data during a sampling period, thereby obtaining sampled magnetic field data;

deriving, by means of the data analysis unit, a plurality of measured magnetic field values from the sampled magnetic field data; and, matching, by means of the data analysis unit, the measured magnetic field values with the N mandible movement classes.

In some embodiments, the method further comprises the step of identifying, by means of the analysis unit, a movement of the head of the subject based on the gyroscope data, on the accelerometer data, and/or the magnetometer data.

In some embodiments, at least one of the N mandible movement classes is indicative of bruxism, and wherein the measured rotational movement data is indicative of a mandibular movement amplitude of at least 1 mm, at a frequency established in a range of 0.5 to 5 Hz during at least three respiratory cycles when the movement is phasic, or beyond 1 mm in a sustained, tonic manner for at least 2 seconds.

Systems and methods are further provided herein for diagnosing a sleep event of a subject. The systems and methods may include receiving mandibular rotational data generated by a gyroscope mounted on an exterior of a mandible of the subject, the mandibular rotational data corresponding to a time period during sleep and indicative of rotational movement of the mandible of the subject; receiving mandibular acceleration data generated by an accelerometer mounted on the exterior of the mandible of the subject, the mandibular acceleration data corresponding to the time period during the sleep and indicative of acceleration of the mandible of the subject; determining the mandibular rotational data is above a first threshold value; determining the mandibular acceleration data is below a second threshold value; and generating information for diagnosing the sleep event of the subject based on the mandibular rotational data being above the first threshold value and the mandibular acceleration data being below the second threshold value.

The gyroscope and the accelerometer may be disposed within a housing adhered to the exterior of the mandible of the subject. The sleep event may correspond to one of a normal event, an obstructive event (e.g., obstructive sleep apnea (OSA)), a central event, an arousal event, or motor event. The system and method may further include applying the first data and the second data to a machine learning model to determine a presence of the sleep event, the machine learning model trained to output likelihoods of a presence of a set of plurality of sleep events based on accelerometer data and gyroscope data. The system and method may further include applying the first data and the second data to a second machine learning model to determine a presence of a sleep stage corresponding to the time period. The sleep stage may be one of awake, light sleep, deep sleep, or rapid eye movement (REM) sleep.

The system and method may further include applying the sleep stage to the first machine learning model to determine the presence of the sleep event, receiving third data generated by a pulse oximeter worn by the subject and corresponding to the time period, wherein the information generated for diagnosing the sleep event of the subject is further based on the third data. The system and method may further include determining an absence of the sleep event based on the third data. The system and method may further include determining third data generated by a thermistor positioned on the exterior of the mandible of the subject and corresponding to the time period, the third data indicative an airflow generated by respiration of the subject, wherein the information generated for diagnosing the sleep event of the subject is further based on the third data. The system and method may further include determining an absence of the sleep event based on the third data being above the third threshold value. The system and method may further include generating a report indicating the presence of the sleep event of the patient at the time period.

DESCRIPTION OF THE FIGURES

The invention will now be described in more detail with the aid of the drawings, which show the system and its operation. The present system may be described as a system of a sensing unit and a device or unit for processing sensed data. In the drawings:

FIGS. 1A-E show a sleep assessment system including a sensing unit and views of the sensing unit according to the invention.

FIGS. 3A and 3B show streams captured by the sensing unit during bruxism.

FIGS. 22A-22C show an exemplary report including sleep states, respiratory events, awakenings and arousals.

DETAILED DESCRIPTION

Figure 1A:
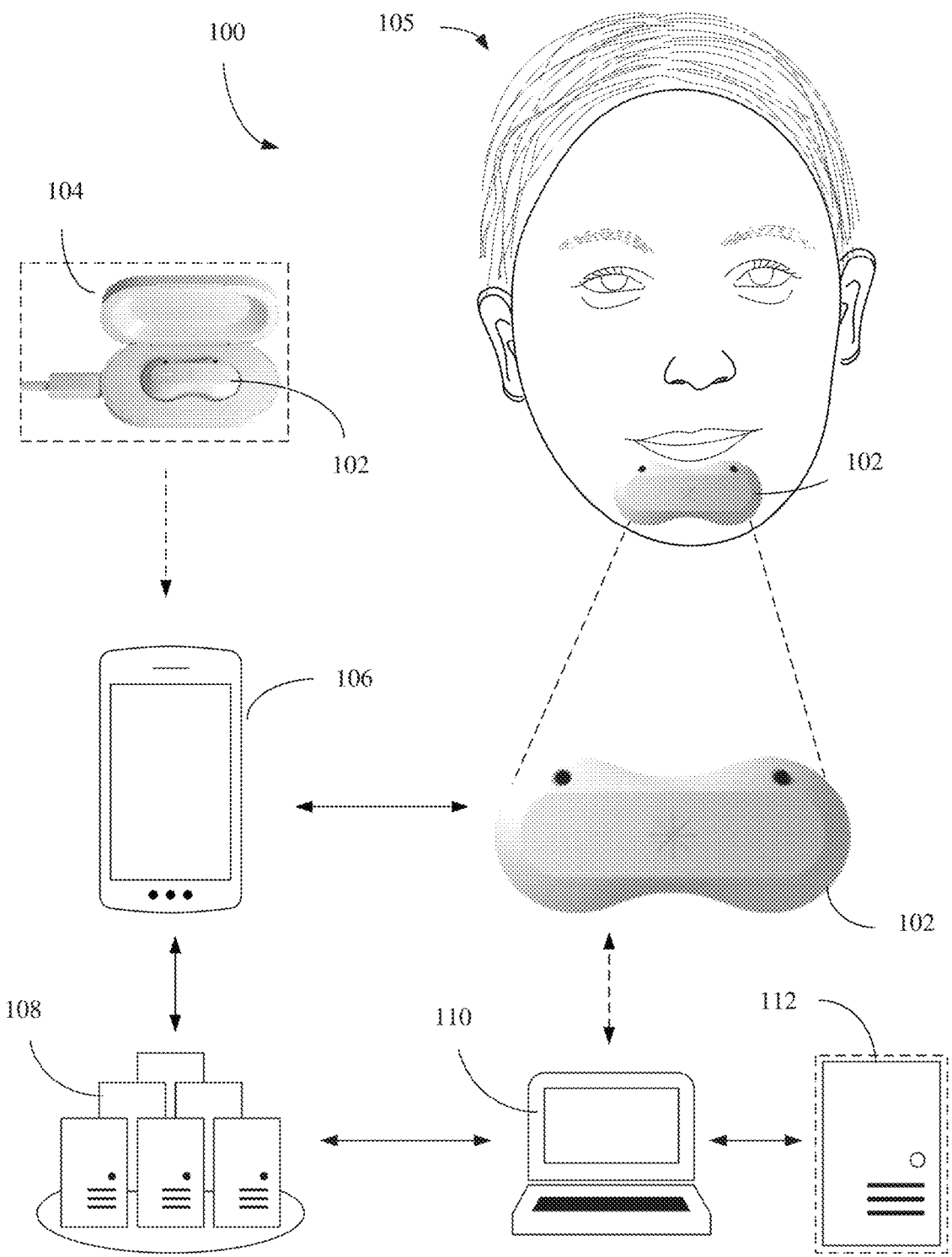

A medical device is provided herein that includes a cloud-based software device that analyzes data from a sensor placed on the patient's mandible. The device may record patient's responses to questions about their sleep quality. By analyzing patient's mandibular movements in a non-invasive manner, the device also may detect a sleep event(s) (e.g., obstructive respiratory disturbances such as obstructive sleep apnea (OSA)), identify sleep states, notify about the OSA severity in a categorical format (non-OSA, mild-OSA, moderate-OSA, severe-OSA), and/or generate sleep structure information (namely, total sleep time, sleep onset latency, wake after sleep onset, sleep efficiency, arousal index) and head position discrete states. Data collected by the device may be integrated in a report for further interpretation by the healthcare provider. The healthcare provider can then diagnose a sleep event(s) using the enhanced information provided by the inventive device.

Before the present systems and processes of the invention are described, it is to be understood that this is not limited to particular systems and methods or combinations described, since such systems and methods and combinations may, of course, vary. It is also to be understood that the terminology used herein is not intended to be limiting, since the scope will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed aspects and embodiments. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of the members, or to any two or more of the members, such as, e.g., any ≥3, ≥4, ≥5, ≥6 or ≥7 etc. of the members, and up to all the members.

All references cited in the present specification are hereby incorporated by reference in their entirety. In particular, the teachings of all references herein specifically referred to are incorporated by reference.

Unless otherwise defined, all terms used herein, including technical and scientific terms, have the meaning as commonly understood by one of ordinary skill in the art. By means of further guidance, term definitions are included to better appreciate the teaching as described herein.

In the following passages, different aspects are defined in more detail. Each aspect so defined may be combined with any other aspect or aspects unless clearly indicated to the contrary. In particular, any feature indicated as being preferred, particular or advantageous may be combined with any other feature or features indicated as being preferred, particular or advantageous.

The present invention relates to the measurement and assessment of mandibular movement of a sleeping subject. The mandible or lower jawbone sits beneath the maxilla and forms the lower jaw. It is the only movable bone of a human skull (discounting the ossicles of the middle ear). During movement, the mandible pivots around the temporomandibular joint, where the mandible connects to the skull (temporal bone) in front of the ear. During mandibular movement the relationship between the length and the tension of muscular fibres anchored on the mandible will change, which may result in a stiffening of the upper airways in subjects who are at risk of instability during sleep. This movement is activated under agonist and antagonist muscles for elevating or lowering the mandible, thereby closing or opening the mouth, respectively. The agonist and antagonist muscles are innervated by motor neurons originating from the nucleus of the trigeminal nerve located in the brainstem (mid-pons) and are supported by the motor branch of this nerve.

Referring now to FIGS. 1A-1E, a system for characterizing sleep disorders in a subject having a head and a mandible is depicted. Referring now to FIG. 1A, sleep assessment system 100 is illustrated. Sleep assessment system 100 may be used to characterize, measure, assess, and/or diagnose sleep disorders. For example, sleep assessment system 100 may be a non-invasive home care aid in the evaluation of a sleep event (e.g., obstructive sleep apnea (OSA)) with suspicions of sleep breathing disorders. Sleep assessment system 100 may include sensing unit 102, which may be mounted externally (e.g., via an adhesive such as biocompatible tape and/or glue) to a mandible of user 105 such that sensing unit 102 is positioned extra-orally on the user's skin (e.g., between the lower tip of the chin and lower lip of the subject). In a preferred embodiment, sensing unit 100 includes an accelerometer and a gyroscope and also may include one or more additional sensors such as a magnetometer, oximeter for determining photoplethysmograph (PPG) data and/or other PPG sensor, thermometer (e.g., thermistor), audio sensor (e.g., microphone), electromyography (EMG) unit, and/or any other suitable sensor for sensing a magnetic field, blood oxygenation, temperature, airflow (e.g., inhales and exhales), sound, electrical activity of muscles, heart rate, and the like. In one example, audio signals from the microphone may be used to detect a respiratory event (e.g., snoring, obstruction, etc.). For example, if the detected audio signal is above a threshold (e.g., a certain amount of decibels) and/or conforms to a predetermined pattern, a data analysis unit may determine the detected sound is indicative of an obstruction and/or snoring.

The gyroscope may be designed to measure rotational movements of the mandible of the subject, which, as observed by the inventors, is an activity that gyroscopes are particularly well-suited for. The gyroscope can be used to assess the activity of the brainstem stimulating mandible movement during sleep, in a way to keep open the upper airways (pharynx) and prevent from sleep disordered breathing. The mandibular mobile bone is turned around like a lever to stretch pharyngeal muscular fibres attached directly or indirectly (via the second mobile bone—the hyoid bone) including the tongue, on the mandibular bony arch.

To some extent the gyroscopic movement is representative of the central drive meaning that the nucleus of the trigeminal nerve in the pons is acting to finely displace the mandible with regard to the respiratory centres located also in the brainstem and under the influence of higher centres responsible for the sleep organization (sleep staging). As a result, the provision of a gyroscope in a sensing unit can be used for assessing various sleep related activities, by looking at the rotational mandibular displacements, which may include respiration, sleep stages or other events (e.g. movement or motor events). Moreover, values measured by gyroscope arranged for measuring rotational movements of the mandible of the subject, such as the rate and the amplitude of the mandibular gyroscopic signal, in addition to metrics directly or indirectly derived from the measured values, can be used for obtaining assessment of the central drive stemming from the nucleus of the trigeminal nerve.

The inventors have found that other sensing units are not suitable for the measurement and assessment of mandibular movement as provided herein. For instance, an inertial sensor like an accelerometer allows only a limited measurement of linear acceleration and is thus unsuitable for measurement of rotational mandibular displacements. Measurement by an accelerometer can be affected by movement of the body or the head, such as the chest or trachea during breathing and distinguishing between the origins of data is difficult and adds unnecessary noises and complexity to the system. As a result, the link between the possible body and head movement is not taken sufficiently into consideration by existing systems for analysis of sleep disturbances. This has a negative impact on a diagnosis that is based on the measured data streams. The inventors have found that the rotation of the mandible carries the necessary information to arrive at an accurate assessment and moreover that such movement can accurately be recorded by a gyroscope.

Sleep assessment system 102 may further include mobile device 106, server 108, analysis device 110, and optionally storage device 112. Mobile device 106 may be any computing device having a processor, memory, and communication unit for communicating with sensing unit 102 via any suitable wired or wireless connection or technology (e.g., Wi-Fi, cellular network, Bluetooth, Bluetooth Low Energy (BLE), near field communication protocol, etc.). For example, mobile device 106 may be a smartphone, smartwatch, wearable device, tablet, laptop, and the like. Mobile device 106 may be in communication with server 108, which may be a remote server. Server 108 may be one or more computing devices having a processor, memory, and a communication unit. Server 108 may communicate with mobile device 106 and/or analysis device 110 via any wireless connection or technology. Analysis device 110 may be any computing device (e.g., laptop, desktop, tablet, smartphone, etc.) having a processor, memory, display, and/or communication unit. Storage device 112 may be optional and may be any suitable storage device for storing digital information (e.g., datastore, server, etc.) and may have a processor, memory, and communication unit. Analysis device 110 may communicate with server analysis device 112 via any suitable wired or wireless system. Analysis device 110 may optionally communicate with sensing unit 102 (e.g., over the Internet). Sleep assessment system 100 may further include charging device 104, which may be used to charge a rechargeable battery in sensing unit 102. In one example, charging device 104 may include a processor, memory, and may communicate via a suitable wireless connection or technology with mobile device 106 and/or communicate with sensing unit 102 via any suitable wired or wireless connection or technology.

Data and/or information generated by sensing unit 102 may be communicated to mobile device 106, server 108, analysis device 110 and optionally storage device 112. In one example, data generated by sensing unit 102 (e.g., gyroscope and/or accelerometer data) may be sent from sensing unit 102 to mobile device 106. Mobile device 106 may then send the data generated by sensing unit 102 to server 108 for analysis on server 108. Analysis device 110 may be used by a healthcare provider and may receive analyzed data based on the data generated by sensing unit 102 and/or a report based on such data. Analysis device 110 may further receive raw data generated by sensing unit 102. Analysis device 110 may store the data received from server 108 in storage device 112. In this manner, the healthcare provider interacts with the device through the proprietary platform at analysis device 110 and the patient interacts with device through the proprietary mobile application at mobile device 106. In some embodiments, the system generates a healthcare-level report for use by the healthcare provider (e.g., for diagnosing a sleep event(s)) and a patient-level report for use by the patient. In some embodiments, the patient-level report has less detail on the sleep analysis than the healthcare-level report.

In one example, sensing unit 102 may generate gyroscope data and/or other sensor data and may send the data to mobile device 106 via a data link. The data link may be a wireless connection that provides a communication path between the gyroscope and other sensors of the sensing unit (e.g., accelerometer) and mobile device 106. Server and/or analysis device 110 may include a data analysis unit for analysing the data generated by sensing unit 102. Preferably, the data link is a wireless datalink, e.g. because of improved subject comfort, though data links employing communication by wire are certainly possible as well.

Rotational movement data is sent via the data link from the gyroscope to the data analysis unit. The data link is of a conventional nature and contains arrangements for transferring data either wirelessly or by wire.

The data analysis unit comprises a memory unit, e.g. a data storage device such as hard drive, solid-state drive, memory card or the like. The memory unit is configured for storing a number (N) mandible movement specific patterns (classes), with N an integer larger than one. At least one of the N mandible movement classes is indicative of a sleep disorder event. Preferably, the N mandible movement classes comprise a plurality of movement classes which are indicative of various mandibular movements. Each $j^{th}$ ($1 \leq j \leq N$) mandible movement class comprises of a $j^{th}$ set of rotational values, and each $j^{th}$ set of rotational values is indicative of at least one rate, rate change, frequency, and/or amplitude of mandibular rotations associated with the $j^{th}$ class.

The rotational movement data measured or recorded by the gyroscope is linked to the mandible movement classes as follows:

The data analysis unit comprises a sampling element configured for sampling the measured rotational movement data during a sampling period. Thus, sampled rotational movement data is obtained. Information contained in the signals recorded by the gyroscope may thus be extracted for further analysis. It shall be understood that in some embodiments, the data analysis unit may be comprised in a general purpose computing device such as a personal computer or a smartphone, though the provision of specialized hardware is certainly possible as well.

The data analysis unit is configured to derive a plurality of measured rotational values from the sampled rotational movement data, and for matching the measured rotational values with the N mandible movement classes. Preferably, deriving the measured rotational values from the sampled rotational movement data comprises one or more of the following procedures: discretization, time-averaging, fast Fourier transformation, etc. Additionally, the matching may be fully or partially automated by the provision of a machine learning model, such that the data analysis unit is configured to learn a number of statistical and/or physical metrics in order to capture the characteristics of the signal in frequency and time domains and identify patterns of rotation signal to specific events, such as sleep stages, respiratory efforts, and the like. The provision of a machine learning model may thus provide for automatic interpretation of the relevant information and/or matching characteristic data with sleep disorder events Study of mandibular movement during sleep therefore provides information on the respiratory control state in response to changes of permeability or of resistance to flow of the air flows in the upper respiratory tracts, whether or not that is involved in series of modifications in the position of the head. Analysis of the nature of mandibular movement using the system according to the invention can also detect non-respiratory motor events repeated during sleep, such as bruxism or chewing, or of an isolated nature, such as oro-facial dyskinesia. Deglutition and suckling movements in the infant can also be clearly identified. Additionally, deglutition movements can be detected in adults as well. This allows differentiating arousals from micro-arousals.

In some embodiments, one or more mandibular movement classes are indicative of an isolated large mandibular movement (IMM). IMMs are associated with micro-arousals or respiratory disturbance induced arousals, such that micro-arousals can be effectively inferred from the measurements and the analysis.

In some embodiments, the process of matching the measured rotational values with the N mandible movement classes makes use of an artificial intelligence method, for example random forests.

In some embodiments, sensing unit 102 may further include an accelerometer. The accelerator is adapted to measure accelerations (including acceleration variations) which are indicative of movements and/or positions of the head and/or mandible of the subject. The inventors have found that accelerometers are particularly well-suited for measuring movements and positions of the head. The addition of an accelerometer to the present system allows for further assessing the behaviour of the mandible during sleep. In particular, the inventors have found that the measurement of accelerations can be used to explain unexpected changes in the movement, amplitude and/or rate of the gyroscope. Measurements by an accelerometer may thus be used to supplement measurements performed by the gyroscope.

Measured or recorded acceleration data is sent by the accelerometer to the data analysis unit via the data link. In these embodiments, each $j^{th}$ ($1 \leq j \leq N$) mandible movement class comprises of a $j^{th}$ set of acceleration values. Each $j^{th}$ set of acceleration values or metrics is indicative of at least one mandibular movement or head movement associated with the $j^{th}$ class. The sampling element is configured for sampling the measured acceleration data during a sampling period. After sampling, the measured acceleration data are termed sampled acceleration data. The data analysis unit is configured to derive a plurality of measured acceleration values from the sampled acceleration data, for example by discretization and optionally time averaging. Information contained in the signals recorded by the accelerometer may be extracted for further analysis. The data analysis unit is further configured for matching the measured acceleration values with the N mandible movement classes. This process of matching is understood to involve automatically determining the mandible movement class that corresponds the closest to the measured acceleration values. The matching may be fully or partially automated by the provision of a machine learning model, which may provide for automatic interpretation of the relevant information and/or matching characteristic data with sleep disorder events.

The inventors have found that the accelerometer is particularly sensitive to movements of the head. Together, the gyroscope and the accelerometer allow efficiently discerning head movements from mandible movements, which in turn allows for improved detection of sleep disorder events. As a result, the provision of a gyroscope and an accelerometer in a single system can increase the sensitivity and accuracy of the present system, and may also for assessment of new information that could not be interpreted from the measured values provided by a gyroscope or accelerometer alone. For example, changes in the head position stimulated by a central activation could impact the mandible rotation movement, which could be mistakenly interpreted as changes in the degree of mouth opening or closing. The combination of a gyroscope and an accelerometer can thus allow for discerning head movement from jaw movement. In view of the superior and unexpected functionality provided by the present combination, the presence of a gyroscope cannot be regarded an alternative to other sensing devices, like for example a second accelerometer.

In some embodiments, sensing unit 102 may further include a magnetometer, the magnetometer adapted to measure magnetic field data. The variations in magnetic field data are indicative of the direction of movements and/or positions of the head and/or of the mandible of said subject. The addition of a magnetometer to the present system may allow for further assessing the behaviour of the mandible during sleep. It may be appreciated that the provision of a magnetometer in the present system serves to assess the orientation of the sensing unit similar to a compass. As such, the magnetometer is not intended to serve as a unit for measuring distances as contemplated in systems of the art; although the primary functionality is understood to be not limitative to the scope of the present system.

The data link may further sending measured or recorded magnetic field data from the magnetometer to the data analysis unit (e.g., via mobile device 106). Each $j^{th}$ ($1 \leq j \leq N$) mandible movement class comprises a $j^{th}$ set of magnetic field data values. Each $j^{th}$ set of magnetic field data values is indicative of at least one rate or rate change of mandibular movement or head movement associated with the $j^{th}$ class. The data analysis unit comprises a sampling element configured for sampling the measured magnetic field data during a sampling period. Thus sampled magnetic field data is obtained. The data analysis unit is configured to derive a plurality of measured magnetic field values from the sampled magnetic field data. The data analysis unit is further configured for matching the measured magnetic field values with the N mandible movement classes.

In a particular form, the magnetometer may comprise two parts: one part mounted on the forehead of a patient, and one part mounted on the mandible of the patient. The inventors have found that this is a particularly effective configuration for detecting mandibular movements.

In some embodiments, signals originating from the magnetometer, gyroscope, accelerometer and/or further sensors are transferred via a single physical medium using, for example time-division multiplexing and/or using carrier waves of different frequencies.

In some embodiments, the gyroscope, and/or the accelerometer, and/or the magnetometer or a part thereof are comprised in a sensing unit. The sensing unit is mountable on the mandible of the subject. This is an embodiment with a highly compact form factor, it is easy to apply, and offers improved patient comfort. The provision of an accelerometer and/or magnetometer is understood to not substitute the functionality of a gyroscope, but rather to arrive at new interpretations that are made possible only through the combination of gyroscope with one or more additional sensing devices, such as an accelerometer and/or the magnetometer. Preferably, interpretation of the acquired signal is firstly associated with data from the gyroscope and in a second step supplemented with data from the accelerometer and/or magnetometer. For example, data from the gyroscope may be used first for analysis of the angular speed of the mandible to arrive at a comprehensive cycle by cycle analysis; data from the accelerometer may then be used to provide context on which cycle is produced (e.g, the origin of the activation (cortical and subcortical), the endotype (the dynamic of the breathing disorder), the types of the muscular masticatory activity (more or less tonic or phasic)). Additionally, novel assessment can be made from the combination of data that are not possible based on data from a single sensing unit alone. For example, precise description of the event type opens the possibility of making predictions about the occurrence or reoccurrence of sleep disorder event or changes in breathing (e.g. peripheral capillary oxygen saturation $SpO_2$).

Preferably, sensing unit 102 has a size of at most 5 cm long, 2 cm thick and 1 cm high. This reduces interference with the normal sleep of the subject. However, it is understood that other sizes suitable for extra-oral positioning on user 105 may be used.

In some embodiments, one or more of the N mandible movement classes are associated with a predetermined frequency range. In other words, in these embodiments one or more of the N mandible movement classes comprise mandible movements which occur in a pre-determined frequency range. Preferably, at least two of the N mandible movement classes are associated with a predetermined frequency range, including an $A^{th}$ predetermined frequency range and a $B^{th}$ predetermined frequency range, and the $A^{th}$ predetermined frequency range and the $B^{th}$ predetermined frequency range do not overlap.

In some embodiments, at least one pre-determined frequency range consists of frequencies between 0.15 Hz to 0.60 Hz, or between 0.25 Hz and 0.50 Hz, or between 0.30 Hz and 0.40 Hz. This is the frequency range of signals which are indicative of breathing of the subject.

In some embodiments, sensing unit 102 further comprises one or more ancillary components selected from the list comprising an oximeter and/or a thermometer and/or an audio sensor and/or an electromyography unit and/or a pulse photoplethysmograph. Preferably, these ancillary components are operationally connected to the analysis unit via a data link.

In some embodiments, the analysis unit (e.g., on server 108 and/or analysis device 110) is configured for identifying a movement of the head of the subject based on the gyroscope data, and/or the accelerometer data, and/or the magnetometer data. Preferably, the movement of the head comprises a rotation, e.g. a rotation around an axis through the centre of the head of the subject. Preferably then, at least one of the N mandible movement classes is indicative of a change of position of the head. This allows efficiently discerning generic head movements from movements of the mandible per se. In these embodiments, the system preferably comprises both an accelerometer and a gyroscope.

In some embodiments, the analysis unit is adapted to apply one or more pre-processing steps to the gyroscope data, and/or the accelerometer data, and/or the magnetometer data. The one or more pre-processing steps are selected from the list comprising: the application of a band pass filter, the application of a low pass filter, an exponential mobile mean, and/or a calculation of the entropy of the frequency of the gyroscope data, and/or the accelerometer data, and/or the magnetometer data. The application of low pass filtering improves the detection of micro-arousals.

In some embodiments, the analysis unit may comprise an interpretation module configured for interpreting specific parameters which measure the sleep quality and the extend of sleep breathing disturbances. The sleep quality parameters may include, e.g., total sleep time (TST), seep onset latency (SOL), first awake from sleep onset (WASO), awake index, sleep efficiency (SE), ratios of REM, nonREM sleep, REM sleep latency, and other sleep quality metrics. The sleep respiratory disturbances related metrics may include the hourly occurring rate and cumulated duration of respiratory efforts during sleep. The analysis unit may be configured for reporting the interpreted subject specific parameters. The reporting may include providing an output to a device, such as a computer or smartphone. The reporting may also include providing a visual or textual report of the subject specific parameters, for example in the form of a hypnogram.

In some embodiments, at least one of the N mandible movement classes is indicative of the subject being awake, and wherein a plurality of the N mandible movement classes is indicative of the subject being asleep. Incorporating a classification of "asleep" and "awake" in the present methods ensures that measurements done while the subject is in awake or asleep are interpreted accordingly. The interpretation may be performed using an interpretation module.

In some embodiments, at least one of the N mandible movement classes is indicative of the subject being in an N1 sleeping state; and at least one of the N mandible movement classes is indicative of the subject being in a REM sleeping state. Optionally, at least one of the N mandible movement classes is indicative of the subject being in an N2 sleeping state and/or at least one of the N mandible movement classes is indicative of the subject being in an N3 sleeping state.

In some embodiments, at least one of the N mandible movement classes is indicative of the subject being in an N2 sleeping state.

In some embodiments, at least one of the N mandible movement classes is indicative of the subject being in an N3 sleeping state.

In some embodiments one or more of the N mandible movement classes are associated with a detection of a sleeping stage. Detection of sleeping stages may further be implemented for establishing a subject specific sleeping pattern. The sleeping stage detection is preferably automated at different levels of resolution.

In preferred embodiments the sleeping patterns may include (sorted by increasing level of complexity):
(1) 2 Class (i.e. binary) scoring for detecting the awake or sleeping state in a subject;
(2) 3 Class scoring for classifying the sleeping stage, including the awake state, nonREM sleeping stage or REM sleeping stage in a subject;
(3) 4 Class scoring for classifying the sleeping stage, including the awake state, light sleeping (N1 and N2) stage, deep sleeping (N3) stage or REM sleeping stage in a subject;
(4) 5 Class scoring for classifying all sleeping stages, including the awake state, N1 sleeping stage, N2 sleeping stage, N3 sleeping stage and REM sleeping stage in a subject.

Exemplary method for achieving an automated sleeping stage detection of 3 class scoring is provided in Examples 18 and 19.

In some embodiments, at least one of the N mandible movement classes is indicative of cortical activity. In some embodiments, at least one of the N mandible movement classes is indicative of sub-cortical activity.

In some embodiments, one or more of the N mandible movement classes are indicative of an obstructive apnoea, an obstructive hypopnoea, a respiratory effort linked to arousal, a central apnoea, and/or a central hypopnoea.

In some embodiments, one of the N mandible movement classes is indicative of bruxism, and the measured rotational movement data is indicative of a mandibular movement amplitude of at least 1 mm, at a frequency established in a range of 0.5 to 5 Hz during at least three respiratory cycles when the movement is phasic, or beyond 1 mm in a sustained, tonic manner for at least 2 seconds.

Bruxism during sleep is a frequent complaint by 5 to 10% of the adult population. It is often intermittent, variable in time, sometimes liable to disappear for a few weeks before bouncing back and imposing itself repeatedly during the night, several nights in a row. Bruxism is often recognized by the partner of the sleeper in the form of disagreeable and loud grinding of the teeth. This can lead to facial or temporal pain and signs of wear of the dental enamel in the subject. Its origin is not well understood, but the syndrome of obstructive sleep apnoea has been referred to as one possible cause.

In some embodiments, one or more of the N mandible movement classes is indicative of the loop gain, of the muscular gain mobilizing the mandible during apnoea or hypopnoea ora period of effort, of the point of passive collapsibility after activation and/or of the point of arousability before activation.

Further provided herein is a method for assisting in the characterization of sleep disorders, for example sleep disordered breathing (SDB), in a subject having a mandible. The method comprises the following steps:
receiving, by a data analysis unit and via a data link, rotational movement data from a gyroscope positioned on the mandible of the subject.
storing, by means of a memory unit comprised in the data analysis unit, N mandible movement classes. Note that N is an integer larger than one, and that at least one of the N mandible movement classes is indicative of a sleep disorder event (for example a sleep disordered breathing (SDB) event). Each $j^{th}$ ($1 \leq j \leq N$) mandible movement class consists of a $j^{th}$ set of rotational values, and each $j^{th}$ set of rotational values is indicative of at least one rate, rate change, frequency, or amplitude of mandibular rotations associated with the $j^{th}$ class.
sampling, by means of a sampling element comprised in the data analysis unit, the rotational movement data during a sampling period. Thus sampled rotational movement data is obtained.
deriving, by means of the data analysis unit, a plurality of measured rotational values from the sampled rotational movement data; and,
matching, by means of the data analysis unit, the measured rotational values to the N mandible movement classes.

Thus sleep disorders can be efficiently detected with excellent patient comfort.

In some embodiments, the method further comprises the steps of:
measuring accelerations by means of an accelerometer. The accelerations are indicative of movements and/or positions of the head and/or the mandible of the subject;
sending, by means of the data link, measured acceleration date from the accelerometer to the data analysis unit;
sampling, by means of a sampling element, the measured acceleration data during a sampling period, thereby obtaining sampled acceleration data;
deriving, by means of the data analysis unit, a plurality of measured acceleration values from the sampled acceleration data;
matching, by means of the data analysis unit, the measured acceleration values with the N mandible movement classes. Note that in these embodiments, each $j^{th}$ ($1 \leq j \leq N$) mandible movement class comprises of a $j^{th}$ set of acceleration values, each $j^{th}$ set of acceleration values being indicative of at least one mandibular movement or head movement associated with the $j^{th}$ class.

The use of both accelerometer and gyroscope allows effectively discerning mandible movements from movements of the entire head.

In some embodiments, the method further comprises the steps of:
measuring, by means of a magnetometer, magnetic field data, the variations in magnetic field data being indicative of movements and/or positions of the head and/or of the mandible of said subject;
sending, by means of the data link, measured magnetic field data from the accelerometer to the data analysis unit;
sampling, by means of a sampling element comprised in the data analysis unit, the measured magnetic field data during a sampling period, thereby obtaining sampled magnetic field data;
deriving, by means of the data analysis unit, a plurality of measured magnetic field values from the sampled magnetic field data; and,
matching, by means of the data analysis unit, the measured magnetic field values with the N mandible movement classes. Note that in these embodiments, each $j^{th}$ ($1 \leq j \leq N$) mandible movement class comprises of a $j^{th}$ set of magnetic field data values, each $j^{th}$ set of magnetic field data values being indicative of at least one rate or rate change of mandibular movement or head movement associated with the $j^{th}$ class.

In some embodiments, the method further comprises the step of identifying, by means of the analysis unit, a movement of the head of the subject based on the gyroscope data, and/or on the accelerometer data, and/or the magnetometer data.

In some embodiments, at least one of the N mandible movement classes is indicative of bruxism, and the measured rotational movement data is indicative of a mandibular movement amplitude of at least 1 mm, at a frequency established in a range of 0.5 to 5 Hz during at least three respiratory cycles when the movement is phasic, or beyond 1 mm in a sustained, tonic manner for at least 2 seconds. This combination of parameters is indicative of a bruxism, such that bruxism can be effectively detected. In some embodiments, this frequency range is between 1.0 to 4.5 Hz, or 1.5 to 4.0 Hz, or 2.0 to 3.5 Hz, or 2.5 to 3.0 Hz.

In the following, specific embodiments of matching data (e.g. preferably sampled rotational, acceleration data, and/or magnetic field data), with the N mandible movement classes are discussed. These embodiments involve the extraction of features from the aforementioned data. The features comprise measured rotational values, and optionally include measured acceleration values, and/or measured magnetic field values. Once the features are extracted, they are matched with one or more mandible movement classes. Preferably, the mandible movement classes that the features are matched with comprise central hypopneas, normal sleep, and obstructive hypopneas. Preferably, features are matched with the mandible movement classes by means of a SHAP score to interpret and explain the matching.

In some embodiments, the features are chosen from the non-exhaustive list comprising: central tendency (mean, median and mode) of MM (i.e. mandibular movement, signifying rotations, accelerations, and/or positions measured using a gyroscope, accelerometer, and/or magnetometer) amplitudes; MM distribution (raw or enveloped signals): skewness, Kurtosis, IQR, 25th, 75th and 90th centiles; extreme values: Min, Max, 5th and 95th centiles of MM amplitudes; tendency of variation: Linear trend and coefficients of Tensor product-based spline factors (S1, 2, 3, 4) from a generalized additive model to evaluate MM in function of Time; duration of each event. It shall be understood that such features refer to measured rotational values, measured acceleration values, and/or magnetic values, whether sampled and/or discretized or not. Preferably, the aforementioned values are sampled and discretized. It shall be understood that the list present exemplary embodiments which are therefore regarded as non-limiting to the present system.

In some embodiments, the extraction of features comprises isolating events. An event is a sequence of mandibular movement data (preferably sampled rotational, acceleration, and/or magnetic data) that can be attributed to a single movement of the head and/or the mandible. One specific type of event is normal breathing, for example normal breathing for a pre-determined amount of time. The pre-determined amount of time may be, for example, between 2 and 20 seconds, or between 5 and 15 seconds, 30 seconds or 10 seconds. The time range size may be adapted to the intended application; for example 30 seconds may be suitable for identifying stages of sleep, 10 seconds for sleep bruxism or micro-awakenings, 20 seconds for respiratory events, and so on, In some embodiments, the extraction of features follows the following procedure comprising steps 1 to 4:
1. Obtaining sampled mandibular movement data. The mandibular movement data comprises sampled rotational values, and optionally sampled acceleration values and/or sampled magnetic field values. Preferably, the sampling rate is from 1.0 to 100.0 Hz, or from 2.0 to 50.0 Hz, or from 5.0 to 25.0 Hz, preferably 10.0 Hz. Preferably, obtained sampled mandibular movement data was obtained during a period between 10.0 minutes and 12.0 hours, or during a period between 20.0 minutes and 4.0 hours, or during a period between 30.0 minutes and 2.0 hours.
2. Marking timestamps of mandible movement events.
3. For each time stamp ti, perform the following steps
3.a. Check whether ti is the beginning of a mandible movement event;
3.b. If ti is the beginning of a mandible movement event, assign ti to t_begin, and subsequently search for the ending (t_end) of the mandible movement event; and,
index t_begin and t_end;
4. For each mandible movement event E, perform the following step
4.a. Calculate event duration dt=(t_end−t_begin)
4.b. Determine the statistical distribution of the sampled mandibular movement data during the event. Preferably, this involves calculating one or more features selected from the list comprising Min, Max, Mean, median, mode, $5^{th}$, $25^{th}$, $75^{th}$, $90^{th}$, $95^{th}$ centiles, Skewness, Kurtosis, IQR;

Additionally or alternatively, a GAM (General Additive Model) non-linear model is used to estimate MM amplitude and/or position by a spline function on time t, then the coefficient of spline function is extracted.

Additionally or alternatively, a simple linear model is fitted, and intercept and slope are extracted from the mandibular movements, including amplitude and/or position.

Optionally, all features are concatenated.

The mandible movement event is then matched with a mandible movement class.

In some embodiments, matching a mandible movement event with a mandible movement class involves the use of exploratory data visualization, one-way ANOVA, and pairwise student-t tests with Bonferroni correction. Preferably, during this procedure, significance levels are set at p=0.0001 to 0.01, more preferably at p=0.001.

In some embodiments, a machine learning method, e.g. extreme gradient boosting, deep neural network, convolutional neural network, random forest, is used to classify the measured mandible movement data into mandible movement classes.

In some embodiments, the employed random forest method algorithm employs between 20 and 5000, or between 100 and 2000, or between 200 and 1000, or 500 decision trees. In some embodiments, each decision tree is constructed on a random subset of the aforementioned features.

In some embodiments, model development (i.e. training the artificial intelligence method) involves randomly splitting the measured mandible movement data into two subsets, a larger set for model development and a smaller set for model validation. In some embodiments, the larger set comprises 60 to 80%, or 70% of the measured mandible movement data. In some embodiments, the smaller set comprises 20 to 40%, or 30% of the mandible movement data. Preferably, a synthetic minority over-sampling technique (SMOTE), is used on the training set before the model is developed.

In some embodiments, the model development involves the evaluation of the contribution of a plurality of features to classification by means of the Lundberg's Shapley additive explanation (SHAP) method. The SHAP method thus allows for interpreting the prediction made by the employed machine learning model; it allows for the model to be explainable.

Certain aspects of the present disclosure may be alternatively or additionally worded as follows:

In some embodiments, the system comprises a sensing unit and a device for processing data relating to disturbances that may occur during the sleep of a subject. The processing device includes an identifying unit adapted to identify in the first and second measurement signal streams first signals the frequency of which is situated in a first predetermined frequency range and second signals in which the value of at least one intrinsic characteristic characterizing a movement of the head and/or of the mandible is situated in a second predetermined range consisting of values, said first predetermined frequency range and said second predetermined range consisting of values being frequencies, respectively values, of movements of the head and of the mandible of said subject that characterize a sleeping state of said subject, said identifying unit being adapted to produce a triggering signal after observing that the first and second signals that have been identified in the first and second streams are present for a first predetermined time period, said identifying unit being also adapted, after it has produced the triggering signal, to identify in the first and second measurement signal streams third signals in which the frequency and/or the value of said at least one intrinsic characteristic represents a movement of the mandible and/or a change of the position of the head of said subject, said identifying unit being connected to an analysis unit adapted to be activated under the control of the triggering signal, said analysis unit being also adapted to compare the third signals to profiles that characterize frequencies and/or values linked to sleep disturbances and to produce a result of that comparison. The invention is based on the concept that during sleep of the subject the respiratory movement of that subject is controlled by the nerve centres of the brain of that subject, which nerve centres control the muscles of the head and of the mandible that are attached thereto, which muscles will then position the head and the mandible of that subject. The accelerometer, as well as the gyroscope, will each supply a respective time stream of measurement signals that characterize the movements of the head and of the mandible. Using the identifying unit makes it possible to identify in these streams of measurement signals those that characterize a sleeping state of that subject and thus to activate the analysis unit to analyze any disturbances of sleep affecting the subject when the subject is actually asleep.

Thus it has been found that the movement of the mandible is determined, not only by the movement of the thorax, but also directly by the nerve centres of the brain that control the muscles attached thereto and that will position the mandible. They also control the position of the head.

In fact the tracheal tug, which is necessarily at the respiration frequency, can cause the head to move and it is for this reason that a measurement by both the accelerometer and by the gyroscope is preferred. In fact, the gyroscope is more sensitive to a movement of rotation of the mandible actuated by its own muscles under direct control of the brain than the accelerometer, which will show the movement of the head that the tracheal tug can produce. Outside of the respiratory movement, upon central activation, it is an isolated signal of large amplitude that will be measured. However, the movement imposed by the tracheal tug is a movement damped by the elasticity of the tissues that connect the mandible to the rest of the head and can therefore passively transmit a movement. This is therefore a relatively imperceptible reflection of the spinal drive, that is to say the diaphragm that produces the tracheal tug, whereas the antagonist/agonist muscles of the mandible impart a direct movement, notably by the action of the driving branch of the trigeminal nerve direct from the brain, i.e. the trigeminal drive. The gyroscope enables good measurement of movements of rotation of the mandible that are produced by the muscles of the mandible and that are therefore the result of a direct action of the brain on the mandible.

Combining the signals coming from the accelerometer and from the gyroscope therefore enables improved detection of the origin and the nature of the mandibular movement and therefore improved determination of whether the human being is sleeping or not.

Preferably, the sensing unit (e.g., sensing unit 102) includes a magnetometer adapted to measure movements of the head and/or of the mandible of said subject, which device or unit includes a third input for receiving a third time stream of measurement signals coming from the magnetometer, said analysis unit being adapted to integrate the measurement signals coming from the magnetometer with the third signals. Using a magnetometer makes it possible to determine an absolute position of the head and of the mandible.

Preferably, the sensing unit includes an oximeter and/or a thermometer and/or an audio sensor and/or an electromyography unit and/or a pulse photoplethysmograph, said identifying device or unit including a fourth and/or fifth and/or sixth and/or seventh and/or eighth input for receiving a fourth and/or fifth and/or sixth and/or seventh and/or eighth time stream of measurement signals coming from the oximeter, respectively from the thermometer, from the audio sensor, from the electromyography unit, from the pulse photoplethysmograph, said analysis unit being adapted to integrate the measurement signals coming from the oximeter, respectively from the thermometer, from the audio sensor, from the electromyography unit, from the pulse photoplethysmograph with the third signals. The identifying device or unit is then adapted to associate the measurement signals coming from the oximeter and/or from the thermometer and/or from the audio sensor and/or from the electromyography unit and/or the pulse photoplethysmograph with the third signals. These measurement signals coming from the oximeter and/or the thermometer and/or the audio sensor and/or the electromyography unit enable more measurement signals to be taken into consideration and thus more reliable analysis of the sleep disturbances.

Preferably, the first predetermined range consisting of frequencies is situated between 0.15 Hz and 0.60 Hz inclusive, the identifying unit being adapted to identify first signals over a time period of at least two respiration cycles of the subject, the second predetermined range consisting of values being a mandible rotation movement amplitude value. That value is for example an amplitude of the order of $1/10$ millimetre i.e. based on normal respiration. The frequency range between 0.15 Hz and 0.60 Hz inclusive characterizes a situation in which the head of the subject is so to speak quasi-immobile and therefore reflects a situation in which the subject is sleeping or is falling asleep.

Preferably, the analysis unit is adapted to identify among the third signals those which in the first and second streams characterize rotation of the head about at least one axis that extends through the head of the subject. The rotation of the head will often go hand in hand with arousal, micro-arousal or cortical and/or sub-cortical activation during sleep and indicate a sleep disturbance.

Further provided herein is a method for automated detection of sleeping stages from mandible rotational movement data preferably recorded by means of gyroscope. The method may be a machine learning-based method according to one or more embodiments as described herein. The method preferably comprises the following steps:

provide sampled rotational movement data from at least 1 subject; the sampled data may be provided by one or more sampling and processing methods as described herein;

feeding the provided data to a machine learning classifier to generate prediction scores;

determining a sleep stage on the basis of the generated scores.

It is understood that preferred embodiments for other methods described in the present specification are also preferred embodiments for the method of automated sleep or sleeping stage detection. Data from the method may be used as input for other methods or devices, which may be therapeutic in nature.

In some embodiments, the sleeping stages may include the following classes (sorted by increasing level of complexity):

(1) 2 Class (i.e. binary) scoring for detecting the awake or sleeping state in a subject;
(2) 3 Class scoring for classifying the sleeping stage, including the awake state, nonREM sleeping stage or REM sleeping stage in a subject;
(3) 4 Class scoring for classifying the sleeping stage, including the awake state, light sleeping (N1 and N2) stage, deep sleeping (N3) stage or REM sleeping stage in a subject;
(4) 5 Class scoring for classifying all sleeping stages, including the awake state, N1 sleeping stage, N2 sleeping stage, N3 sleeping stage and REM sleeping stage in a subject.

Exemplary methods for achieving an automated sleeping stage detection of 3 class scoring is presented discussed in Examples 18 and 19.

Aside from detection of sleeping related disorders, the systems and methods as described herein may also be used for the following exemplary applications: sleeping stage detection and/or sleep quality monitoring in healthy subjects, elderly or subjects suffering from abnormal sleeping patterns. Detection of sleeping disorders, whether clinical or psychological in nature, may allow for tailoring treatments or to a subject's need. Moreover, studying the impact on sleep behaviour on clinical outcomes in a chronic disease may allow for gaining novel insights about said disease and also about the treatments efficacy.

Additionally, the system as described herein may also be used in combination with other systems or methods. These systems may optionally be therapeutic in nature, such as a breathing apparatus (CPAP, BiPAP, Adaptive Support Ventilation), a mandibular advancement orthosis, and an oral device, a device for stimulating nerves and/or muscles whether transcutaneous or implanted, a device for correcting the posture and/or position of the body and/or head during sleeping. In some embodiments an alarm can be coupled to the system or the system may be connected to or provided with a device having an alarm function.

Additionally or alternatively, the present invention may be described by way of the following numbered embodiments. In these numbered embodiments, the term "combination" is equivalent to the term "system", unless the context clearly indicates otherwise.

Embodiment 1. Combination comprising a sensing unit and a device for processing data, e.g. processing unit, relating to disturbances that may occur during the sleep of a subject, which sensing unit includes an accelerometer, adapted to measure movements of the head and/or of the mandible of a subject, and a gyroscope, adapted to measure movements of the mandible of that subject, said sensing unit being adapted to produce measurement signals based on the measurements effected, which device includes first and second inputs for receiving a first, respectively a second, time stream of measurement signals coming from the accelerometer, respectively the gyroscope, characterized in that the device includes an identifying unit adapted to identify in the first and second measurement signal streams first signals the frequency of which is situated in a first predetermined frequency range and second signals in which the value of at least one intrinsic characteristic characterizing a movement of the head and/or of the mandible is situated in a second predetermined range consisting of values, said first predetermined frequency range and said second predetermined range consisting of values being frequencies, respectively values, of movements of the head and of the mandible of said subject that characterize a sleeping state of said subject, said identifying unit being adapted to produce a triggering signal after observing that the first and second signals that have been identified in the first and second streams are present for a first predetermined time period, said identifying unit being also adapted, after it has produced the triggering signal, to identify in the first and second measurement signal streams third signals in which the frequency and/or the value of said at least one intrinsic characteristic represents a movement of the mandible and/or a change of the position of the head of said subject, said identifying unit being connected to an analysis unit adapted to be activated under the control of the triggering signal, said analysis unit being also adapted to compare the third signals to profiles that characterize frequencies and/or values linked to sleep disturbances and to produce a result of that comparison.

Embodiment 2. Combination according to embodiment 1, characterized in that the sensing unit includes a magnetometer adapted to measure movements of the head and/or of the mandible of said subject, said device or unit including a third input for receiving a third time stream of measurement signals coming from the magnetometer, said analysis unit being adapted to integrate the measurement signals coming from the magnetometer with the third signals.

Embodiment 3. Combination according to embodiment 1 or 2, characterized in that the sensing unit includes an oximeter and/or a thermometer and/or an audio sensor and/or an electromyography unit and/or a pulse photoplethysmograph, said identifying device or unit including a fourth and/or a fifth and/or a sixth and/or seventh and/or an eighth input for receiving a fourth and/or fifth and/or sixth and/or seventh and/or eighth time stream of measurement signals coming from the oximeter, respectively from the thermometer, from the audio sensor, from the electromyography unit, from the pulse photoplethysmograph, said analysis unit being adapted to integrate the measurement signals coming from the oximeter, respectively from the thermometer, from the audio sensor, from the electromyography unit, from the pulse photoplethysmograph into the third signals.

Embodiment 4. Combination according to any one of embodiments 1 to 3, characterized in that the first predetermined range consisting of frequencies is situated between 0.15 Hz and 0.60 Hz, the identifying unit being adapted to identify first signals over a time period of at least two respiration cycles of the subject.

Embodiment 5. Combination according to any one of embodiments 1 to 4, characterized in that the second predetermined range consisting of values includes at least one head movement amplitude value that indicates a change of position of the head.

Embodiment 6. Combination according to any one of embodiments 1 to 5, characterized in that the analysis unit is adapted to identify among the third signals those which in the first and/or second stream characterize rotation of the head about at least one axis that extends through the head of the subject.

Embodiment 7. Combination according to any one of embodiments 1 to 6, characterized in that the identifying unit is adapted to identify in the first and second signal streams movements that characterize a movement of the mandible and a change of the position of the head of the subject, said analysis unit being adapted to remove from the movement signal streams at least one characteristic to be used to identify information that characterizes said movement.

Embodiment 8. Combination according to any one of embodiments 1 to 7, characterized in that the processing device is adapted to apply pre-processing to the first and/or second stream by applying thereto a band-pass filter and/or a low-pass filter and/or a exponential mobile mean and/or calculation of the entropy of the frequency of the signals.

Embodiment 9. Combination according to embodiment 7 or embodiment 8 when dependent on embodiment 7, characterized in that the analysis unit is adapted to verify whether during a second time period, in particular a period of 30 seconds, said at least one characteristic to be used to identify information that characterizes said movement has a value that characterizes a sleeping state, respectively a waking state, said analysis unit being adapted to produce a first data item indicating a sleeping state, respectively a waking state, if said at least one characteristic to be used to identify information that characterizes said movement and that is removed from the analyzed signals of the first and second streams received has a value that describes the sleeping state, respectively the waking state.

Embodiment 10. Combination according to any one of embodiments 7, 9 or 8 when dependent on embodiment 7, characterized in that the analysis unit is adapted to verify whether during a second time period, in particular a period of 30 seconds, said frequency and/or at least one characteristic to be used to identify information that characterizes said movement and that is removed from the analyzed signals of the first and second received streams has a value that characterizes an N1 sleeping state, respectively an REM sleeping state, said analysis unit being adapted to produce a second, respectively a third, data item indicating an N1 sleeping state, respectively an REM sleeping state, if said frequency and/or at least one characteristic to be used to identify information that characterizes said movement and that is removed from the analyzed signals of the first and second received streams has a value that represents an N1 sleeping state, respectively an REM sleeping state.

Embodiment 11. Combination according to embodiment 7, 9 or 10, characterized in that the analysis unit is adapted to verify whether during a second time period, in particular a period of 30 seconds, said at least one characteristic to be used to identify information that characterizes said movement and that is removed from the analyzed signals of the first and second received streams has a value that characterizes an N2 sleeping state, respectively an N3 sleeping state, said analysis unit being adapted to produce a fourth, respectively a fifth, data item indicating an N2 sleeping state, respectively an N3 sleeping state, if said at least one characteristic to be used to identify information that characterizes said movement and that is removed from the analyzed signals of the first and second received streams has a value that represents an N2 sleeping state, respectively an N3 sleeping state.

Embodiment 12. Combination according to any one of embodiments 1 to 11, characterized in that said analysis unit is adapted to verify whether during a third time period, in particular a period between 3 and 15 seconds, at least one intrinsic characteristic of the analyzed signals of the first and second received streams has a level that characterizes cortical, respectively sub-cortical, activity, said analysis unit being adapted to produce a sixth data item indicating cortical, respectively sub-cortical, activity, if said at least one intrinsic characteristic of the analyzed signals of the first and second received streams has a level that represents cortical, respectively sub-cortical, activity.

Embodiment 13. Combination according to any one of embodiments 1 to 12, characterized in that said analysis unit is adapted to verify whether at least one intrinsic characteristic of the analyzed signals has a level that characterizes an obstructive apnoea, an obstructive hypopnoea, respectively a respiratory effort linked to arousal, a central apnoea, a central hypopnoea, said analysis unit being also adapted to produce a seventh, respectively eighth and ninth data item indicating obstructive apnoea, hypopnoea, respectively a respiratory effort linked to arousal, central apnoea, central hypopnoea, if said at least one intrinsic characteristic of the analyzed signals of the first and second streams has a level that describes obstructive apnoea, obstructive hypopnoea, respectively a respiratory effort linked to arousal, central apnoea, central hypopnoea.

Embodiment 14. Combination according to any one of embodiments 1 to 13, characterized in that the identifying unit is adapted to identify in the first and second streams values of frequency and/or of at least one intrinsic characteristic that shows a variability not observed during a sleeping state and to produce a neutralization signal on observing such variability and to supply the neutralization signal to the analysis unit in order to neutralize it.

Embodiment 15. Combination according to any one of embodiments 1 to 14, characterized in that the analysis unit is adapted to verify if at least one intrinsic characteristic of the analyzed signals of the first and second streams has increased beyond at least 1 mm, at a frequency established in a range of 0.5 to 5 Hz during at least three respiratory cycles when the movement is phasic, or beyond 1 mm in a sustained, tonic manner for at least 2 seconds, and to produce a tenth data item indicating bruxism during such verification.

Embodiment 16. Combination according to any one of embodiments 1 to 15, characterized in that the analysis unit is adapted to capture one or more values in the first and second streams that give access to the calculation of the loop gain, of the muscular gain mobilizing the mandible during apnoea or hypopnoea or a period of effort, from the point of passive collapsibility after activation and/or from the point of arousability before activation.

Figure 1B:
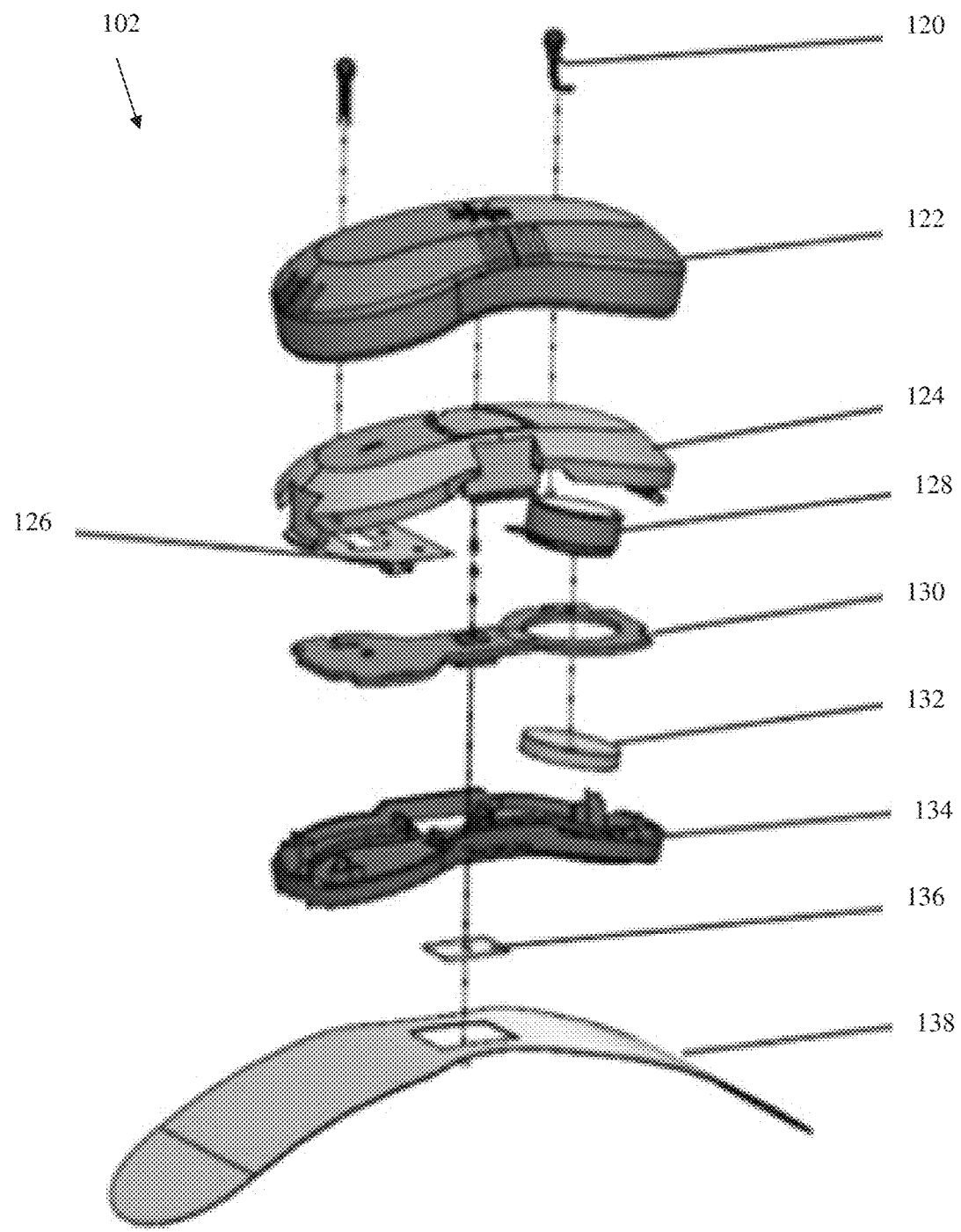

Referring now to FIG. 1B, an exploded view of sensing unit 102 is illustrated. As shown in FIG. 1B, sensing unit 102 may include top housing 122 and bottom housing 134, which may each house components of sensing unit 102. Top housing 122 and/or bottom housing 134 may be made from plastic or any other suitable material and may optionally be flexible. Inner shell 124 may be positioned within top housing 122 and may secure components of sensing unit 102 between inner shell 124 and bottom housing 134. For example, printed circuit board (PCB) assembly 130 may be positioned between inner shell 124 and bottom housing 134.

PCB assembly 130 may be any suitable PCB and may include a processor (e.g., microprocessor), memory, accelerometer, gyroscope, magnetometer, thermometer, oximeter, and/or any other sensors or components of sensing unit 102. Communication unit 126 may be electrically coupled to PCB assembly 130 and may include an antenna and/or transceiver and facilitate wireless communication with other components of the sleep assessment system (e.g., via Bluetooth). Sensors 120 may be electrically connected to PCB assembly 130 and may optionally extend beyond inner shell 124 and top housing 122. For example, sensors 120 may be thermistors. A photoplethysmography (PPG) sensor (e.g., pulse oximeter) may be electrically connected to assembly PCB assembly 130.

Charging coil 132 may also be electrically connected to PCB assembly 130 and may provide an electrical connection between PCB assembly 130 and battery 128 which may be positioned between inner shell 124 and bottom housing 134. Bottom housing 134 may include PPG window 136 to permit light to pass through bottom housing 134 and reach the PPG sensor. Adhesive 138 may connect bottom housing 134 to the skin of a patient (e.g., skin on the mandible of a patient) and may be any biocompatible tape and/or glue. Adhesive 138 may also include a window or aperture to permit to light to pass through adhesive 138 to the PPG sensor.

Referring now to FIG. 1C, a top and bottom view of PCB assembly 130 is illustrated. As shown in FIG. 1C, PCB assembly 130 may include any suitable printed circuit board, microphone 140, photoplethysmography (PPG) sensor 142, accelerometer/gyroscope 144, and microprocessor 146. Photoplethysmography (PPG) sensor 142 may be any suitable PPG sensor used to detect volumetric changes in blood in peripheral circulation of the user to determine a pulse and/or heart rate of the user. Microphone 140 may be any standard microphone for collecting sound data. Accelerometer 144 may be any suitable device that measures or determines acceleration and/or orientation. Gyroscope 144 may be any suitable device that measures or determines rotational motion. Together, accelerometer 144 and gyroscope 144 act as an inertial measurement unit (IMU). PCB assembly 130 may further include a microprocessor, memory, and various other components, sensors (e.g., oximeters, magnetometers, etc.), electronics, and the like.

Figure 1D:
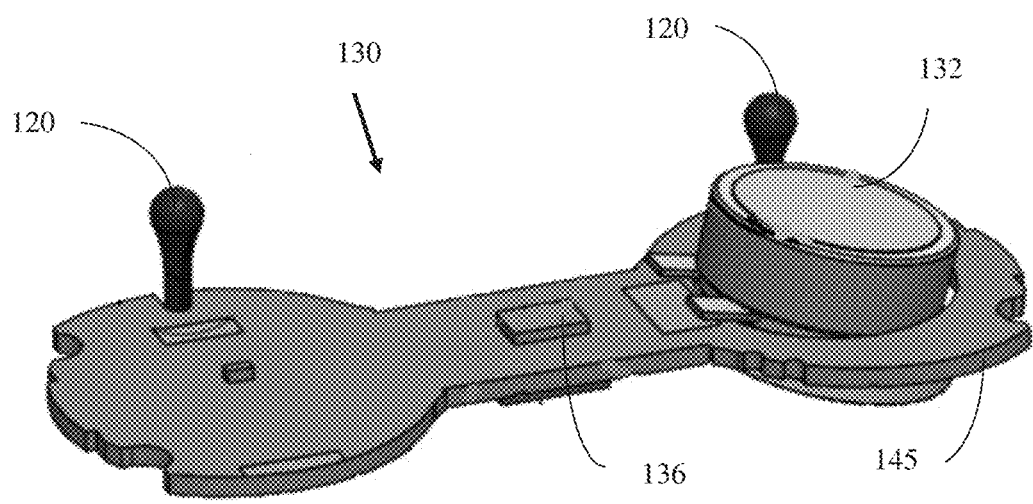

Referring now to FIG. 1D, a perspective view of PCB assembly 130 is illustrated. The PCB of PCB assembly 130 may include PCB 145 which may be any suitable printed circuit board (PCB) and may have a general barbell shape with two circular profiles connected at the center. Sensors 120 may extend upwards from PCB 145. PCB 145 may further include an aperture extending through PCB 145 that may have a size and shape to receive battery 132. PPG sensor 136 may be positioned between the circular portions of PCB 145 and may be oriented downwards such that PPG sensor 136 may have a clear view of the user's skin.

EXAMPLES

Example 1

Figure 1E:
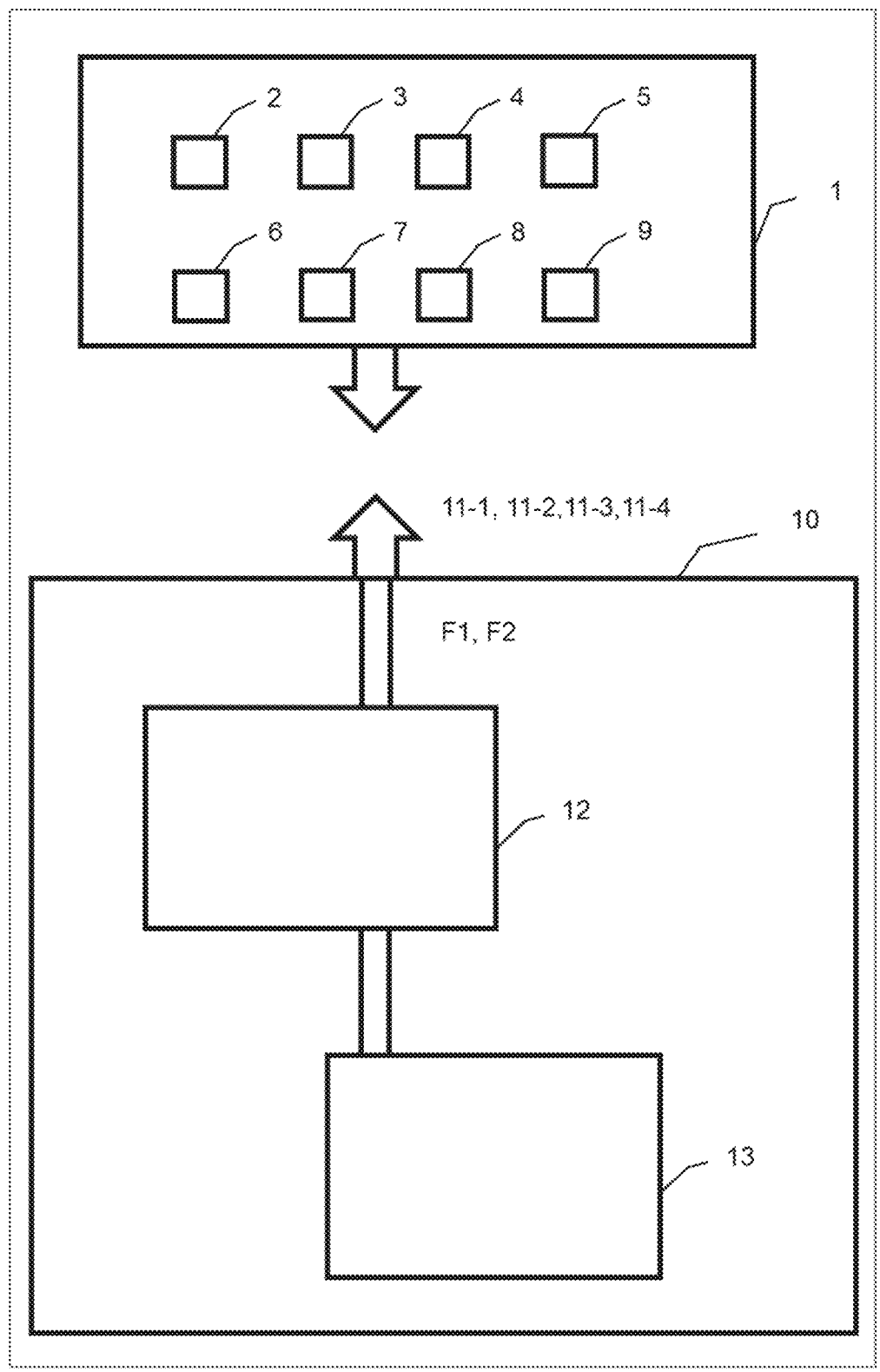

In a first example, reference is made to FIG. 1E. FIG. 1E shows a system according to the invention, which may be the same as or similar to sleep assessment system 100 of FIG. 1A. The system includes a sensing unit 1, which may be the same as or similar to sensing unit 102 of FIGS. 1A-1D, and a device 10 for processing data, preferably a processing unit, relating to disturbances that can occur during the sleep of a subject. Device 10 may be the same as or similar to server 108 and/or analysis device 110. The sensing unit includes an accelerometer 2 adapted to measure movements of the head and/or of the mandible of the subject, preferably in three dimensions. The sensing unit also includes a gyroscope 3 adapted to measure rotation movements of the mandible of the subject, preferably in three dimensions. According to one preferred embodiment, the sensing unit 1 also includes a magnetometer 4, in particular in compass form, and/or an oximeter 5 and/or a thermometer 6 and/or an audio sensor 7 and/or an electromyography unit 8 and/or a pulse photoplethysmograph 9. Other sensors, such as a perspiration sensor or a nasal pressure sensor, may also form part of the sensing unit. The pulse photoplethysmograph functions by transmission or by reflection and gives access to the calculation of the frequency of the pulse and of the change of arterial tonus.

The sensing unit is preferably of small size, for example at most 5 cm long, 2 cm thick and 1 cm high, in order not to interfere with the normal sleep of the subject. The sensing unit is preferably of very small overall size, light in weight and flexible, enabling good ergonomics. The signals produced by the sensing unit are very suitable for decoding using artificial intelligence. The diagnostic power of the measurement obtained by the sensing unit is comparable to that of complete polysomnography recording. The movements of the mandible may preferentially occur on an axis, for example on an anteroposterior axis, whereas the head of the subject is turned to the right. Movements on other axes may equally be measured. The sensing unit is preferably intended to be used only once for reasons of hygiene, but it may of course be reconditioned and reused.

The position of the head is preferably determined on the basis of values measured along the three axes by the accelerometer 2. As the accelerometer measures values of acceleration relative to terrestrial gravity, it is preferred to integrate these measured values over time in order to obtain positions of the head which moreover will be relative positions if there was no initialization phase during application of the sensing unit to the head of the human being.

The position may be expressed according to the value of the pitch, roll and yaw angles, of the Euler angles, or again by tranches of 15°, for example. The position of the head may also be expressed in the following terms: standing, lying down, left, right, on the back.

The table below shows various angle values and the head positions deduced therefrom:

| PITCH | ROLL | YAW | POSITION |
|-------|------|-----|----------|
| 80°   | 0°   | 10° | Upright  |
| 10°   | 10°  | 70° | Lying down, head on left side |
| 20°   | 0°   | 15° | Lying down, head on back |

The magnetometer 4 will be added to sense the orientation of the head, in particular when the movement occurs perpendicularly to the gravity vector. Combining the values measured by the accelerometer and the magnetometer enables calculation of the movement distance and thus an absolute value of the position of the head to be obtained.

As for the movements of the head, the movements of the mandible are measured with the aid of measurements from the accelerometer 2, preferably on the three axes. The movements of the mandible are also measured with the aid of the gyroscope 3.

The movements of the head and of the mandible and the resulting changes of position are of different kinds. For the mandible, the movements are for example movements of rotation at the respiratory frequency. However, latero-lateral movements are possible during sleep in the event of bruxism or chewing, or in the event of oral dyskinesias, and there again the condyle of the mandible is subjected in rotations in the glenoid cavity of the temporomandibular articulation, but these are not about the same axes as in the event of respiratory movements.

For the head, the outcome of the movement is stochastic, i.e. the position that the head will occupy at the end of the movement cannot be predicted after activation. The amplitudes of the movements and of the changes of position have different values. Accordingly, if the amplitude of the movements of the head is high, the changes of position of the mandible measured by the gyroscope are not studied, because if such were the case, the subject is awoken and no information will be obtained on the sleep disturbances of the subject. Small amplitudes of movement of the mandible captured by the gyroscope are observed when they originate in a respiratory movement. A change of the yaw angle is to be related to the head and indicates a rotation of the head from left to right. A change of the pitch angle is to be related to the head in flexion or extension over and above the fact that it provides information on the movement of the mandible albeit using other parameters. These values of the captured signals will be analyzed with the aid of the analysis unit, as described hereinafter.

A mandibular movement may be imposed as much by a respiratory movement as by a non-respiratory movement. Thus movement of the head when the human being is sleeping may cause mandibular movement. Mandibular movement may be produced by the tracheal tug or by the brain of the human being. The tracheal tug is the traction exerted by the thorax on the head of the human being. That traction is at the respiratory frequency of that human being. Thus if the head moves at the respiratory frequency, the mandible, which is attached to the head, will follow that movement imposed by the head, and will do so at the respiratory frequency. This is a passive movement that follows that of the head. Mandibular movement may equally be controlled directly and actively by the brain, and in this case the head will not move. When the brain is controlling mandibular movement, it is the muscles of the mandible that are directly stimulated. It is therefore useful to be able to make a clear distinction between a mandibular movement controlled by the brain and by the tracheal tug.

A distinction is made between isolated mandibular movements (IMM) at the time of activation of the brain, for example at the end of a period of respiratory effort, during a cough, or spitting, or again when talking in one's sleep, and respiratory mandibular movements (RMM) caused by the respiration of the subject. There are also mandibular movements that are caused by bruxism or chewing. RMM type mandibular movements are controlled directly by the brain of the subject and do not lead to movement of the head. An RMM type movement may also be produced by the tracheal tug and will then be combined with a movement of the head at the respiratory frequency. When an RMM type movement stops, is normalized or starts, it is useful to observe, with the aid of the measurements effected by the accelerometer, if the head moved on that occasion. A bruxism type movement very often follows on from an activation that has caused the head to move and that the accelerometer will indicate, because it indeed captures this movement of large amplitude that contrasts with the relatively fine rotatory movement of the mandible that the gyroscope shows clearly.

The device 10 according to the invention for processing data relating to sleep disturbances includes a first input 11-1 for receiving a first time stream F1 of measurement signals coming from the accelerometer 2, i.e. measured acceleration data. It includes a second input 11-2 for receiving a second time stream F2 of measurement signals coming from the gyroscope 3, i.e. measured rotational movement data. It may also include a third input 11-3 for receiving a third time stream F3 of measurement signals coming from the magnetometer 4, i.e. magnetic field data. When the sensing unit also includes an oximeter, said identifying device will include a fourth input adapted to receive a fourth time stream F4 of measurement signals coming from the oximeter, i.e. oximeter data. When the sensing unit also includes a thermometer, said identifying device will include a fifth input adapted to receive a fifth time stream F5 of measurement signals coming from the thermometer, i.e. thermometer data. When the sensing unit also includes an audio sensor, said identifying device will include a sixth input adapted to receive a sixth time stream F6 of measurement signals coming from the audio sensor, i.e. audio data. When the sensing unit also includes an electromyography unit, said identifying device will also include a seventh input adapted to receive a seventh time stream F7 of measurement signals coming from the electromyography unit, i.e. electromyography data. When the sensing unit also includes a pulse photoplethysmograph, said identifying device will also include an eighth input adapted to receive an eighth time stream F8 of measurement signals coming from the pulse photoplethysmograph, i.e. photoplethysmography data. In other words, measurement data from the various sensors is sent from the sensors to the analysis unit via a data link.

The various inputs must not be physically different, because the various streams may be time-division multiplexed and/or each carried by a carrier wave of different frequency. Accordingly, the various input streams may be sent over a single data link.

The device includes a data analysis unit including an identifying unit 12 adapted to identify in the first and second measurement signal streams F1 and F2 first signals the frequency of which is situated in a first predetermined range consisting of frequencies and second signals the value of which is situated in a second predetermined range consisting of values, said first predetermined range consisting of frequencies and said second predetermined range consisting of values being frequencies, respectively values, of movements of the head and of the mandible of said subject that characterize a sleeping state of said subject. When the sensing unit includes a magnetometer 4, the identifying unit 12 will also be adapted to identify in the third stream F3 of measurement signals third signals the value of which is situated in a third predetermined range of values of the orientation of the head of said subject such as may be observed during sleep. The identifying unit is adapted to produce a triggering signal after observing that the first and second signals that have been identified in the first and second streams are present during a first predetermined time period. The identifying unit is also adapted, after it has produced the triggering signal, to identify in the first and second measurement signal streams third signals the frequency and/or the value of which characterizes a movement of the mandible and/or a change of the position of the head of the subject. The identifying unit is connected to an analysis unit 13 adapted to be activated under the control of the triggering signal. The analysis unit is also adapted to compare the third signals to profiles that characterize frequencies and/or values linked to sleep disturbances and to produce a result of that comparison.

In particular, the identifying unit may be comprised in a data analysis unit that also comprises a memory unit. The memory unit is configured for storing N mandible movement classes, wherein N is an integer larger than one, and wherein at least one of the N mandible movement classes is indicative of a sleep disordered breathing event. Each $j^{th}$ ($1 \leq j \leq N$) mandible movement class comprises of a $j^{th}$ set of rotational values, each $j^{th}$ set of rotational values being indicative of at least one rate, rate change, frequency, and/or amplitude of mandibular rotations associated with the $j^{th}$ class. Additionally, each $j^{th}$ mandible movement class optionally comprises a $j^{th}$ set of acceleration values and/or a $j^{th}$ set of magnetic field data values. The data analysis unit comprises a sampling element configured for sampling the measured rotational movement data, and optionally the measured acceleration data and/or the measured magnetic field data, during a sampling period, thereby obtaining sampled rotational movement data and optionally sampled acceleration data and/or sampled magnetic field data. The data analysis unit is configured to derive a plurality of measured rotational values from the sampled rotational movement data; and, optionally to derive a plurality of measured acceleration values and/or measured magnetic field values from the sampled acceleration data and/or the sampled magnetic field data. The data analysis unit is further configured for matching the measured rotational values with the N mandible movement classes. Optionally, the data analysis unit is further configured for matching the measured acceleration values and/or magnetic field values with the N mandible movement classes. Thus, sleep disordered breathing event are effectively detected.

Regarding the data link: the device and the sensing unit preferably communicate with each other wirelessly, but it goes without saying that a cable connection is equally possible. The device is preferably part of a computer situated in a data processing centre. Wireless communication is effected for example with the aid of a telephone communications network and the sensing unit is for example fitted with a Bluetooth system enabling it to communicate with a telephone. Thus the streams of measurement signals produced by the sensing unit will be transmitted to the device.

The invention is based on the fact that it has been observed that the movement of the mandible is not determined only by the movement of the thorax, as the literature indicates, but also by direct control from the nerve centres of the brain that control the muscles that are attached to the mandible and the role of which is to position it. It has been observed that the position of the head, and above all a change thereof during sleep, could stop all mandibular movement or start that movement in a manner entirely independent of the thoracic movement. That is to say that the mandibular movement can follow in the presence of a thoracic movement only if the position of the head allows it and has not immobilized it. The movement of the head can therefore action the mandibular movement or paralyze it and in this sense can be nothing other than the epiphenomenon of a cerebral activation that marks the micro-arousal or arousal and that may have other effects on the mandibular movement.

Movement of the head in fact affects the permeability of the upper respiratory tracts, either by exerting crushing forces when they are more collapsible in a sleeping situation, or by activating/deactivating muscle motor units of the upper respiratory tracts. These movements of the head during sleep modify the permeability of the upper respiratory tracts and must be known and superimposed in time on the movements of the mandible. These movements of the mandible can therefore be analyzed correctly and then interpreted in terms of respiratory control variation starting from the air flow to be produced by the sleeping subject. In other words, sensing and analyzing the mandibular movement taking account of the position of the head and changes thereof during sleep, whether or not on the occasion of micro-arousals or arousal, is to take account of the cerebral control for positioning or repositioning the mandible by activating/deactivating the muscles attached thereto. Outside of cerebral activation, movement of the position of the head at the respiration frequency would be produced by the tracheal tug whereas mandibular movement at the same frequency is determined directly by the nerve centres.

By actuating in the manner of a lever the mobile bone that the mandible forms, cerebral control seeks to stiffen the upper respiratory tracts by activating the muscles of the tongue and of the pharynx attached thereto in order to parry the apnoea. To this end, cerebral control relies on the muscles raising or lowering, opening or closing the mouth during sleep, at the respiration frequency. Cerebral control can also action the muscles that push the mandible forward, also at the respiration frequency, or even action in a combined manner these combined muscular groups that are involved in movements in different directions.

Changes in the position of the head during sleep are often accompanied by an arousal or a micro-arousal that can also be recorded for example by electrodes placed on the scalp and that record the activity of the cortex of the brain. The scalp electrode sometimes registers no activation when there is anyway a movement of the head with a mandibular behaviour modification. The reason for this is that the activation has remained sub-cortical and sometimes purely autonomic in the cerebral trunk. These movements of the head are executed entirely independently of thoracic movement.

Analysis of the mandibular movement in the vertical plane and in the horizontal plane as a function of the position of the head which can, by creating contortion of the neck because this position of the head is no longer aligned with that of the body or because the change in the position of the head is the epiphenomenon of spontaneous or non-spontaneous turning over under the control of the nerve centres, provide information on the level of respiratory effort, in particular its amplitude, that control by the nerve centres of the brain employs on the occasion of the change of resistance to the flow of the air streams through the upper respiratory tracts. The respiratory event is considered as an increase of effort when control from the nerve centres increases, and is considered as central when control by the nerve centres decreases. Cerebral control to enable the organism to exit the apnoea must activate the mandibular lever upward in the vertical plane and forward in the horizontal plane, ideally with the head in axial alignment with the body in order to prevent any compression of the upper respiratory tracts. The (micro)-arousal itself is identified by an isolated large mandibular movement (IMM) and its duration is measured and clearly distinct from the mandibular movements that follow, whether respiratory or non-respiratory.

Example 2

Figure 2A:
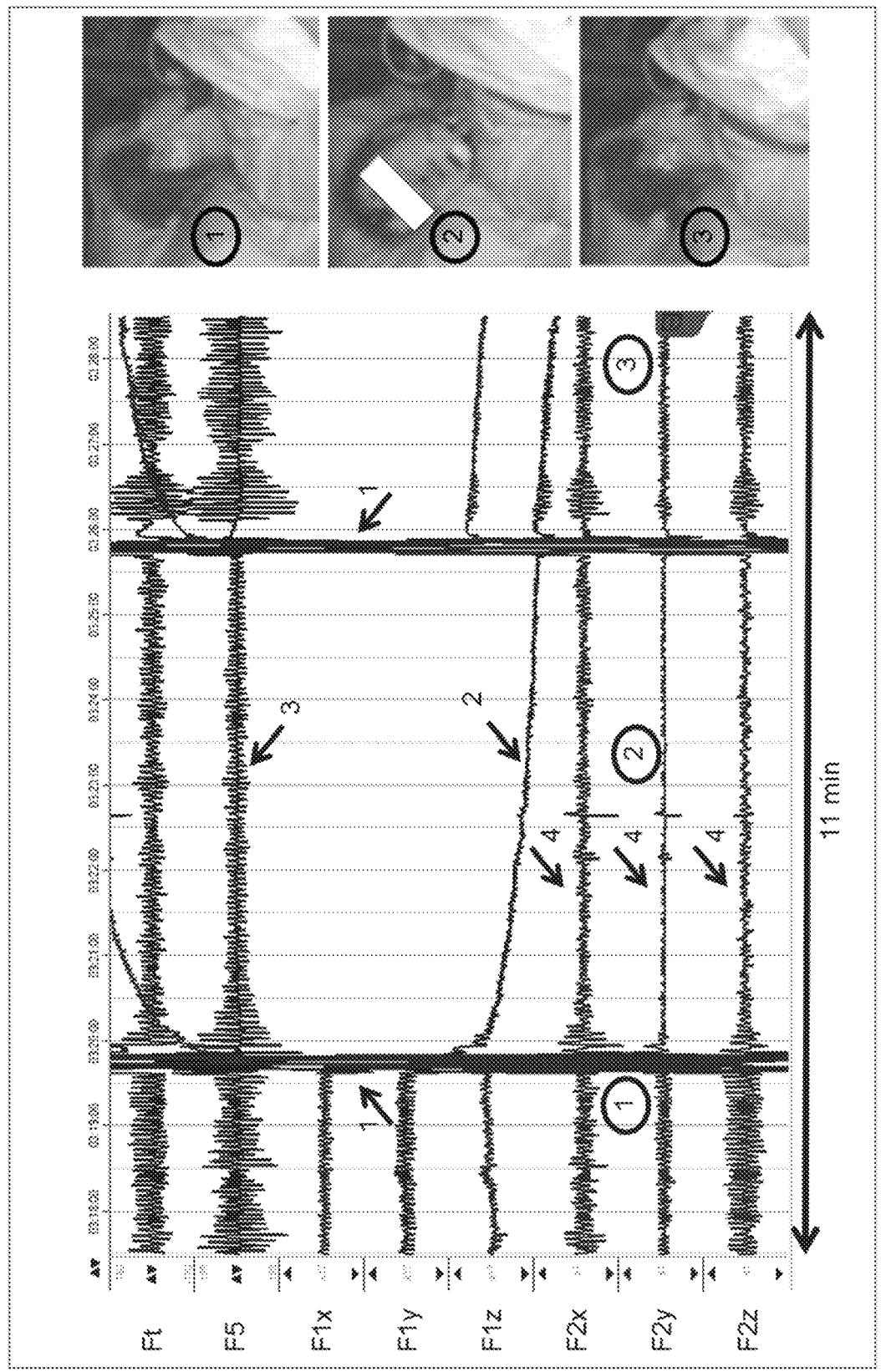
FIGS. 2A and 2B show two streams during a change in the position of the head of a human being lying in bed.
Figure 2B:
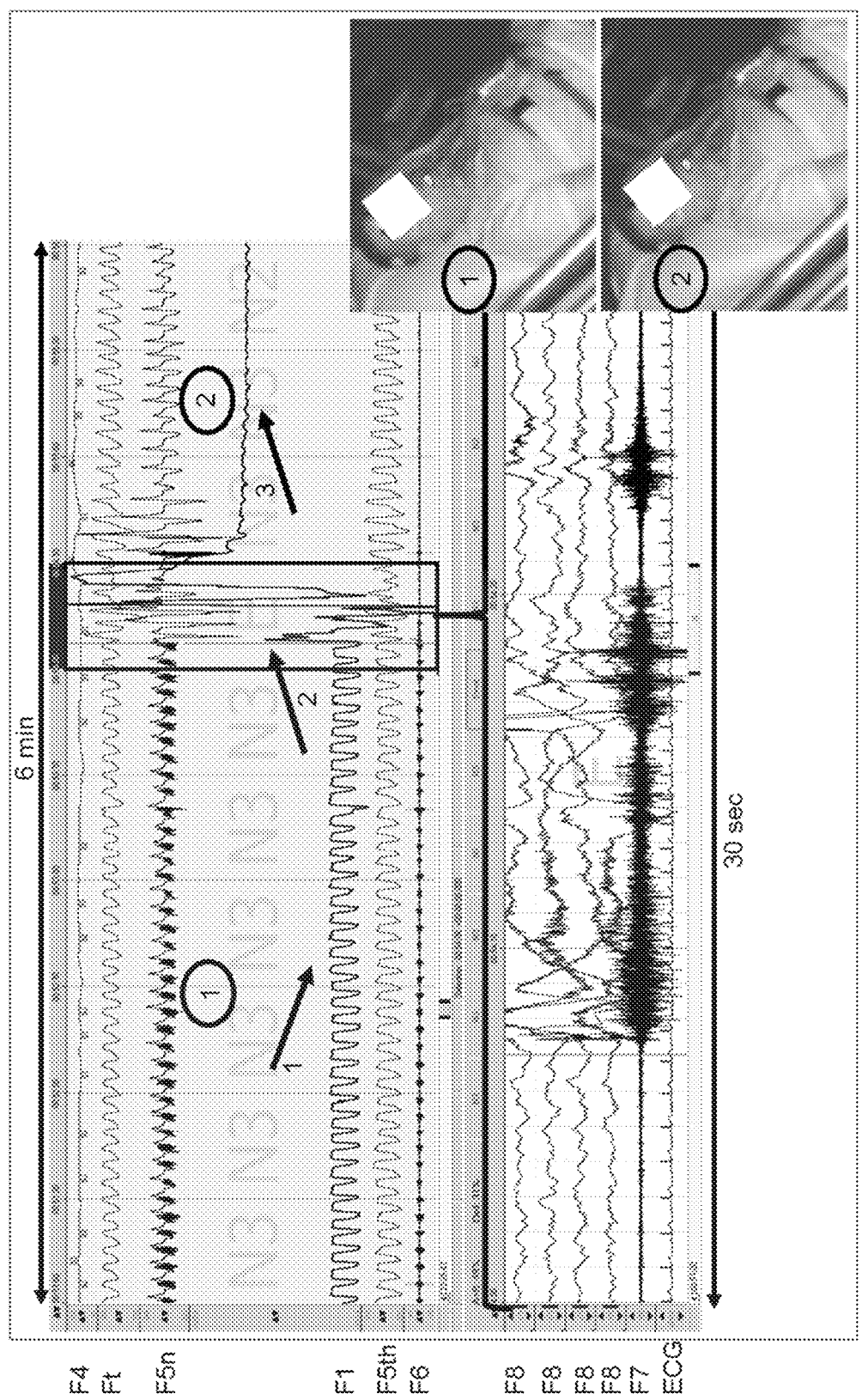

In a further example, reference is made to FIGS. 2A and 2B.

It is on the state of cerebral control that, during sleep, the result of the analysis effected on the measurement data streams coming from the sensing unit provides information, and the change of position of the head, indicated by the signals coming from the accelerometer, is often the marker of its change of state. FIGS. 2A and 2B show streams during a change of the position of the head of a human lying in bed who has an inventive sensor mounted externally on the mandible. This movement can in no way be superposed on the movement of the mandible in the awake and therefore conscious state during mastication, phonation or deglutition as studied by practitioners of an art other than that reserved to sleep medicine. The latter concern problems with mastication, phonation and deglutition studied in dentistry, stomatology, maxillo-facial surgery, orthodontics, orthodontopedics, logopedics, etc. in a conscious subject not in a sleeping state.

FIG. 2A shows, from left to right, firstly a change of the head from a first position, in which the head is turned to the left, to a second position, in which the head is turned to the right. Thereafter is seen a change to a third position in which the head is again turned to the left. The first stream F1, which is that produced by the accelerometer, relates to the three axes (Fx, Fy, Fz) of the three dimensions in which the measurement is effected. The second stream F2, produced by the gyroscope, also relates to the three axes. At the moment when the head turns it is clearly seen that the two streams have a peak of high amplitude. It is also seen that when the head is in the first position the streams F1 and F2 have, in particular in the vertical direction y for the stream F1, a greater variable amplitude that indicates an increased cerebral control state, indicated by the reference 1, and variable in terms of control intensity. Moreover this is also seen in the stream Ft, which shows the movements of the thorax. The analysis unit can therefore deduce from the streams that the person is exhibiting increased and variable respiratory effort.

When the rotation of the head has taken place and it is in the second position, it is seen that the amplitude as much of the stream F1 as of the stream F2 has significantly decreased. The level of the stream F1 is decreasing, which indicates that the mouth has opened, as indicated by the reference 2. It is also seen that the air flow F5 decreases, which could lead to a loss of oxygen flow (reference 3). It is also seen in the stream F2 that the amplitude has decreased, which indicates a loss of cerebral control amplitude, as indicated by the reference 4. All this indicates that the amplitude of the effort has decreased and that respiration is affected (see air flow F5), which will moreover cause cerebral activation and produce a command causing a new change in the position of the head, which turns to the left. After this it is seen in the stream F2 that the amplitude has become greater and that the flow F5 has increased. It will therefore be found that the brain control tends to normalize respiration.

FIG. 2B shows that even a small change in the position of the head is caused by cerebral control. This FIG. 2B shows a change where a slight rotation of the head to the right has occurred. The stream F1 shows firstly, as indicated by the arrow 1, that the cerebral control state has increased and that a respiratory effort has been produced. It is seen that when the head changes position, the accelerometer (F1) shows an increase in amplitude and frequency that indicates cerebral activation, indicated by the reference 2. In the streams F8 (EEG) and F7 (EMG) cerebral activation is clearly seen for a period of 30 seconds, magnified here (reference 2). It is then seen that the level of the stream F1 (reference 3) shows a cerebral control state of reduced amplitude and that the mandible has been raised (the mouth has been closed).

The technique employed by the system according to the invention unexpectedly and unpredictably provides information on the nature of mandibular movement during sleep, its central origin, the control of the nerve centres that have to stiffen the pharynx to maintain ventilation and thereby oxygenation of the subject, whereas its cephalic extremity must during sleep ideally remain in alignment with the body and in particular with the trunk. The mandibular movement must therefore be interpreted as a function of the position of the head and of changes thereof as otherwise why it stops or starts or changes amplitude during sleep would not be understood.

Example 3

In a third example, reference is made to FIGS. 3A and 3B.

The techniques provided herein are applicable to the detection of bruxism. The known diagnosis of bruxism imposes electromyography of the masseter and anterior temporal muscles and possibly anterior temporal muscles during a polysomnographic examination in the laboratory, which examination has moreover to include audio-video recording. This examination is costly, laborious and somewhat inaccessible, since the demand for sleep recordings is out of all proportion to the recording capacities of sleep laboratories. This recording is effected during a single night, and its laborious nature most often prevents it from being repeated. Also, to track bruxism, it must be possible to make recordings over a plurality of nights because it may not be systematically reproduced every night and remain intermittent. It is therefore necessary for it to be carried out at the home of the subject concerned, under real life conditions and without interfering with the natural progress of sleep. The result must be given quickly to optimize taking of control of bruxism and verifying the effects of treatment.

At present, bruxism is not detected in the home, since there is no technical solution for doing this. The solutions proposed, such as surface electromyography of the masseter or anterior temporal muscles do not enable sure diagnosis of the affliction. In fact, the only recording of the electromyographic activity of the masseter or anterior temporal muscles can be affected by parasitic movements during the night or because the adipose medium on the muscle prevents capture of its electromyographic (EMG) activity. Video recording enables the laboratory to verify that the movements of the mandible and the resulting electromyographic activity correspond to bruxism.

The technical solution proposed by the present invention consists in recording mandibular movements with the aid of the sensing unit, preferably on the three principal axes of movement of the mandible in space, and then to carry out algorithmic analysis of the signal with the aid of the analysis unit. That analysis enables identification of mandibular movements that are specifically and exclusively those developed during onset of bruxism as well established by detection of RMMA (rhythmic muscular masseter activity), that is to say phasic but sometimes only tonic activity, during surface electromyography of the masseter. The stream of signals produced by the sensing unit is analyzed on the three axes which also enables capture of the lateral-lateral movement that may be imposed during grinding of the teeth and contribute to wear of the enamel. The mandibular movement, termed bruxism, is the resultant of concomitant action of agonist and antagonist muscles that involve, not only the group of elevators of the mandible, such as the anterior temporal, but also the subhyoid and pterygoid muscles both medialis and lateralis.

FIGS. 3A+B show streams captured by the capture unit during bruxism access. The EMG activity of the muscles recorded, seen as the streams F7D and F7G, has been verified as contributing to mandibular movement. The typical characteristics of masseter and/or anterior temporal electromyographic activity are reflected in mandibular movements that are also pathognomonic of bruxism. The latter are superposed, in the form of a modulated signal, on the tonic (sustained) or phasic (rhythmic) electromyographic bursts of bruxism that generate them. The duration of the cycles or bursts can be calculated.

A period of effort, indicated by the arrow 1, before the onset of bruxism can easily be identified by mandibular movement analysis as well as a transitory arousal, indicated by the arrow 2, accompanied by cortical or merely autonomic, sub-cortical activation. Activation, whether cortical, for example exclusively reflected in a change of cortical wave frequency on the EEG, as indicated by the stream F8, or sub-cortical and not visible on the EEG, is well marked by prior mandibular movement and it is described in the literature that it often precedes the onset of bruxism. It is noted that the masseter phasic and/or tonic activity peaks are contemporaneous with extreme positions of the mandibular movement clearly verifying the relation between muscular recruitment and movement of the mandibular mobile bone. There is seen in FIG. 3A in the stream F1 a period of effort, indicated by the arrow 1, followed by activation, indicated by the arrow 2, in turn followed by movement of the mandible caused by bruxism, indicated by the arrow 3. FIG. 3B is an enlarged view of the period of 10 seconds indicated by the arrow K top right in FIG. 3A. This FIG. 3B shows synchronicity between the activity in the EMG of the right masseter (F7D) and the left masseter (F7G) and bruxism mandibular movements.

It is seen here that the resumed activity of the stream F7 (EMG) of the right masseter (F7D) is synchronized with that of the left masseter (F7G) and that of mandibular movement caused by bruxism. The figure clearly shows, after a period of effort shown clearly on F1Z and F2X, the occurrence of changes at the respiration frequency of the position of the mandible of abnormal amplitude. There follows in F1Z a large movement with movement of the head and on the gyroscope F2X, after a movement marking cortical activation, four rotary movements at high frequency (1 Hz) that correspond to an onset of bruxism. Thereafter, a period of effort reappears.

Movements of the head and of the mandible analyzed via their intrinsic characteristics, that is to say inter alia frequency characteristics and morphological characteristics of the signal streams, may be differentiated as a function of their production mechanism and be sequenced in time, successively. These characteristics can be observed by analyzing for example the amplitude, the area or the slope of the measured signal. They are for example:

Movements linked to respiratory effort, then

Movements linked to transient cortical or sub-cortical activation, then

Movements linked to bruxism or chewing movements that can be clearly differentiated, such as for example the number of bursts during the bruxism cycle, the length of the cycle between two bursts, or the duration of the burst.

The mandibular movement is produced by the agonist/antagonist play of the muscles for raising and lower the mandible. The latter are directly controlled by the cores of the cerebral nerve centres of the trigeminal drive branch. Here the mandibular movement can be sensed by changes of the angle that the mandible exhibits during its movement relative to a plane, for example during its vertical movement relative to the horizontal plane.

Mandibular movement may begin or stop only on the occasion of a change of the position of the head, even if thoracic movements continue. A change of head position is always contemporaneous with a cortical or sub-cortical micro-arousal and therefore disturbance to control by the cerebral nerve centres.

The mandibular movement may also continue at the respiration rate during sleep even if there is no longer movement of the thorax of the abdomen, that is to say even if the diaphragm muscle that actions the expansion of the thorax and of the abdomen during inspiration controlled by the spinal nerves is no longer functional or has stopped. The mandibular movement may then be exerted in another plane, for example the horizontal plane, in the form of a front to rear or rear to front movement, i.e. in a plane other than that of the rostro-caudal traction whereby the tracheal tug would be affected.

There can be seen in the first stream supplied by the accelerometer, likewise the second stream supplied by the gyroscope, the tonico-phasic movement at the respiration frequency of the mandibular position that is upward i.e. in a direction opposite that which the traction produced by the tracheal tug would exert. This upward and also forward movement is respectively produced by the anterior temporal and masseter muscles and by the contraction of the pterygoid muscles, and in particular by the upper muscle group.

When the respiratory effort commences and when the amplitude of the mandibular movement will increase because of the increased central respiratory control, the direction imposed on the mandibular movement may then also lie in a plane other than the vertical plane that was the plane of the tug. This is owing to the action of certain muscle groups that are recruited more than others, such as for example the pterygoid groups that are recruited more than the subhyoid groups. The movement at the respiratory frequency may occur in a more horizontal direction that will be captured by the inertial unit. The inertial unit comprises the accelerometer and the gyroscope. In fact, if the effort is monitored only in the vertical plane, periods of effort could escape signal analysis. The movement can also occur predominantly in one direction (vertical or horizontal) rather than in another.

The shape of the respiratory movement, in particular its acceleration slope, changes as a function of the muscle groups recruited. During a vertical movement, when the masseters are active, the direction of the movement during inhalation is upward, in a direction opposite that observed when the antagonist, lowering muscles dominate, and cause the decrease in movement, and this situation can generate a change in the movement waveform.

This analysis of the streams supplied by the sensing unit enables verification of the fact that the movement of the mandible during inhalation is downwards when the activity of the lowering muscles dominates and upwards when the activity of the lifting muscles dominates. This information is obtained via analysis of captured changes of speed and acceleration. This makes it possible to assess the level and the nature of the response that the subject develops to parry the respiratory event that is unwinding and the greater or lesser recruitment of the muscles lifting the mandible tasked with stabilizing the upper respiratory tracts.

Example 4

Figure 4:
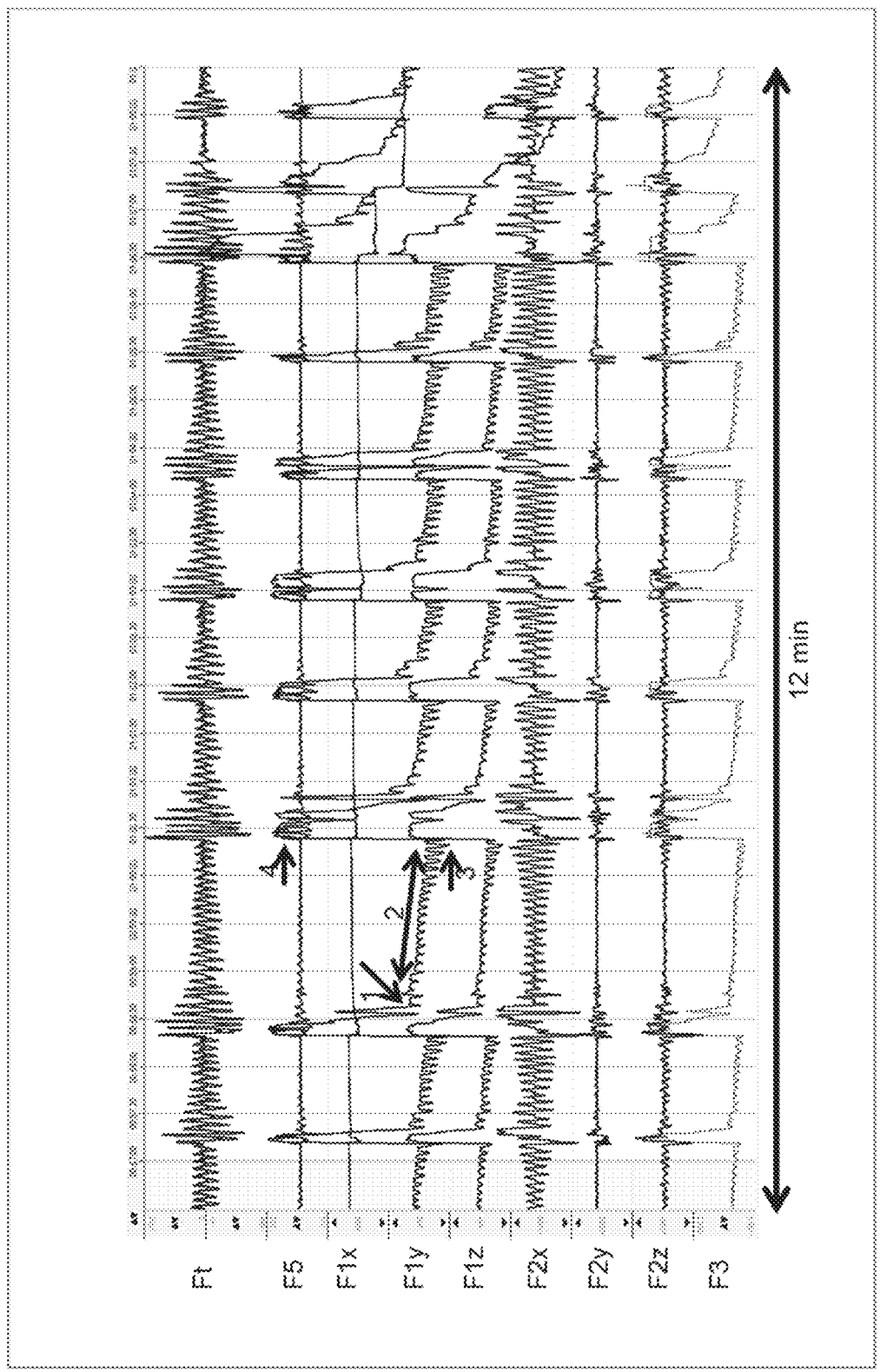
FIG. 4 shows the loop gain.

In a fourth example, reference is made to FIG. 4.

The stream observed refers to the identification of four characteristics that describe the behaviour of the mandible during the event. These characteristics are going to make it possible to understand how, for the subject, in a particular stage of sleep and for a particular position of the head, the respiratory event is going to be constructed and how the brain is going to respond to attempt to free itself. Above and beyond the description of the progress of the event, it is possible to identify information as to its risk of recidivism, both in the short term and in the longer term. These characteristics have a predictive value, such as for example, when the value of the amplitude of the response relative to the disturbance, termed the loop gain, is high, i.e. the response to the disturbance is high. FIG. 4 shows the loop gain. In this figure the arrow 1 marks the point of collapsibility on the stream F1, that is to say a solution where there is no longer exercise of cerebral control so that the mandible falls passively under the effect of local anatomic constraints such as its weight determined for example by the obesity of the subject. The arrow 2 shows a movement of the mandible that is moreover also seen at the same time in the stream 2. The peak-to-peak amplitude of the movement of the mandible, at the beginning of the arrow 2, is low. Then, thereafter, while the mouth is going to open, the mandible is going to be lowered, which can be seen at the level of the stream 1 which is lowered, the peak-to-peak amplitude is going to increase. The level of the stream 1 will then reach a level indicated 3 that corresponds to the arousability point which, in turn, will be followed by a much greater amplitude peak indicated by the arrow 4. This movement of large amplitude enables measurement of the loop gain that is accompanied by closing the mouth as shown by the peaks in the streams F1 and F2 as well as the highest value that the stream 1 will then reach although the mouth has closed again in the meantime. The loop gain indicates the response to the disturbance. It is calculated as the ratio of the differences between the noteworthy points indicated by the arrows 4 and 3 to the numerator and the arrows 3 and 1 to the denominator.

There is a high risk of seeing the events repeat in a self-sustaining manner, in particular in a central form, of short apnoeas. Assessing the muscular, in particular phasic, gain of the upper respiratory tracts enables prediction of the duration of the event. A low muscular gain signifies that the event risks lasting longer than when the gain is high. The point of arousability, which is the lowest point of the mandibular position just before the activation that terminates the event, also enables prediction of the duration of the event. If the position is not much lowered, there is a risk of the event repeating, sometimes cyclically. The effect of anatomical constraints, such as those linked to weight and to local accumulation of fatty tissue in the upper respiratory tracts, may also be determined at the time of the mandibular drop immediately after a micro-arousal or an arousal when the centres are still siderated by the latter, in particular by calculating the position of the mandible on the basis of the values measured by the accelerometer (collapsibility point).

Example 5

Figure 5:
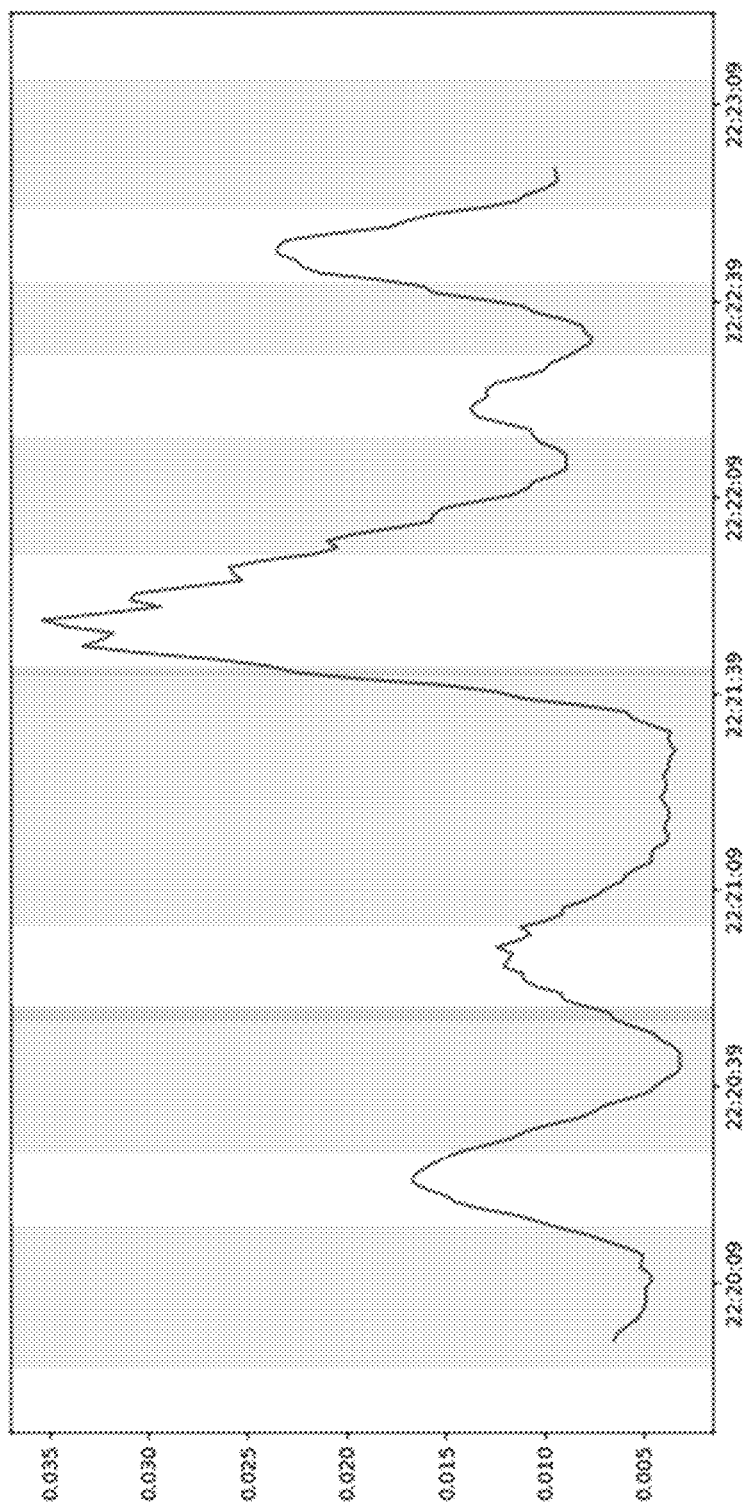
FIG. 5 shows the identification of micro-arousals following preprocessing.
Figure 6:
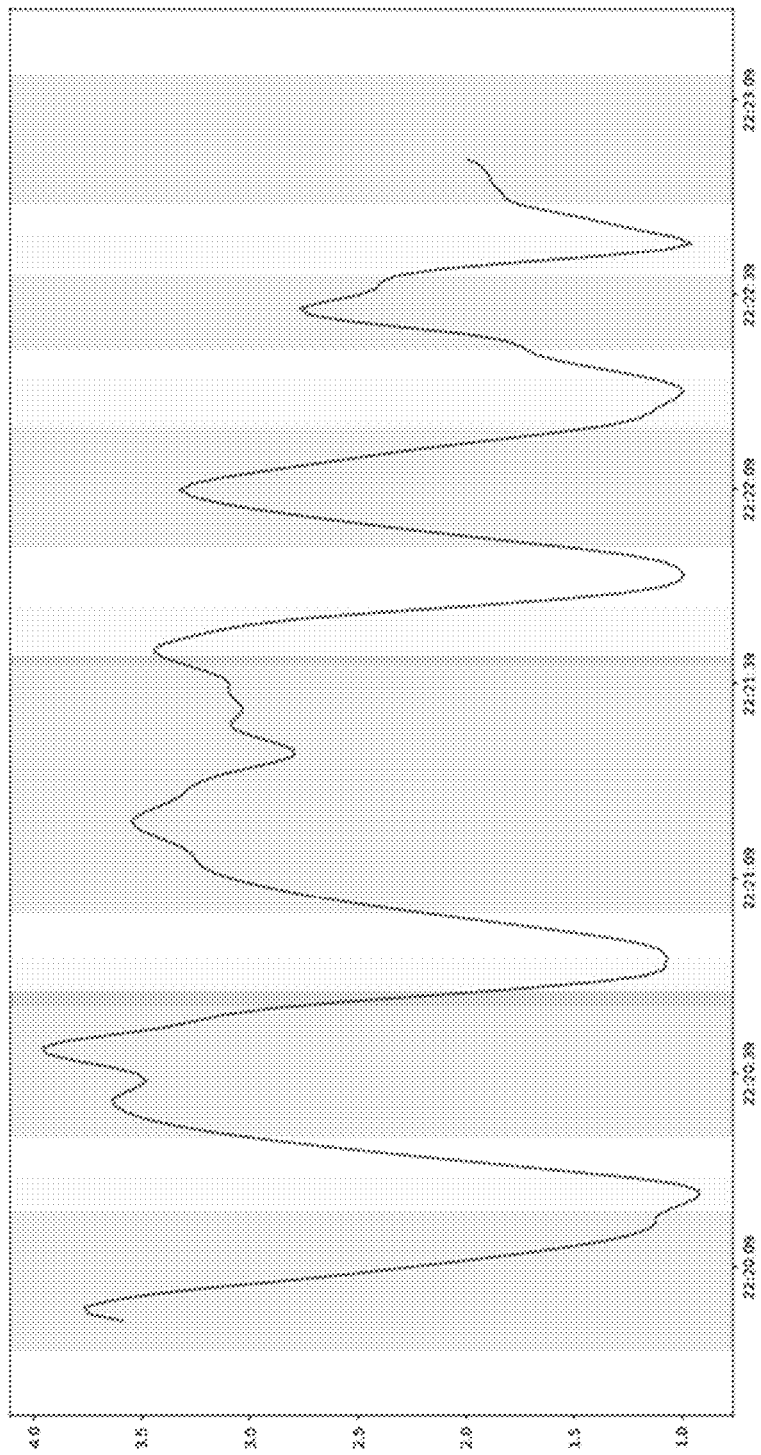
FIG. 6 shows the measured signal after application of band-pass filtering.

In a fifth example, reference is made to FIGS. 5 and 6.

The stream of measurement signals produced by the sensing unit may include noise affecting the measured signal and it may prove useful to preprocess the stream when received by the device. The principle of this preprocessing is simply to produce an enhanced signal. Analysis by the person skilled in the art has made it possible to know that during a period with an augmented cerebral control state the position of the mandible and therefore its speed and its acceleration periodically vary about the same value at a frequency of the same order as the respiratory frequency, that is to say between 0.15 Hz and 0.60 Hz. It is possible to isolate signals concerning micro-arousals by retaining only the lower frequencies of the band of respiratory frequencies, for example by low-pass filtering of the measurement signals from the accelerometer and the gyroscope. FIG. 5 shows that, by applying this preprocessing, the micro-arousals, representing an activation, are siderated relative to periods with an augmented cerebral control state. A clear peak is seen in the signal on the occasion of each micro-arousal. Application of this preprocessing is made possible, for example, by the application of a sixth order Butterworth filter, well known in the field of digital signal processing.

Conversely, it is possible to set aside periods with an augmented cerebral control state by filtering one of the captured signals with the aid of a band-pass filter corresponding to the respiratory frequency band. The result of applying this kind of filter to the signal from the gyroscope is shown in FIG. 6. It is seen there that the value of the signal is higher during periods of effort.

The characteristics used to identify information in the stream of measurement signals are for example:

Position of the head and of the mandible (roll, pitch, yaw angles for example)

Acceleration of the mandible and of the head along each axis

Speed of rotation of the mandible and of the head along each axis

Norm of the rotation speed of the mandible and of the head about one or more axes (in space, if the vector u has coordinates (x, y, z), its norm is written: $(x^2+y^2+z^2)^{0.5}$)

Norm of the acceleration of the mandible and of the head along one or more axes

Median of the values measured over 10 or 30 seconds or defined by two activations Mean of the values measured over 10 or 30 seconds or defined by two activations Maximum of the values measured over 10 or 30 seconds or defined by two activations Minimum of the values measured over 10 or 30 seconds or defined by two activations Standard deviation of the values measured over 10 or 30 seconds or defined by two activations Exponential mobile mean of the measured values (with a half-life of 5, 60, 120 and 180 seconds)

Fourier transformation and integration across all frequencies, over the respiratory frequency band (0.15-0.60 Hz), over the low frequency band (0-0.10 Hz) of the measured values Fourier transformation and identification of the energy maximum frequency or the second energy maximum frequency of the measured values Shannon entropy over a 90 second window of the measured values Time offset of the rotation speed and acceleration signals of the mandible and of the head and of the other characteristics in order to take into account the past and the future.

It is equally possible to combine the above methods with one another.

When the characteristics have been identified in the streams of measurement signals, the analysis unit can proceed to analyze them. To this end, it will for example use artificial intelligence calling on random forest type algorithms. The features extracted in this way from a whole series of signal fragments the polysomnography results of which are known are injected, in parallel with expected results, into an algorithm in order to produce a model that will enable pattern recognition type classification of new fragments.

The signal pattern is a specific state of a signal sequence, which may be visible physically or mathematically via parameters. Pattern recognition is a process for identifying (classifying) a specific pattern in the signal with the aid of an automatic learning algorithm based on information already acquired or statistical parameters extracted from this signal.

Deep learning is an automatic machine learning technique that involves models inspired by the structure of the human brain, termed artificial neural networks. These networks are made up of multiple layers of neurons that enable extraction of information in the data and production of the result. This technique is very effective for unstructured types of data, for example an image, a sequence or biological signals.

Automatic learning (or statistical learning) is an area of artificial intelligence the objective of which is to apply statistical modelling methods that give the machine (computer) the capacity to learn information from data in order to improve the performance thereof in solving tasks without being explicitly programmed for each of them.

Artificial intelligence (AI) is the set of technologies aimed at enabling machines to simulate intellectual activities.

The development of these models may for example proceed as follows:

1) Two hundred subjects are equipped with the sensing unit at the same time as they undergo the reference clinical examination in the field of sleep: polysomnography.
2) The signals captured from forty of these subjects are then used to train each random forest model. The signals from the sensing unit and a subset of the characteristics obtained after the preprocessing step are injected conjointly with the reference results of the examination of sleep in the random forest algorithm and classification models are generated on the basis of this input data.
3) The remainder of the subjects are then used in order to validate the model: the signals from the sensing unit corresponding to these subjects are injected into the model generated in the preceding step, generating in turn results, and those results are compared to the results obtained by way of polysomnography. When the agreement between the results obtained by means of the models and by polysomnography is deemed sufficient, the models are considered valid. Otherwise, development resumes from step 2 of this section.

In order to be able to reliably identify disturbances that occur during the sleep of a subject it preferred to be able to observe that the subject has actually entered the sleep phase. When it has been detected that the subject is actually in the sleep phase, it will then also be possible to establish the subject's sleep stage in order to be able to interpret correctly the signals present in the streams of measurement signals. On entering sleep, the mandible will assume a respiratory frequency between for example 0.15 Hz and 0.60 Hz. That respiratory frequency must be present for a plurality of tens of seconds at a stretch in order to be able to affirm a stable sleep state.

Example 6

In a sixth example, various sleep stages of a subject are discussed. In particular, table 1 (included below, after the examples) shows the various sleep stages of a subject and their relation with movement of the mandible and movement and the position of the head of the subject. What essentially characterizes a wakening state is that in that state the mandible moves unpredictably, whereas in a subject a sleep state is characterized, with no sleep disturbance, by the mandible effecting a movement of rotation at a frequency which is that of respiration. To detect a waking state, respectively a sleeping state, the analysis unit will preferably function using an analysis window of 30 seconds and pre-processing of the first and second streams using a band-pass filter and/or an exponential mobile mean. To extract the profile that characterizes a waking state, respectively a sleeping state, a level of the normalized mean will for example be taken into account. That level is in fact higher in a waking state than in a sleeping state.

Also distinguished in sleep are N1, N2, N3 and REM (Rapid Eye Movement) stages. During the N1 sleep stage there is seen a variation of the movement of the mandible at the respiratory frequency with a peak-to-peak amplitude variability for a period often limited to a few minutes in the adult. The position of the head generally remains stable, but that of the mandible remains unpredictable, or may change periodically. To detect an N1 sleep stage using the processing device an analysis window of 30 seconds is preferably used in order to ensure continuity of movement. Pre-processing the first and second streams by calculating the entropy of the frequency of the signals may be used. The level of the normalized mean will be taken into account in a first approach as a profile that characterizes this N1 sleep stage, but other approaches may be used to improve analysis accuracy. In an N1 stage the level of the normalized mean will be higher than in N2 or N3 stages.

The analysis unit is adapted to verify if during a second time period, in particular a period of 30 seconds, said normalized mean and a variance of the amplitude and of the frequency of the first and second streams received have a level that characterizes an N1 sleep state. The analysis unit is adapted to produce a second data item indicating an N1 sleep state if said normalized mean and the variance of the amplitude and of the frequency of the first and second streams received have a level that characterizes a sleep state N1.

During the N2 and N3 sleep stages, the variation of cerebral control amplitude and/or frequency is increasingly low from N2 to N3. There will therefore be virtually no movement of the mandible or of the head at these stages in a normal subject. To detect an N2 or N3 sleep stage with the aid of the processing device an analysis window of 30 seconds will preferably be used in order to ensure continuity of movement. Pre-processing with the aid of a low-pass or band-pass filter will also preferably be used. The level of the normalized mean will be taken into account in a first approach as a profile for characterizing this N2 sleep stage. In an N2, respectively N3, stage the level of the normalized mean will be less and less high. The level of the normalized median may also be used to identify the N2 or N3 stages or other statistical measuring techniques.

The analysis unit is adapted to verify if during a second time period, in particular a period of 30 seconds, said normalized mean and/or a normalized median of the first and second streams received has or have a level that characterizes an N2 sleep state, respectively an N3 sleep state. The analysis unit is adapted to produce a fourth, respectively fifth, data item indicating an N2 sleep state, respectively an N3 sleep state, if said normalized mean and/or a normalized median for example of the first and second streams received has a level that characterizes an N2 sleep state, respectively an N3 sleep state.

In the human being an REM stage is characterized by unpredictable movements of the mandible. To detect this kind of stage with the aid of the processing device an analysis window of 30 seconds will preferably be used in order to ensure continuity of movement. In adults, this type of movement of unpredictable frequency and/or amplitude often lasts longer in REM than in the N1 stage. The periods of such movement during an N1 stage are often limited to a few minutes. The direction of movement of the mandible position during cerebral activation is often negative, because the mouth opens. In the REM stage there is seen a variation of the movement of the mandible at the respiratory frequency with a variability of the peak-to-peak amplitude that is not periodic. The position of the head generally remains unchanged during the REM stage. Detection is effected in an analogous manner to that for the N1 period and the aim is to observe the respiratory instability of the movement of the mandible. The REM stage is often entered without cortical activation that the EEG could capture and with no movement of the head. The accelerometer will therefore not measure anything, whereas the gyroscope will observe changes in rotation of the mandible. This shows the importance of having both the signal from the gyroscope and that from the accelerometer in order to correctly observe entry into the REM phase. Exit from the REM phase often goes hand in hand with cerebral activation that will be observed by the accelerometer and the gyroscope, which will observe an isolated mandibular movement (IMM) and where applicable a movement of the head. The level of the normalized mean may be taken into account as a first approach. The variance of the amplitude and of the frequency will also be looked for, for example. Detection of REM during the first fifteen minutes of sleep enables a diagnosis of narcolepsy.

Example 7

Figure 14:
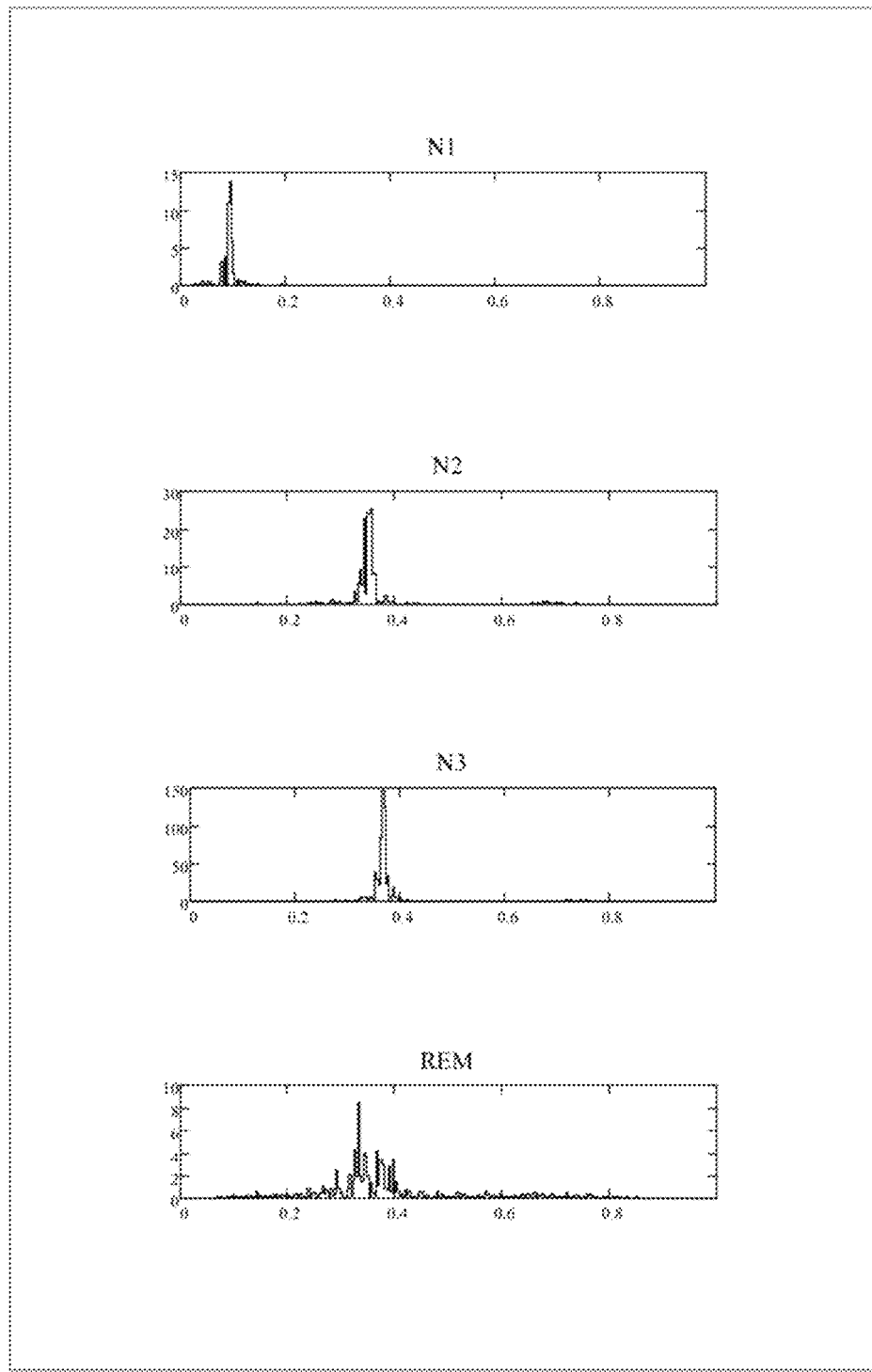
FIG. 14 shows spectrograms of the frequency distribution of the mandibular movement.

In a seventh example, reference is made to FIG. 14.

Comparative analysis throughout sleep for example of the variance of the values of amplitude and/or of frequency of movement of the mandible and/or other statistical characteristics of the signal, in isolation or grouped into an array to which a classifier, for example of random forest type, is applied to practice statistical inference, enables different stages to be distinguished. To this end, FIG. 14 shows spectrograms of the distribution of the mandibular movement frequencies for differentiating the stages. In this FIG. 14 the vertical axis represents an amplitude density and the horizontal axis a frequency. These specific characteristics of each sleep stage can also be identified by machine deep learning. This algorithmic and/or statistical approach may also be used for the characterization of respiratory events and non-respiratory motor events.

The table below gives an example of the variance of the amplitude level of the mandible rotation signal between the various stages of sleep. In this table, by "interval" is meant the interval between the upper level, at the $2.5^{th}$ centiles, and the lower level, at the $97.5^{th}$ centiles. By "amplitude" is meant the difference between the maximum and minimum values. The "variance" is a measurement of the spread of the values considered. The measurements are based on 1000 samples taken over a period of 30 seconds for each stage.

| Stage | Variance (mm$^2$) | Interval (mm) | Amplitude (mm) |
| --- | --- | --- | --- |
| N1 | 0.016 to 0.064 | 0.378 to 0.945 | 0.470 to 1.070 |
| N2 | 0.018 to 0.052 | 0.465 to 0.795 | 0.560 to 0.990 |
| N3 | 0.081 to 0.143 | 0.899 to 1.245 | 1.020 to 1.330 |
| REM | 0.004 to 0.098 | 0.250 to 1.370 | 0.320 to 1.580 |

The analysis unit being adapted to verify if during a second time period, in particular a period of 30 seconds, said normalized mean and a variance of the amplitude and of the frequency of the first and second streams received have a level that characterizes an REM sleep state, said analysis unit being adapted to produce a third data item indicating an REM sleep state if said normalized mean and the variance of the amplitude and of the frequency of the first and second streams received have a level that characterizes an REM sleep state.

The identifying unit is adapted to identify in the first and second streams movement signals that characterize a rotation of the mandible and/or a movement of the head of the subject. The analysis unit is adapted to analyse these signals, for example by applying to these movement signals a band-pass filter and an exponential mobile mean or a measurement of the entropy of the frequency of the signals. By applying this band-pass filter, for example to respiratory frequencies, and this exponential mobile mean, with for example a half-life equal to 5, 60, 120 or 180 seconds, to the first and second streams of signals supplied and with a first observation time period of 30 seconds, the analysis unit will be able to observe if the signal is unstable. If this is the case an arousal situation will be observed. If on the other hand the signal is stable a sleep situation could be observed.

The analysis unit is adapted to apply as a profile that characterizes a sleep state said exponential mobile mean over a second time period of the first and second streams situated between 30 seconds and 15 minutes, in particular 3 minutes. For some analyses the second time period could even be 30 minutes. The analysis unit is adapted to verify whether or not during said second time period said exponential mobile mean has a substantially constant value and to produce a first data item that indicates a sleeping state, respectively a waking state, if said value is substantially constant, respectively not constant.

The identifying unit is adapted to identify in the first and second streams movement signals that characterize a rotation of the mandible and of the head of the subject. The analysis unit is adapted to calculate the entropy on the frequencies of these movement signals. By applying this entropy function, with for example an analysis window of 90 seconds, to the first and second streams of signals supplied and with an observation time period of 30 seconds, the analysis unit could then observe the level of the normalized mean. If the level is high, an N1 or REM sleep situation will be observed as a function of the value of the level.

The identifying unit is adapted to identify in the first and second streams movement signals that characterize a rotation of the mandible and/or a movement of the head of the subject. The analysis unit is adapted to apply to these movement signals a band-pass filter or a low-pass filter. By applying this band-pass filter for example at respiratory frequencies or this low-pass filter (below 0.10 Hz for example) to the first and second streams of signals supplied and with an observation time period of 30 seconds, the analysis unit will be able to observe the level of the normalized mean and/or of the median. As a function of the level an N2 or N3 sleep situation will be observed.

Cerebral activations in the form of a micro-arousal have a duration between 3 and 15 seconds inclusive and may be of cortical or sub-cortical type. Cerebral activations that lead to arousal last more than fifteen seconds. Cortical cerebral activations in REM sleep may have by way of characteristics repeated lowering of the mandible. In the case of cortical activations, a corticobulbar reflex is activated and a plurality of sudden movements of great amplitude or even of great duration of the mandible is observed. The reflex amplifies the movements. In the case of sub-cortical activations, this reflex is not activated, and it is then possible to observe only one sudden movement of lesser amplitude with a frequency discontinuity relative to the respiratory frequency at which the mandible was actioned. This movement may be of much lower amplitude and shorter duration than when the corticobulbar reflex is activated. The movement is therefore often less marked and identifying it may be assisted by the detection of a concomitant movement of the head that may be exerted over only a very short distance.

Example 8

In a further example, reference is made to table 2. Table 2 shows cortical and sub-cortical cerebral activation characteristic. A consequence of cortical activation will be abrupt closing or opening of great amplitude of the mandible for a duration situated between 3 and 15 seconds. If this cortical activation occurs during sleep, it will generally be accompanied by a change of position of the head of the subject. The analysis unit will analyse the amplitude and the duration of the movements over a window of ten seconds using the first and second data streams.

Sub-cortical activation is characterized by a discontinuity in the frequency of variation of the movement of the mandible and in the shape thereof. The mandible will most often remain stable. The analysis unit will analyse the amplitude and the duration of the movements over a window of ten seconds using the first and second data streams. The analysis may equally be carried out on a continuous variable.

The analysis unit will therefore verify if during a third time period, in particular a period situated between 3 and 15 seconds, an amplitude of the signals of the first and second streams received has a level that characterizes cortical, respectively sub-cortical, activity. The analysis unit is adapted to produce a sixth data item indicating cortical, respectively sub-cortical, activity if said amplitude of the first and second streams received has a level that characterizes cortical, respectively sub-cortical, activity.

To detect the presence of a respiratory event or a non-respiratory motor event, the analysis unit will analyze the evolution of the position of the mandible, the amplitude of the peak-to-peak mandibular movement, the variance of the peak-to-peak amplitude of the mandibular movement that indicates a variation of the cerebral control amplitude and the frequency of the mandibular movement. If a low amplitude is observed, that is to say an amplitude corresponding to the amplitude observed during the eupnic respiratory movement, and in the presence of stable centrality (mandibular movement occurring around a continuous and stable degree of opening of the mouth), there are no events to be taken into account for sleep disturbances.

If a high respiratory control amplitude, for example an amplitude corresponding to movements exceeding 0.3 mm, is observed, that is to say a change of amplitude greater than the change of amplitude observed during the eupnic movement, there is deduced an increased motor or respiratory effort that may indicate sleep disturbances.

If a large respiratory control amplitude decrease is observed, that is to say one that is low, for example of the order of 0.1 mm, or zero, with stable or unstable control centrality, for at least 10 seconds or two respiratory cycles for example, there is deduced a central type respiratory event.

Measuring the gain of the muscular response of the upper respiratory tracts during the event enables determination of its obstructive character, that is to say marked respiratory effort, as against its central character with no respiratory effort or with a reducing respiratory effort ending up below the level considered to be normal. This analysis enables characterization of apnoea and hypopnoea as obstructive or central. The level of normality of the respiratory effort is determined beforehand during periods of normal respiration during sleep, for each stage of sleep.

The change of position of the head can modify the configuration of the event with or without change of sleep stage or of transition between sleeping and waking. The gain of the muscular response during the event is calculated by measuring the peak-to-peak amplitude change during phasic mandibular movement at the respiratory frequency during the event. It is the measurement of the peak-to-peak amplitude difference between the start and the end of the period of the event during its phasic movement that can already be calculated from a single respiratory cycle, which supplies the gain value. The change may be minimal, of the order of 1/10 millimetre, or even less, but can reach 3 centimetres. The change may be accompanied by a change in the absolute position of the mandible, meaning that the mouth is more or less open when its phasic displacement is exerted. The change can occur in any direction between the horizontal and the vertical, taking into account the position of the head during sleep.

Example 9

In a ninth example, reference is made to table 3. Table 3 illustrates a typical behaviour of cerebral control for the detection of respiratory events and non-respiratory motor events. It can be seen that to detect an obstructive apnoea-hypopnea, the analysis unit will for example use a median and/or a mean value on the first and second flow of measurement signals. An observation time of at least two breathing cycles or 10 seconds will be preferred to make the analysis more reliable. Obstructive apnoea-hypopnea is characterized by large cerebral control amplitude at the respiratory rate that can be repeated cyclically or non-cyclically. It will end with a large mandibular movement during cerebral activation. In particular, the distribution of the amplitude values of the mandibular movement in the stream under consideration will be analyzed.

To detect breathing effort linked to arousal (RERA), the unit of analysis will proceed in the same way as described in the previous paragraph. To detect a central apnoea-hypopnea the duration of observation will also be at least two breathing cycles or 10 seconds.

Example 10

Figure 7:
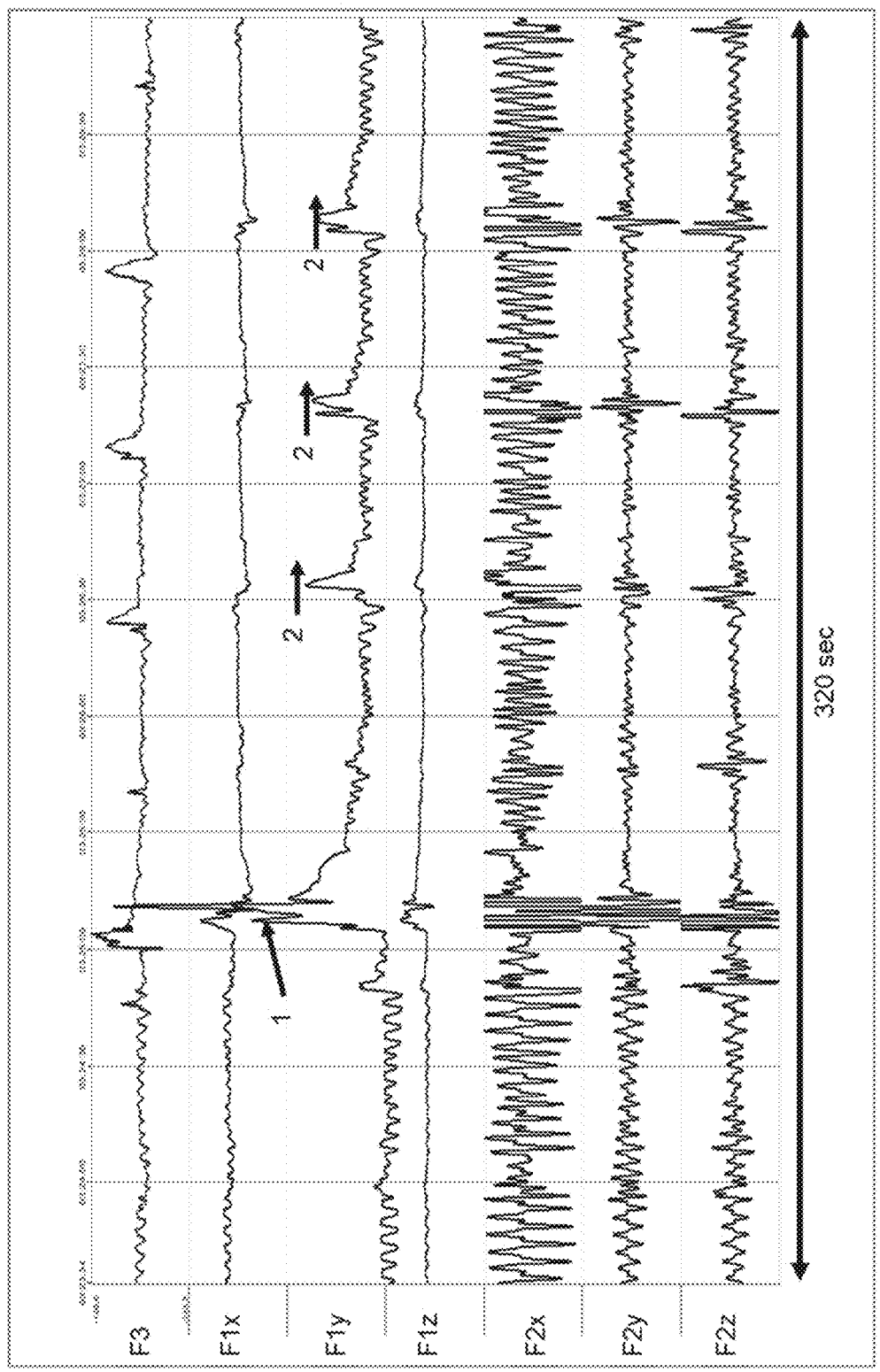
FIG. 7 shows a signal indicating micro-arousals.

In a tenth example, reference is made to FIGS. 4 and 7.

A situation of bruxism will be detected by using for example the median, mean, maximum value or other statistic of the rotation of the mandible and of its acceleration over an observation time of 30 seconds for example.

Cerebral control following cerebral activation with or without a change in the position of the head may:
  Stable and of low amplitude;
  Increase with a high or "rising" centrality; the mouth closes and the event is corrected if the latter was obstructive;
  Increase with a low or "descending" centrality; the mouth opens and the event is imposed, obstructive;
  Decrease with a low or "descending" centrality; the event is imposed, central;
  Increase with a high or "rising" centrality, when the pterygoid lateralis muscles are recruited.

If the position of the head does not change but the respiratory control level changes, the position of the mandible and the change therein continue to provide information on the respiratory control level. FIG. 7 shows a signal indicating cortical cerebral activation, plotting the movement of the mandible as measured by the accelerometer and the gyroscope. In a left to right direction in this FIG. 7 there are first seen a few oscillations indicating movement of the mandible at a regular frequency. This movement of the mandible is caused by respiration with some degree of effort. The subject concerned has to make an effort to cause air to pass through the upper respiratory tracts, which can be seen in the amplitude of the signal from the gyroscope. In particular, the reference 1 indicates a micro-arousal provoked by cortical activation. There is then seen a strong oscillation indicating a movement of greater amplitude that follows on from cerebral activation. It can then be seen that the level of the signal has increased, indicating that the mouth has closed and that the mandible has risen a few tenths of a millimetre. If the mandible rises and there is still detected a respiratory frequency of its movement with an amplitude greater than the normal value, it can be deduced that there is a persistent obstructive event as observed here. If the movement becomes of low amplitude, it may be stated that respiratory control is no longer rising beyond the normal and that the respiratory effort has been normalized. The reference 2 indicates a micro-arousal caused by sub-cortical activation producing a signal of lower amplitude than cortical activation.

The set of results obtained following processing of the signals by the analysis unit may be presented in the following manner for example:
  Hypnogram: evolution of the stages of sleep and of the moments of waking/sleeping transition during the recording;
  Start and end time of the recording, time spent in bed and/or lying down;
  Total sleeping time; various efficacy indices;
  Fragmentation of sleep, for example the number and index of micro-arousals and arousals (activations), the number and index of waking/sleeping transition changes;
  Number and index of respiratory and non-respiratory motor events;
  For example, in the event of repetition of central respiratory events with a cyclic, periodic, crescendo-descrendo variance of the cerebral control amplitude, if the duration of the period is measured as greater than 40 seconds, it is possible to suspect that the type of periodic respiration is evolving, possibly in the context of cardiac insufficiency;
  Events of a cyclic nature can also be of an obstructive kind or events of an obstructive kind can also repeat in a cyclical manner (for example when the loop gain is high and/or the arousability strong);
  Repeated sub-cortical activations isolated with respect to respiratory effort suggest association thereof with a limb movement.

The position of the head impacts on the frequency and the very nature of the respiratory and non-respiratory motor events occurring during sleep. The change of position of the head during sleep is always contemporaneous with activation from the brain. During the latter, the head will find a new position and the mandible, which has moved with a large amplitude through a plurality of repeated movements on the occasion of this change, will find a new position thereafter to be subjected again to respiratory drive the amplitude of which will be a measure of the central control level. There is therefore an association of event, as shown in FIG. 7. The central activation, the possible modification of the position of the head and the possible modification of the position of the mandible that accompanies it and active respiratory control with modification of the amplitude of the respiratory movement of the mandible are therefore integrated in the brain. The relations between activity and cerebral activation are examined. If the control activity level changes, for example via the changed peak-to-peak amplitude of the respiratory movement of the mandible, this is firstly the consequence of central activation and control state changes in the cerebral trunk. Moreover, the respiratory activity is captured by the gyroscope during rotary movement of the mandible whereas the central activation is captured by the accelerometer during linear movement of the head.

The change of position of the head and the cerebral activation that accompanies it determine the risk of the event occurring whether it be a respiratory or non-respiratory motor event by modifying the control level and therefore the type of event. A change in the position of the head is necessarily accompanied by a cerebral activation and can modify the conditions of flow of the air fluids in the respiratory tracts, in particular by modifying the upper respiratory tract calibre muscular retention state conditions in addition the fact that the new orientation assumed by the head can expose those respiratory tracts to mechanical crushing forces.

Mandibular movement and repositioning during cortical or sub-cortical activation may be described during the event as follows:

(1) The mandible is either passive, or the mandible drops on regression of activation with no tonic and/or phasic support of musculature while the central motor control is siderated for the duration of a few respiratory cycles. The relaxation of its position after the mouth closes and with passive opening of the mouth, that is to say the mandible is no longer supported, because of the loss of the tonic component of the musculature deemed to support it, over a variable distance but with a marked slope (>$^1\!/_{10}$ mm/s); the measurement of this distance between closing of the mouth and the lowest point recorded before the change of slope that will follow is a marker of the passive collapsibility of the pharynx when following on from activation there is a loss of control by the nerve centres; this situation can last for a time equivalent to a few (maximum five) respiratory cycles.

This relaxation may not take place, the mouth remaining closed or virtually closed, because there is no loss of central control (persistence of tonic component) of the musculature controlling the position of the mandible.

(2) The mandible then shows the muscular response gain, in a phasic and/or tonic form, that will reposition it at the respiratory control frequency during the event, before a new activation is triggered. There follows from this a resumption of the muscular activity controlling the position and the movement of the mandible. This resumed activity of the muscles may be manifested by a change of slope describing its new position with or without respiratory movement, that is to say with or without a phasic component, i.e. with at least one peak-to-peak amplitude measurable beyond the background noise of the measurement (>0.05 mm). This latter movement signals the resumption of respiratory movement, that is to say a shift in the respiration frequency, and therefore a respiratory effort that will make it possible to qualify the obstructive event as central or mixed, according to the rules of evaluation. The movement of the centrality makes it possible to specify if the degree of opening of the mouth is stable, increasing or decreasing, whereas the peak-to-peak amplitude of the respiratory movement reflects the current degree of effort.

(3) The centrality or amplitude point reached to be the lowest and from which the movement of closing the mouth will be executed, the first movement determined by the activation is similar to an arousability threshold. This movement is sometimes downward, for example in REM or when the mouth has not opened because the respiratory effort is above all exerted by the activity of the pterygoid lateralis and the masseter muscles that have held the mouth in the forward and high position, this movement bears witness to the activation. The latter may be cortical or sub-cortical or with a sub-cortical and then cortical sequence, or when the mandible has not opened much during the event, plausibly because of the activity of the pterygoid lateralis muscles it may then open suddenly during the activation whereas most often, as the mouth had opened during the event, the activation closes it brutally.

(4) There follows the mandibular position point at the greatest distance during activation from this arousability point, as shown in FIG. 4. The distance separating them is a measure of the amplitude of the mandibular movement during the activation. That value is measured and compared with the level of respiratory effort deployed during the event, before the activation via the change of amplitude of the respiratory movement since the beginning of the resumption of the effort up to the arousability point. The ratio of these values is a measure of a degree of mandibular loop gain.

Example 11

Figure 8:
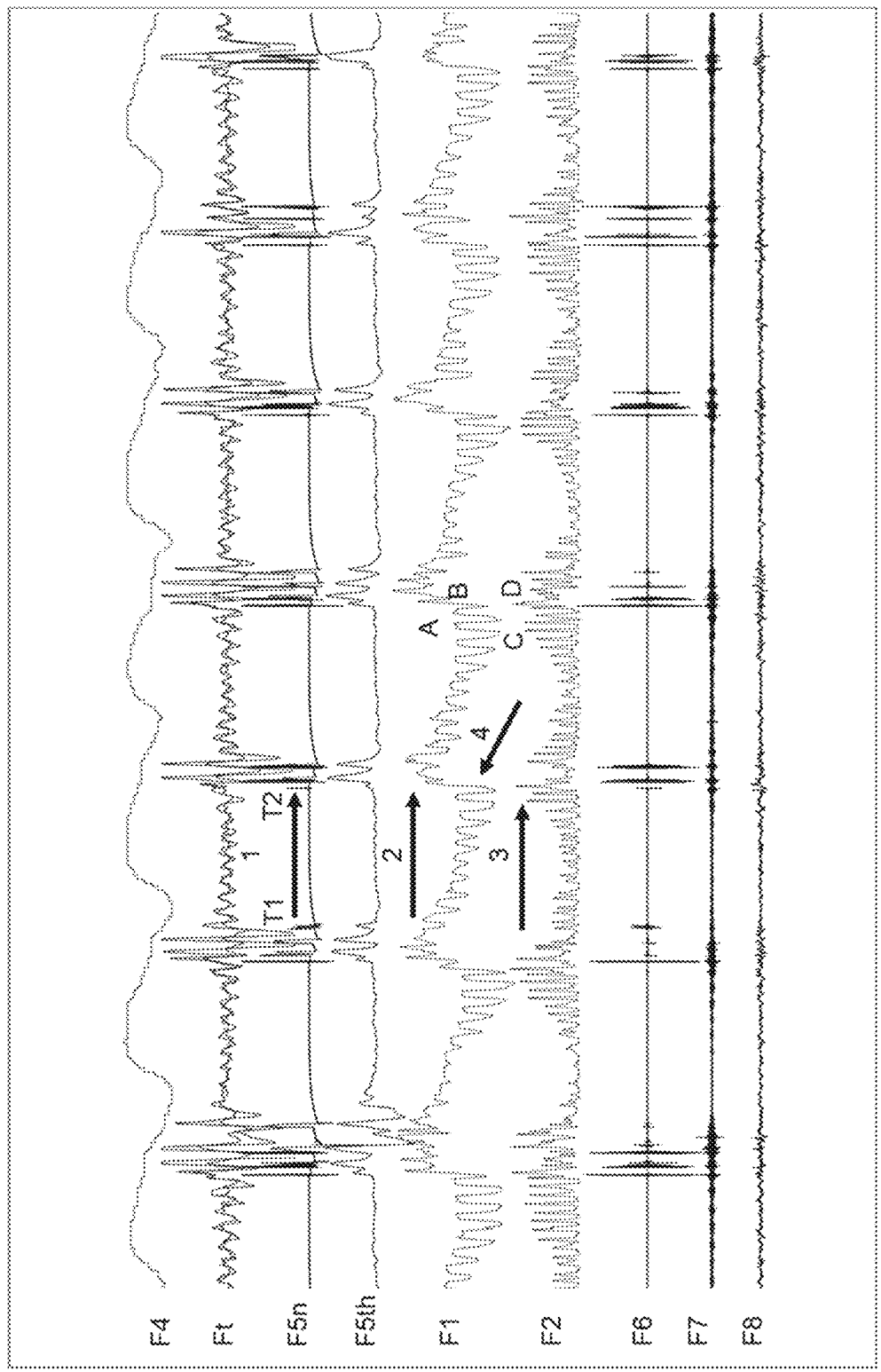
FIG. 8 shows an example of the first and second measurement signal streams in the case of obstructive apnoea.

In an eleventh example, reference is made to FIG. 8. FIG. 8 shows an example of the first measurement signal stream F1 (measured by the accelerometer) and the second measurement signal stream F2 (measured by the gyroscope) in the situation where the subject suffers an obstructive apnoea. In this figure F5$n$ designates the nasal flow and F5$th$ the oro-nasal thermal flow. It will be observed there that during the time period from T1 to T2 and following the apnoea indicated by the reference 1 the signal is not stable. At the start of this period it is seen that the signal supplied by the gyroscope is of lower amplitude than at the end of the event. Central control is intensified during the event because it is necessary to combat the obstruction causing the apnoea or hypopnoea. During this same period T1-T2 it is seen that the accelerometer (reference 2) and the gyroscope (reference 3) indicate respiratory effort followed by cerebral activation (reference 4).

Analysis of the signals shows that in the presence of obstructive apnoea between T1 and T2 there is observed on the accelerometer (F1) the movement of the mandible at the respiration frequency and with an amplitude increasing from the peak-to-peak amplitude at the same time as the mouth opens as a consequence of the position of the mandible descending more and more from one respiratory cycle to another (A). At the same time (C), it is seen that the angular speed of the rotary, respiratory movement of increasing amplitude indicates that the effort itself is increasing. Note at the height of the letter B the effect of the activation on the movement of the mandible measured with the accelerometer, which activation provokes an upward movement of the mandible and has the consequence of the mouth closing. On this occasion, the mandible will assume a new position. At the level of the letter D on the gyroscope, it is seen that this movement of closing the mouth is not purely rotary. The changes of state of the signals at the height of the letter B and of the letter D are contemporaneous with resumption of ventilation on the occasion of the cerebral activation (microarousal).

Example 12

Figure 9:
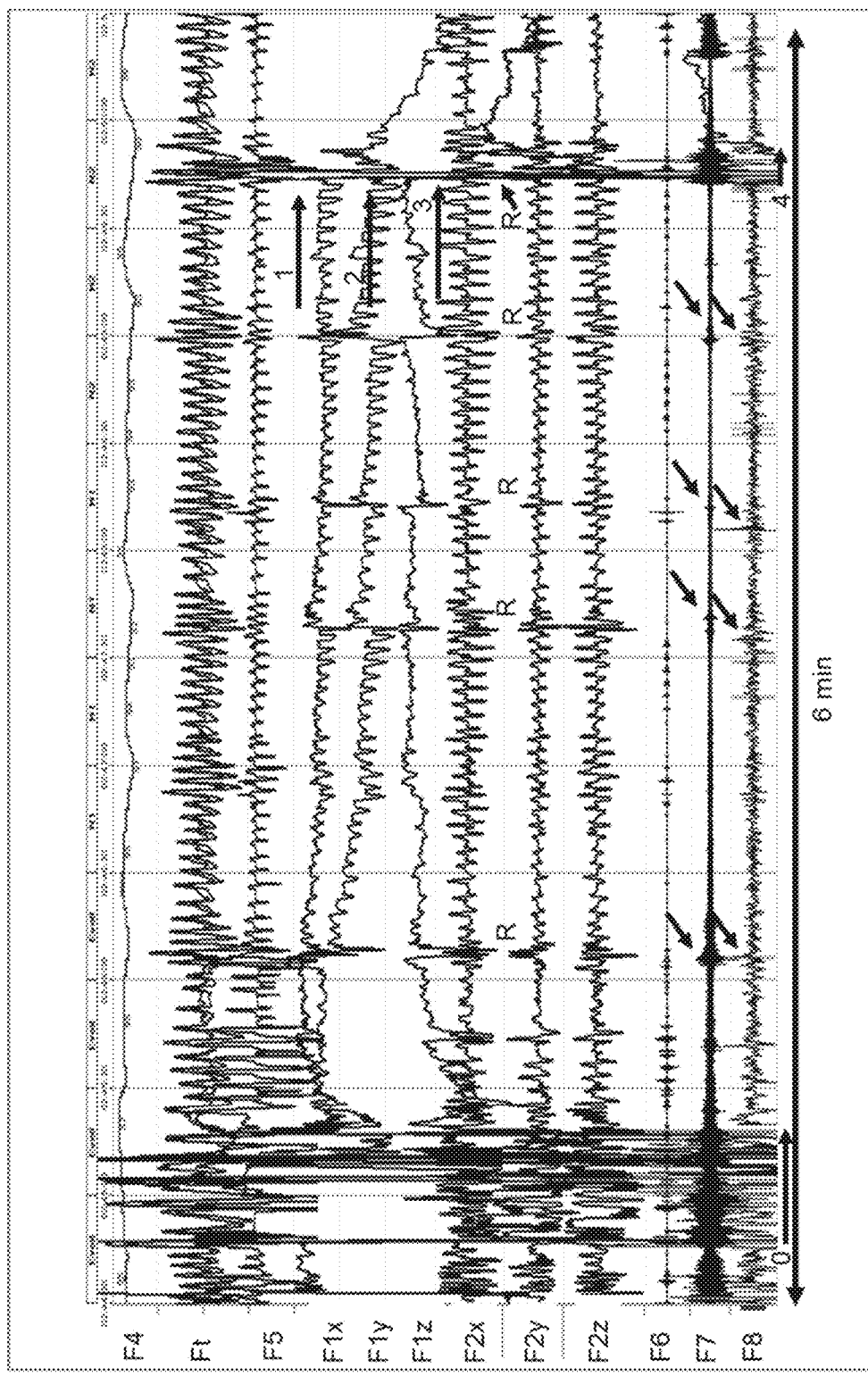
FIG. 9 shows an example of the first and second measurement signal streams in the case of obstructive hypopnoea.

In a twelfth example, reference is made to FIG. 9. FIG. 9 shows an example of the first measurement signal stream F1 and the second measurement signal stream F2 in the situation where the subject suffers an obstructive hypopnoea, indicated by the arrow 1. The arrow 0 indicates an arousal state. This same FIG. 9 also shows a sixth stream F6 captured by an audio sensor that indicates the presence of snoring, together with a seventh stream F7 sensed by a chin electromyogram and an eighth stream F8 sensed by an electroencephalogram. There is seen there a series of mandibular movements (R) of greater amplitude for a period of a few seconds which each time indicates cortical or sub-cortical activation. These movements are concomitant with changes of peaks in the streams F6, F7 and F8. In fact the electromyogram and electroencephalogram signals show clearly that there is cerebral activation on this occasion. The obstructive hypopnoea is indicated by the arrows 2 and 3, the arrow 2 indicating an effort and an opening of the mouth and the arrow 3 an effort and a rotation of the mandible. This hypopnoea is followed by an activation in the form of a micro-arousal, indicated by the arrow 4. The high value of the respiratory mandibular movement between the micro-arousals reflects a high respiratory effort that is moreover emphasized by snoring. It is therefore seen in the stream F1 coming from the accelerometer and in the stream F2 coming from the gyroscope that during snoring there is rotation of the mandible with opening of the mouth. FIG. 9 therefore shows that cerebral activity may be registered by the accelerometer and the gyroscope that measure mandibular movements as much during the period of effort at the respiration frequency as during the cerebral activation, but in this case at a frequency that is no longer typically that of respiration. Still in this FIG. 9 the digit 0 indicates an arousal state of the subject.

Example 13

Figure 10:
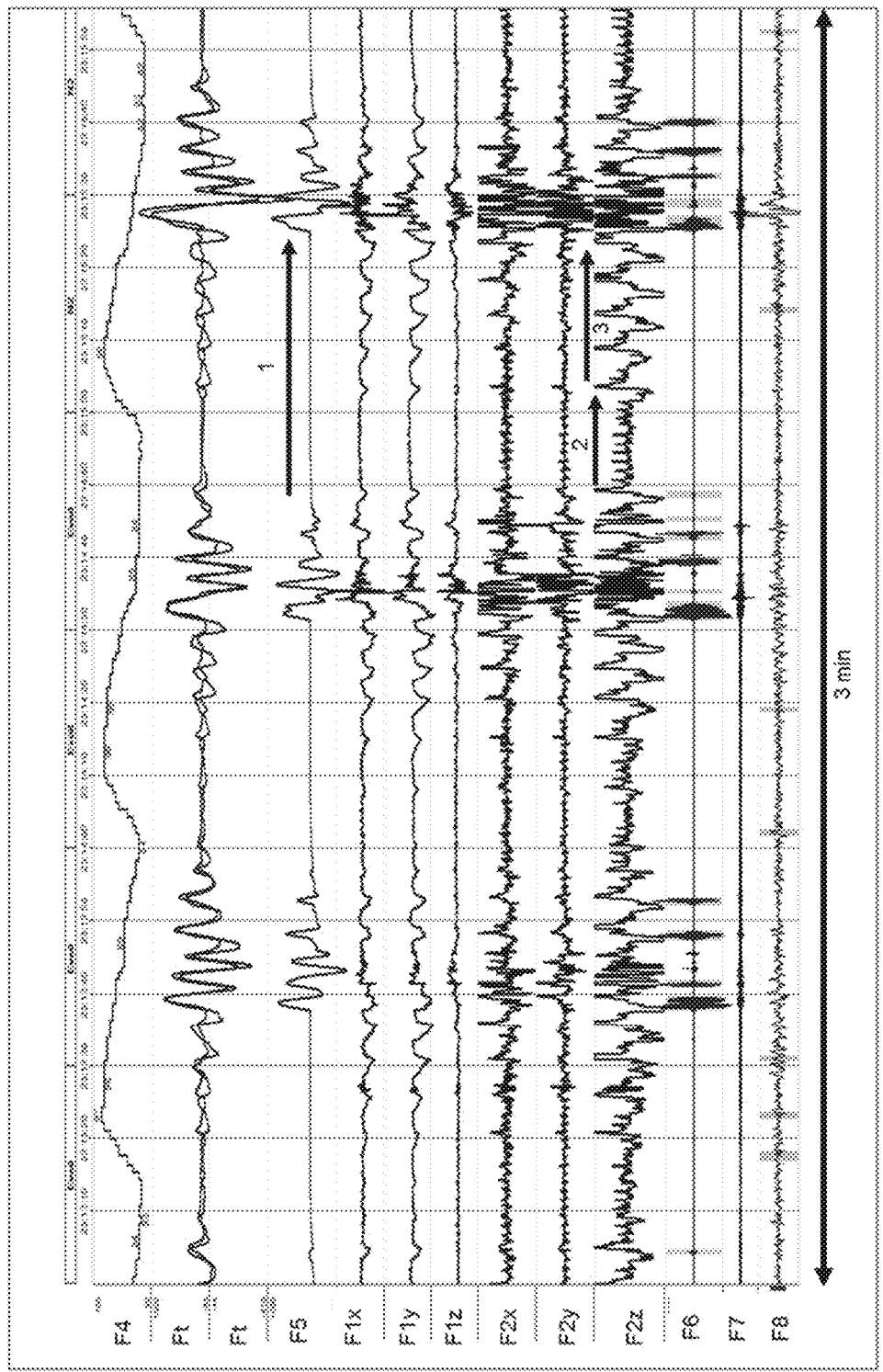
FIG. 10 shows an example of the first and second measurement signal streams in the case of mixed apnoea.

In a 13$^{th}$ example, reference is made to FIG. 10. FIG. 10 shows an example of the first measurement signal stream F1 and of the second measurement signal stream F2 in the case where the subject suffers a mixed apnoea. As in FIG. 8, there is seen in this FIG. 10 an increase in the angular speed of the mandible at a frequency corresponding to the respiration frequency. The digit 1 indicates an absence of respiratory flow that goes hand in hand with an absence of control and of effort, indicated by the digit 2, followed by restoration of cerebral control and effort, indicated by the digit 3.

Example 14

Figure 11:
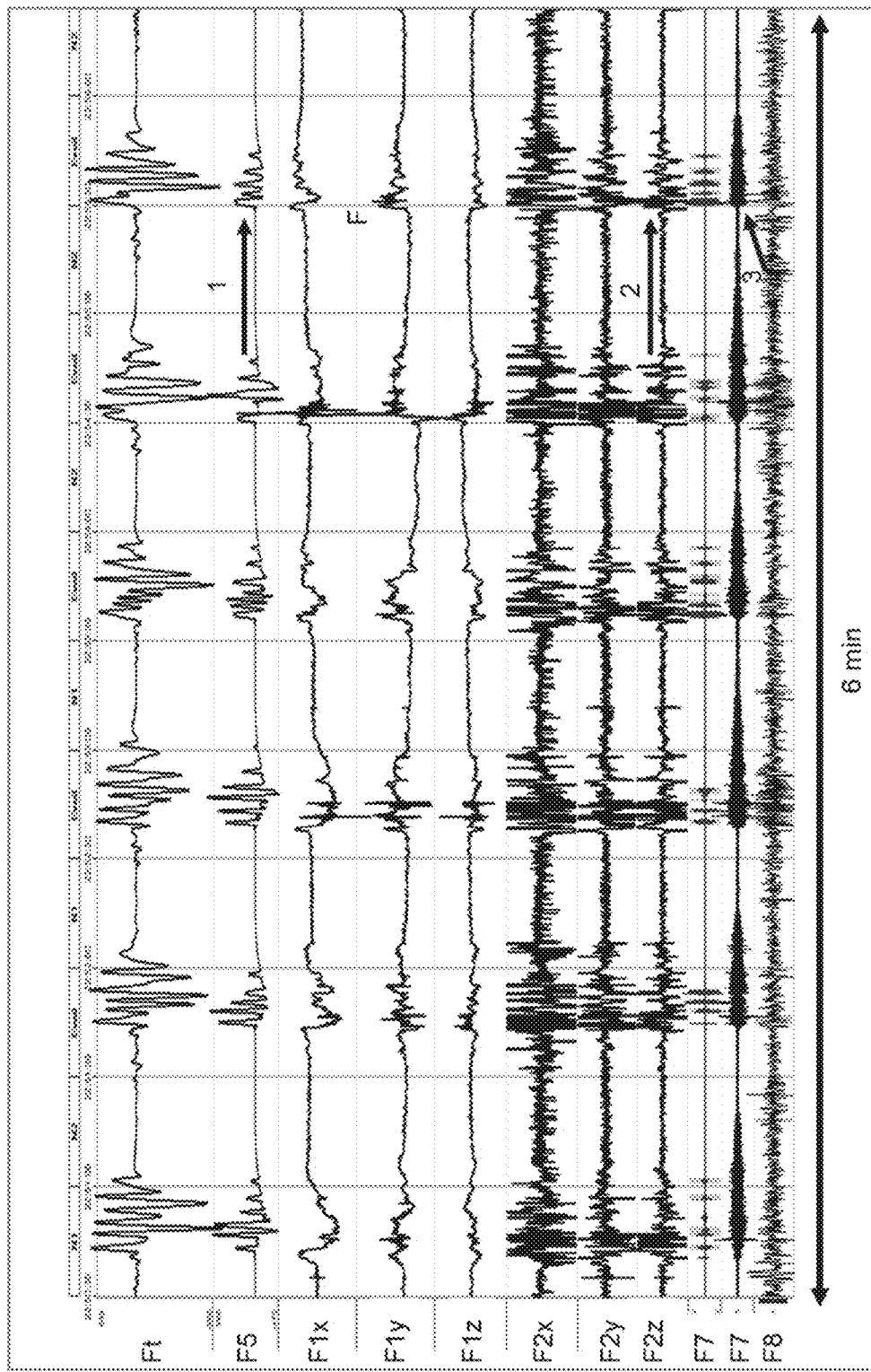
FIG. 11 shows an example of the first and second measurement signal streams in the case of central apnoea.

In a 14$^{th}$ example, reference is made to FIG. 11. FIG. 11 shows an example of the first measurement signal stream F1 and of the second measurement signal stream F2 in the situation where the subject suffers a central apnoea. The peaks F show a movement of the head and of the mandible on resumption of respiration. It is also seen that between the peaks F there is so to speak no movement of the mandible. The digit 1 indicates an absence of respiratory flow that goes hand in hand with an absence of effort, indicated by the digit 2, and activation and resumption of the effort, indicated by the digit 3.

Example 15

Figure 12:
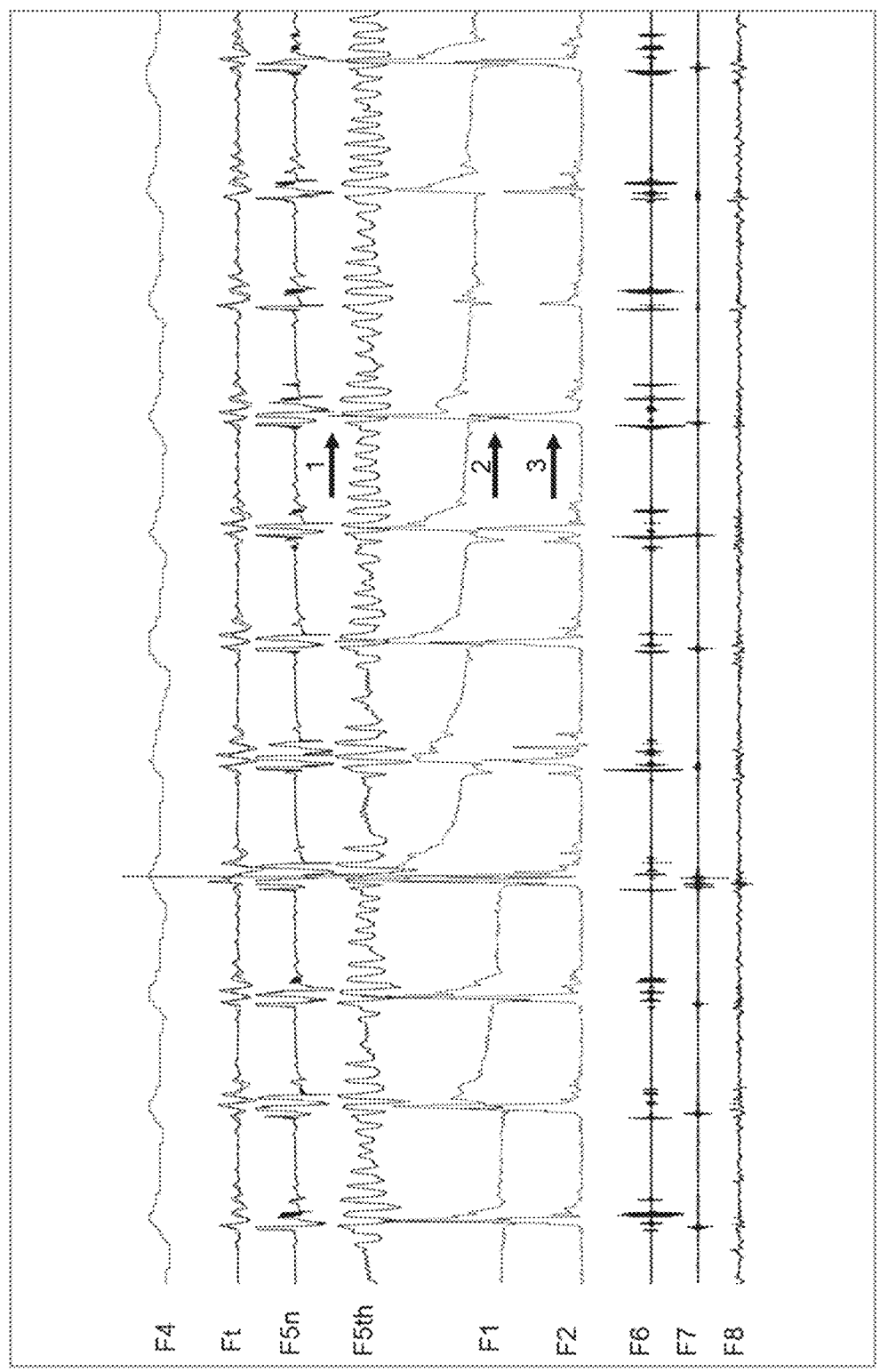
FIG. 12 shows an example of the first and second measurement signal streams in the case of central hypopnoea.
Figure 13:
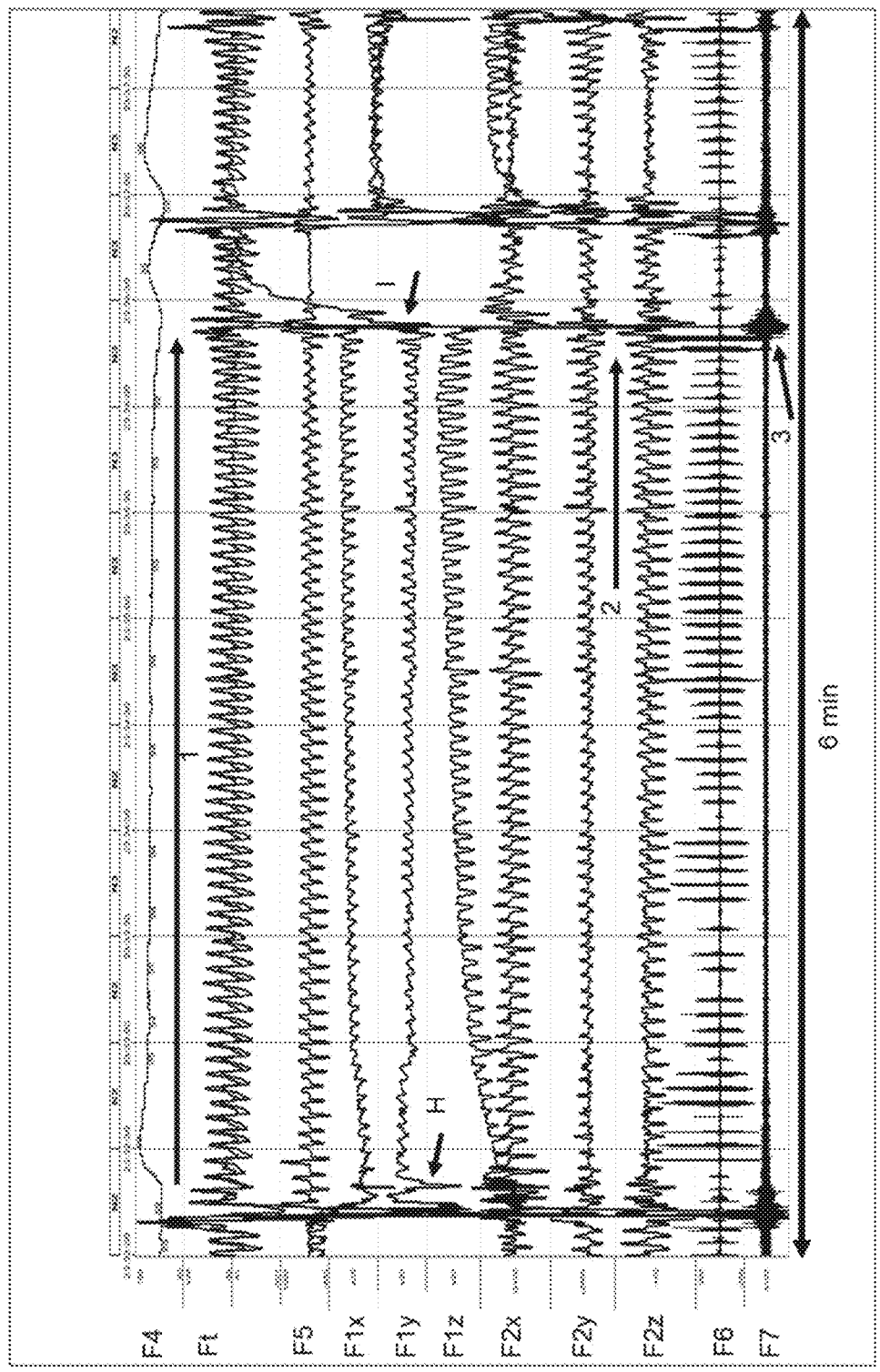
FIG. 13 shows an example of the first and third measurement signal streams during respiratory-effort related arousal (RERA)

In a 15$^{th}$ example, reference is made to FIGS. 12 and 13. FIG. 12 shows an example of the first measurement signal stream F1 and of the second measurement signal stream F2 in the situation where the subject suffers a temporary disappearance of all control of cerebral origin, which is characteristic of central hypopnoea. This disappearance is characterized by the mouth opening passively because it is no longer held up by the muscles. It is therefore seen in the streams F1 and F2 that between the peaks the signal does not indicate any activity. On the other hand at the moment of the peak there is observed a high amplitude of the movement of the mandible. Toward the end of the peaks there is seen a movement that corresponds to a non-respiratory frequency, which is the consequence of cerebral activation that will then result in a micro-arousal. The digit 1 indicates the period of hypopnoea where a reduction of the flow is clearly visible on the stream F5$th$ from the thermistor. The digits 2 and 3 indicate the disappearance of mandibular movement in the streams F1 and F2 during the period of central hypopnoea. FIG. 13 shows an example of the first measurement signal stream F1 and of the second measurement signal stream F2 in the situation where the subject experiences a prolonged respiratory effort that will terminate in cerebral activation. It is seen that the signal from the accelerometer F1 indicates at the location indicated by H a large movement of the head and of the mandible. Thereafter the stream F2 remains virtually constant whereas in that F1 from the accelerometer the level drops, which shows that there is in any event a movement of the mandible, which is slowly lowered. There then follows a high peak I that is a consequence of a change in the position of the head during the activation that terminates the period of effort. The digit 1 indicates this long period of effort marked by snoring. It is seen, as indicated by the digit 2, that the effort is increasing with time. This effort terminates, as indicated by the digit 3, in cerebral activation that results in movements of the head and the mandible, indicated by the letter I.

The analysis unit holds in its memory models of these various signals that are the result of processing employing artificial intelligence as described hereinbefore. The analysis unit will process these streams using those results to produce a report on the analysis of those results.

It was found that the accelerometer is particularly suitable for measuring movements of the head whereas the gyroscope, which measures rotation movements, was found to be particularly suitable for measuring rotation movements of the mandible. Thus cerebral activation that leads to rotation of the mandible without the head changing position can be detected by the gyroscope. On the other hand, an IMM type movement will be detected by the accelerometer, in particular if the head moves on this occasion. An RMM type movement will be detected by the gyroscope, which is highly sensitive thereto.

Example 16

Figure 15:
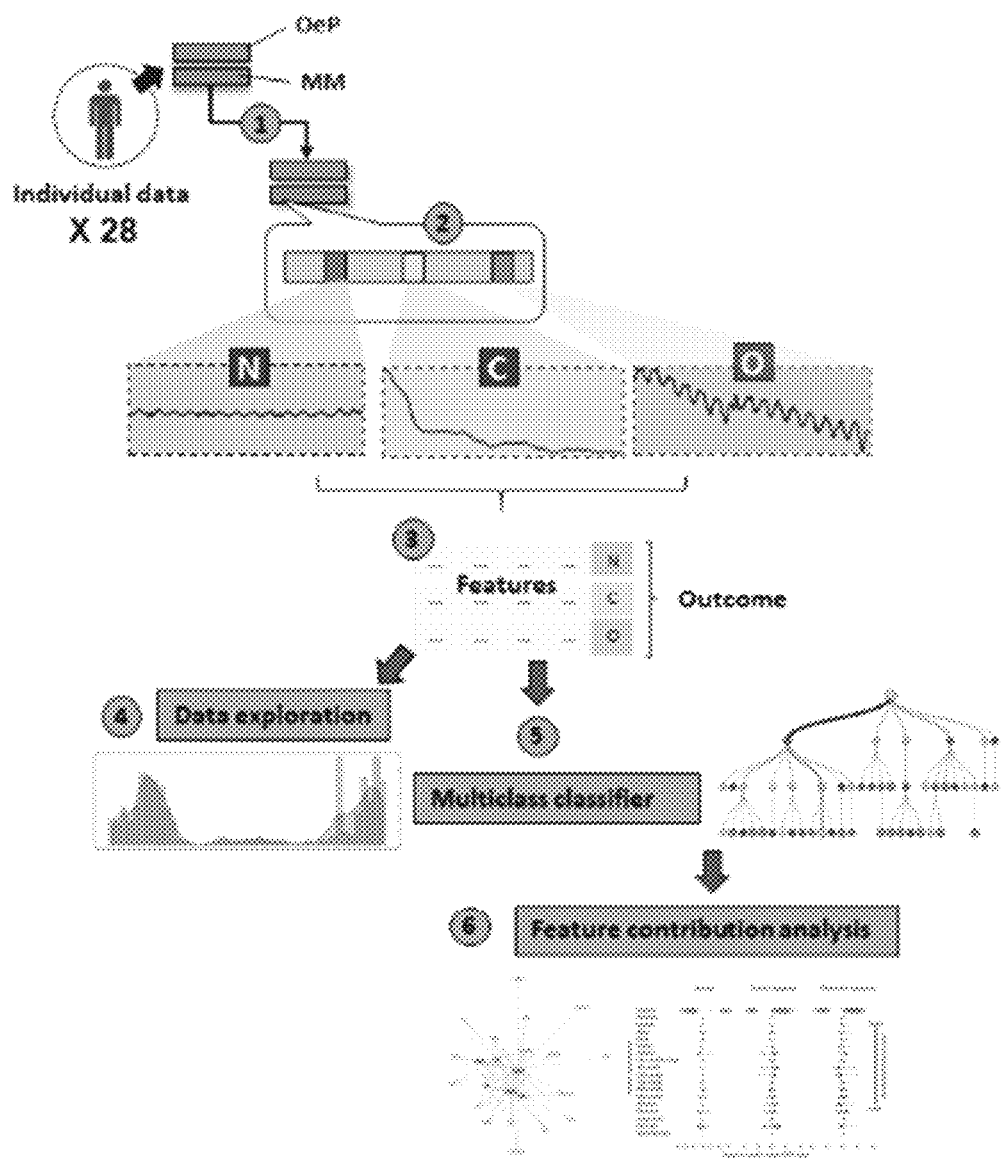
FIG. 15 shows an exemplary procedure for feature extraction, data processing, and data description.

In a further example, reference is made to an exemplary procedure for feature extraction, data processing, and data description that is of use in the methods and devices that are provided herein. Such a procedure is schematically shown in FIG. 15.

In particular, feature extraction, data processing and descriptive were done in R statistical programming language (8), while Machine learning experiments were conducted using sci-kit learn and SHAP packages in Python language.

23 different features were extracted from the mandibular movement raw signal of each event, or each 10 seconds of normal breathing. These features included: central tendency (mean, median and mode) of MM amplitudes; MM distribution (raw or enveloped signals): skewness, Kurtosis, IQR, 25$^{th}$, 75$^{th}$ and 90$^{th}$ centiles; extreme values: Min, Max, 5$^{th}$ and 95$^{th}$ centiles of MM amplitudes; tendency of variation: Linear trend and coefficients of Tensor product-based spline factors (S1, 2, 3, 4) from a generalized additive model to evaluate MM in function of Time; duration of each event.

The impact of the various features on the model's classification into central hypopneas, normal sleep, and obstructive hypopneas can be described by means of the SHAP score. The SHAP score measures the average marginal contribution across all possible coalitions with other features to classify 3 target labels. The higher the SHAP score, the more important contribution that feature may provide. The Lundberg's Shapley additive explanation (SHAP) method unified the Shapley's score in cooperative game theory (1953) (Lloyd S Shapley. "A value for n-person games". In: Contributions to the Theory of Games 2.28 (1953), 307-317.) and the local interpretation approach (Marco Tulio Ribeiro, Sameer Singh, Carlos Guestrin. "Why should i trust you? Explaining the predictions of any classifier". In: Proceedings of the 22nd ACM SIGKDD International Conference on Knowledge Discovery and Data Mining. ACM. 2016, 1135-1144.) to provide the best solution so far to explain any black-box model. The SHAP theory considers the input features as "players" in a cooperative game were the "payout" is making correct prediction of a target label (i.e. central or obstructive hypopnea). The SHAP algorithm lets each feature value to join with other features in random order to form a coalition, then assign a payout (SHAP score) for each feature values depending on their contribution to the total prediction. The SHAP score is the result from averaging the change in prediction that a coalition gains when a new feature participated. In essence, SHAP score of a feature value is the average marginal contribution of that feature value across all possible coalitions for a particular prediction.

In particular, the features are extracted as follows:
1. Loading a sequence of raw MM data at (e.g. sampling rate=10 or 25 Hz). This sequence has a significant duration, e.g. between 30 minutes and 8 hours;
2. Marking timestamps of obstructive and central hypopnea events;
3. For each time stamp ti, perform the following steps
   3.a. Check whether ti is the beginning of an Obstructive or Central hypopnea event.
   3.b. If ti is the beginning of an obstructive or central hypopnea event,
       assign ti to (t_begin), and subsequently search for the ending (t_end); and,
       extract the raw data sequence to a temporary holder named "Event E", by indexing t_begin and t_end;
4. For each event E, perform the following steps
   4.a. Calculate event duration dt=(t_end−t_begin)
   4.b. Determine the distribution of the measured parameters during the event;
       Min, Max, Mean, median, mode, $5^{th}$, $25^{th}$, $75^{th}$, $90^{th}$, $95^{th}$ centiles, Skewness, Kurtosis, IQR;
       Fit a GAM non-linear model to estimate MM amplitude and/or position by a spline function on time t, then extract the coefficient of spline function;
       Fit a simple linear model, extract the Intercept and linear slope;
       Concatenate all features+label by matching the measured data with a mandible movement class.

After feature extraction, the extracted features and corresponding target labels were integrated to a tabular dataset.

After that, exploratory data visualization, one-way ANOVA and pairwise student-t tests with Bonferroni correction are performed to classify the mandibular movement features in 3 groups: normal breathing, obstructive and central hypopneas. Significance level are set at highly stringent criteria (p=0.001) (10) for null-hypothesis testing.

For the purpose of model development, the data were randomly split into 2 subsets: a larger set (70%) for model development and a smaller set (30%) for model validation. Because the original training set was unbalanced between central (minority class) and obstructive hypopneas (majority class), a synthetic minority over-sampling technique (SMOTE, the Synthetic Minority Over-sampling Technique, which is well-known as such) on the training set before model development was applied.

A multiclass classification rule was built to classify the 3 groups using 23 input features. This consisted of a Random Forest algorithm that combined 500 distinct decision trees (each one was constructed on a random subset of 5 features).

The content of the Random Forest model was then analysed in order to evaluate the importance of each feature and the possible coalition that contributed to the classification (potential combinations among them to differentiate obstructive from central hypopnea). To evaluate the contribution of each features to the prediction, the Lundberg's Shapley additive explanation (SHAP) method is adopted which, as such, is well-known in the art.

These methods allow detecting of, inter alia, obstructive hypopneas and central hypopneas.

Example 17

Figure 16:
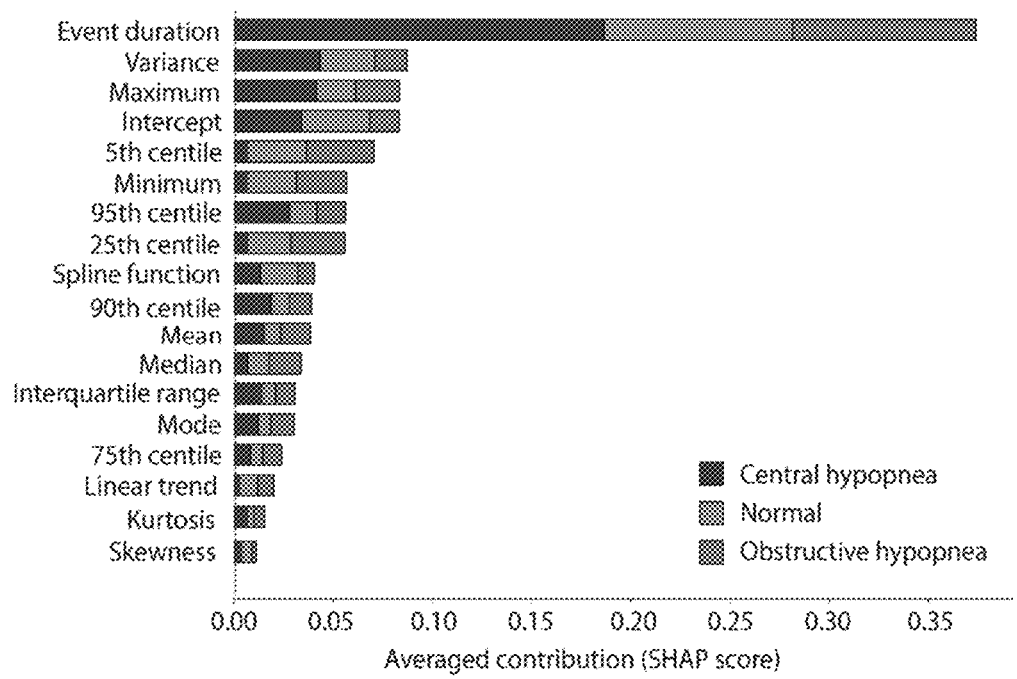
FIGS. 16 and 17 show an analysis of mandibular movement data captured by means of a magnetic sensor.
Figure 17:
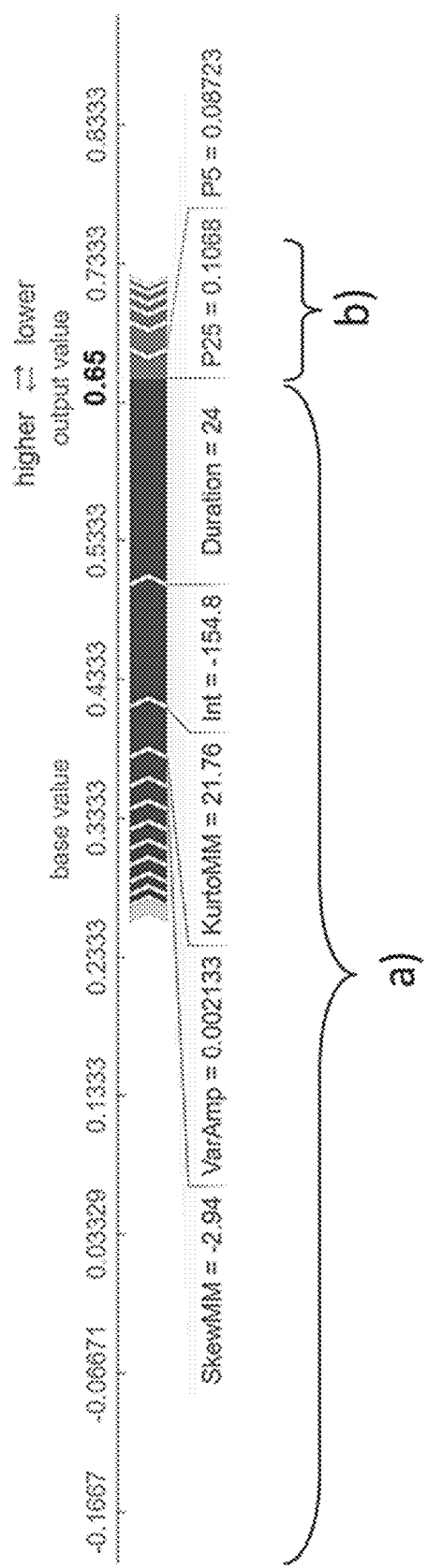

In a further example, reference is made to FIGS. 16 and 17. These figures show an analysis of mandibular movement data captured by means of a magnetic sensor. The data analysis as such is similar to data analysis of mandibular movement data captured by means of an accelerometer and/or a gyroscope in addition to a magnetic sensor.

FIG. 16 shows the 18 most important MM signal features derived from magnetometer measurements, ranked by their global impact on the model's prediction. The bars indicate the mean SHAP score for each feature, stratified by 3 target labels Central hypopneas (dark grey), Normal (light grey) and Obstructive hypopneas (grey). The SHAP score measures the average marginal contribution across all possible coalitions with other features to classify 3 target labels. The higher SHAP score, the more important the contribution that said feature may provide.

FIG. 17 shows the interpretation of an event based on extracted features and based on the SHAP score. In particular, FIG. 17 shows the SHAP score scale and the probability of a target label. FIG. 17 comprises two general regions: region a) and region b). Region a) comprises the extracted features that support the prediction of a target label, and region b) comprises the extracted features that point away from said target label.

Example 18

Figure 18:
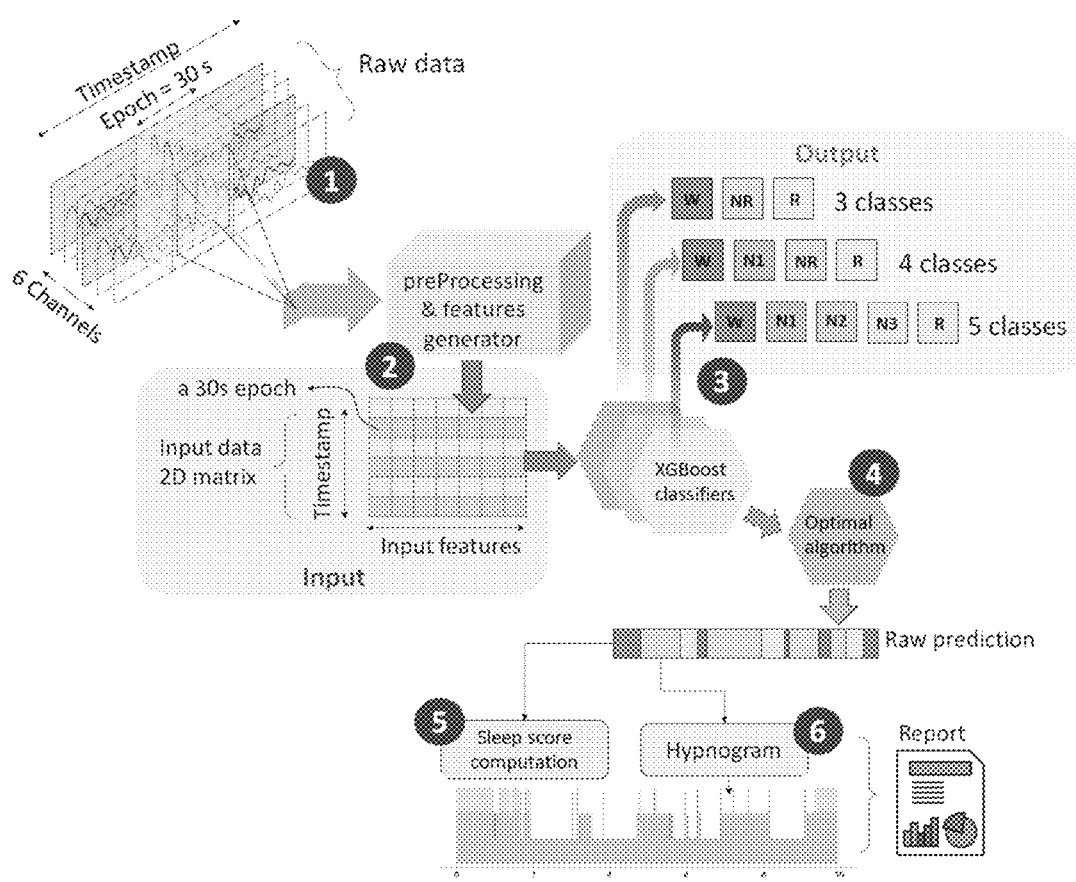
FIG. 18 shows an exemplary method for automated sleep stages detection from mandibular movement data captured by means of gyroscope and an accelerometer. The method is discussed further in Example 18.

In a further example, reference is made to FIG. 18, which illustrates an exemplary method for determining sleep stages from mandibular movement data captured by means of gyroscope and an accelerometer. The steps discussed below correspond to the reference numbers in FIG. 18.

In particular, the steps are as follows:
(1) Mandibular movements are recorded during subject sleep using a system of the present invention comprising a gyroscope and an accelerometer. The acquired data pack contains 6 channels of raw signals acquired by said tri-axial accelerometer and gyroscope sensors. The raw data may further include recordings from other devices suitable for determining the for sleep staging, such as EEG, EOG and EMG signals for sleep staging, 6 channels of MM signals acquired by tri-axial accelerometer and gyroscope sensors
(2) Raw data will pass through a pre-processing and feature generating module, after which it is consecutively segmented into 30 s length epochs. The pre-processing consists in producing time series sampled at 0.1 Hz and 0.034 Hz (sliding windows of 30 s) from the sleep scores sequences and the time series acquired with the sensor and the PSG. This pre-processing happens in two steps: the series or sequences are segmented, then feature extracting functions are applied to each window.

Hand-crafted feature extraction as the input data for machine learning experiment can be used. For example, a feature generating module extracted a set of 1728 features from the 6 channels of MM activity signal, using a sliding window centered on each 30 seconds epoch. The extracted features included: signal energy in the low frequency band (0-0.1 Hz), high frequency band (>0.3 Hz) or respiratory frequency band (0.2-0.3 Hz), exponential moving averages with several half-life periods, entropy of the energy in the several frequency bands, statistical features applied on the above features: tendency of centrality (mean, median), extreme values (min, max), quartiles, standard deviation, as well the normal standardized value of all above features.

(3) The extracted features set will be fed to a machine learning classifier, generating the soft-prediction scores (i.e., the probability) and binary output for each target label, according to a specific classification task. The automated sleep staging task was approached at three levels of complexity. The task targets are the basic 3 sleep stages: Wake, nonREM (including N1, N2, N3) and REM.

The feature selection and hyperparameter tuning were performed with cross-validation, in which the input data were randomly split into folds at the levels of participants. The final model was trained on the whole training set using only the most relevant features and optimized hyperparameter values. Due to the imbalanced proportion among the target labels, the training data was balanced by the Synthetic Minority Oversampling Technique (SMOTE) before each training session.

Machine learning algorithm: Extreme Gradient boosting (XGB) classifier is adopted as the core algorithm for all three classification tasks. The XGB classifier is optimized during training process by minimizing a regularized objective function that combines a convex loss function (based on the difference between the predicted and target outputs) and a penalty term for model complexity.

Model training: The learning objective is set a multiclass classification, which aims to classify 3 target labels, depending on the specific task. The training implied a Dropout-Multiple Additive Regression Trees (DART) booster and histogram optimized approximate greedy tree construction algorithm. Logarithmic loss was chosen as evaluation metric (thus optimizing the balanced accuracy among 3 target classes). To prevent overfitting, learning rate (eta, or step-size shrinkage) parameter is set at 0.01, this will shrink the feature weights to make the boosting process more conservative.

The model's output implied a soft-max function to generate the probability score for each target label, then the final decision (assigning only one label to each 30 s segment) is achieved by applying an argmax function on those 3 probability scores.

(4) Depending on the epoch-by-epoch agreement between model's prediction and the reference PSG scoring on the unseen validation dataset, the most satisfying solution are adopted for implementation. Further quantitative evaluations were carried out to verify whether the chosen algorithm could provide a reliable estimation of the sleep quality scores such as TST, sleep efficiency, REM ratios, and so on. The model selection was based on following criteria:

Class-wise agreement evaluation: The normalized confusion matrices allow evaluating the model's class-wise performance for a specific multi-class classification task. The rows are the truth derived from manual PSG scoring and the columns indicate the results of automated algorithmic scoring. The diagonal cells of the confusion matrix indicate class-wise true positive rate.

Precision (or positive predictive value) measures the mode's ability to correctly identify the positive cases, defined as True positive/(True positive+False positives); Recall (also known as sensitivity, hit rate or true positive rate) indicates the model's utility, defined as the fraction of correct classifications among all targeted instances: Recall=True positive predictions/All positive instances;

F1 score is a combined metric, defined as the harmonic mean of Recall and Precision per class:

2*(Precision*Recall)/(Precision+Recall)

F1 score has an intuitive meaning, it indicates how precise the model is (how many epochs it classifies correctly), as well as how robust the model is (low misclassification rate). Since the real-life data present the unbalanced proportions among sleep stages and all labels are equally important, the classifier that gets equally high F1 scores on all classes is adopted.

Global epoch-by-epoch agreement evaluation metrics: The balanced accuracy (BAC) measures the mean of true positive and true negative rates among the targeted class. The Cohen's Kappa coefficient measures the agreement strength between the model's classification and true observations (manual PSG scoring). It could be interpreted as 6 levels of agreement strength: lower than 0: Poor, 0-2: Slight, 0.2-0.4: Fair, 0.41-0.6: Moderate, 0.61-0.8: Substantial, 0.81-1: Almost perfect.

(5) Prediction data from the selected (3 class task) model will pass through the interpreting module. The first submodule (sleep score computation) will convert the sequence of predicted sleep stages into quantitative scores.

Definitions of these quantitative scores are presented in the table below:

|  | Definition | Unit |
| --- | --- | --- |
| Time based indices | | |
| Total sleep time (TST) | Total sleep time (TST) | Hour or minutes |
| Total nonREM sleep time | Sum of all epochs classified as nonREM sleeps (resolution: 30 s) | Hour or minutes |
| Total REM sleep time | Sum of all epochs classified as REM sleeps (resolution: 30 s) | Hour or minutes |
| Ratio based indices | | |
| NonREM ratio | 100 × Total nonREM sleep time/TST | Percent (%) |
| REM ratio | 100 × Total REM sleep time/TST | Percent (%) |
| Wake ratio | 100 × Total Wake time/TST | Percent (%) |
| Sleep efficiency ratio | 100 × total sleep time/total time in bed (recording) | Percent (%) |

-continued

| | Definition | Unit |
|---|---|---|
| | Latency indices | |
| Sleep onset latency | The elapsed time between the start of recording until the sleep onset | minutes |
| REM latency | Elapsed time from the sleep onset to the first REM epoch | minutes |
| | Occurrence rating | |
| Arousal index | Total number of all arousal events/TST in h | n/h |

(6) Hypnogram creation: A customized function converts the sequence of discrete encoded labels (for example: 2=Wake, 1=Rem sleep, 0=nonREM sleep) into a hypnogram. This graph presents the step-lines to represent the discrete sleep stages values as a function of time, which simulates a conventional hypnogram obtained from manual PSG scoring.

Example 19

Example 19 presents an experimental continuation of Example 18. In particular, the method presented in Example 18 was performed on a group of 96 participants, which were randomly assigned into a training subset (n=68, 70%) and a validation subset (n=28, 30%). Both subsets represent a population of healthy adults within an age range of 18 to 53 years.

Mandibular movements were recorded during subject sleep using a system of the present invention comprising a gyroscope and an accelerometer. The acquired data pack contains 6 channels of raw signals acquired by said tri-axial accelerometer and gyroscope sensors. The raw was used to develop the automated sleep staging model. Additionally, reference data was recorded using devices suitable for determining the sleep staging, such as EEG, EOG and EMG. The latter data was used to determine the accuracy of the applied models.

Instead of using deep learning models, a conventional framework was followed, which implies handcrafted features extraction and structured data driven algorithm. The handcrafted features extraction allows better control and understanding of input data compared to black-box models like convolutional neural network. XGBoost was adopted for the classification task. This algorithm offers several advantages over classical methods (LDA, SVM, RF), including high efficiency in computation and resource, allowing very fast training and execution speed.

Subject subsets: Polysomnography (PSG) profiles from the group of 96 participants indicated a normal sleep activity in both subset groups, with median sleep efficiency of 89.4% and 87.3%. Within each set, the data structure also presents an imbalance in proportion among 3 sleep stages: except for Wake labels which are regular in most of cases, the nonREM sleeps were predominant over the REM sleeps in both groups (92.3 vs 7.7 for trainset and 79.9 vs 20.1 for validation set), suggesting that a data balancing technique is required during model development, and the performance metrics should be carefully interpreted during model validation.

3 Class scoring: The present model aims to classify Wake (no sleep), nonREM and REM sleeps. The model results in a well-balanced accuracy among 3 classes (82.9%, 74.9% and 82.5% for wake, nonREM and REM sleeps, respectively). The model also has a substantial agreement strength (Kappa=0.71). It performs best for detecting wake epochs, with F1 score of 0.86. Guided by the distribution of Wake, nonREM and REM instances in the models, identifying the Wake was found to be easier than distinguishing between nonREM and REM, since the Wake instances were well clustered and clearly separated from the other instances, while most of REM labels were more dispersed and blended into other nonREM or Wake points. This pattern suggests that a nonlinear algorithm, such as Random Forest, XGboost or Deep neural network may be considered for successfully separating 3 classes.

Agreement analysis for the sleep quality indices: The 3 class task sleep staging algorithm can automatically classify each 30 seconds epoch as wake, nonREM or REM. The outputs were then transformed by a second algorithm to provide an estimation of sleep quality indices. Those indices could be classified in 3 main categories: a) Time based indices, which measure the cumulated time (in minutes) in sleep (TST) or during a specific sleep stage, such as Wakefulness, REM or nonREM; b) Ratio based indices, which are estimated as the percentage of a specific sleep stage (REM, nonREM) over all in-sleep epochs; c) Latency based indices, which measures the elapsed time between the beginning of recording and sleep onset (sleep latency), or between the sleep onset and the first REM epoch (REM latency).

Quantitative scores for the automated sleep staging algorithm were determined according to the Table presented in Example 18. Differences between the standard scoring of the PSG profiles and the quantitative scoring of the automated sleep staging algorithm are presented in the Table below:

| Parameter | Median | 95% CI | 97.5% CI | 99% CI |
|---|---|---|---|---|
| TST (min) | −7.148 | −18.190 to +2.349 | −20.336 to +4.383 | −22.758 to +7.430 |
| Total NonREM sleep time (min) | −26.633 | −42.686 to −10.616 | −45.691 to −6.839 | −50.243 to −2.882 |
| Total REM sleep time (min) | +22.560 | −3.781 to +51.384 | −9.645 to +58.426 | −17.495 to +65.436 |
| Total Wake time (min) | +11.734 | +3.281 to +18.954 | +1.517 to +20.423 | −0.228 to +22.449 |
| Wake index (n/h) | +1.478 | +1.075 to +1.892 | +1.003 to +1.989 | +0.916 to +2.093 |
| Wake ratio (%) | +3.908 | +1.346 to +6.100 | +0.770 to +6.526 | +0.078 to +7.039 |

| Parameter | Median | 95% CI | 97.5% CI | 99% CI |
|---|---|---|---|---|
| NonREM ratio (%) | −6.423 | −10.259 to −2.394 | −11.006 to −1.595 | −12.300 to −0.533 |
| REM ratio (%) | +6.469 | +0.060 to +13.123 | −1.407 to +14.587 | −2.824 to +16.334 |
| Sleep efficiency (%) | −1.289 | −2.705 to −0.199 | −3.032 to +0.010 | −3.402 to +0.232 |
| Sleep latency (min) | +1.424 | −0.906 to +3.720 | −1.569 to +4.166 | −2.200 to +4.806 |
| REM latency (min) | −17.112 | −48.849 to −2.353 | −53.831 to +2.375 | −60.802 to +7.229 |

The data indicate that the 3 class based scoring algorithm allows measuring the total sleep time at an acceptable accuracy (median difference of only −7.15 minutes, 97.5% CI: −20.34 to +4.38) in comparison to the reference method (manual PSG scoring). The agreement was also good for determining sleep efficiency (median difference: −1.29%; −3.03 to +0.01).

Conclusions: The feasibility of using mandibular movements recorded during subject sleep using a system of the present invention comprising a gyroscope and an accelerometer was explored. The results demonstrate that automated sleep staging detection based on data measured by a gyroscope configured for measuring rotational movement offers a better performance at all three resolution levels (for 3 class scoring) in comparison to systems of the art comprising an accelerometer only.

Figure 19:
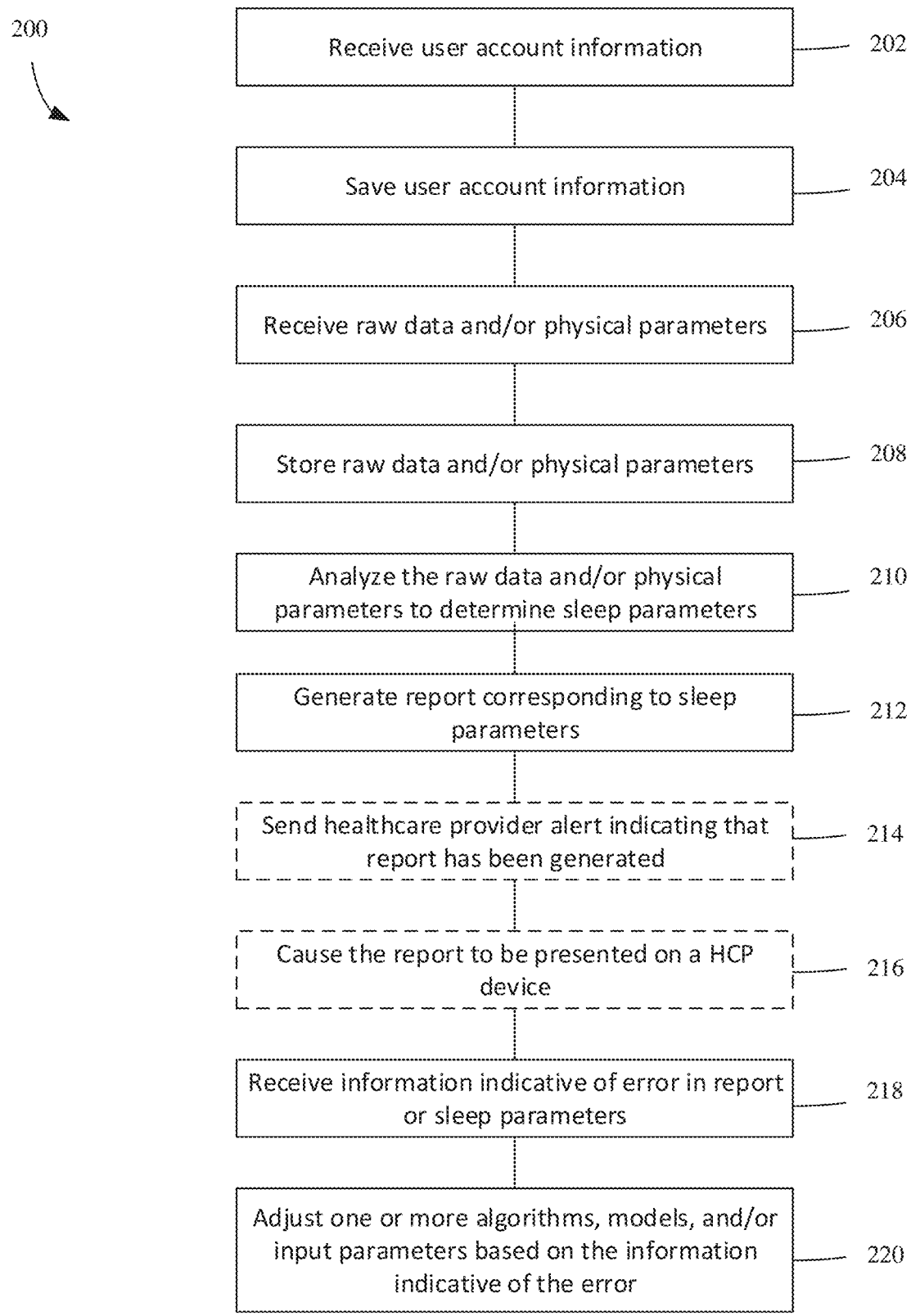
FIG. 19 shows an exemplary process flow for generating a report based on data generated by a sensing unit.

Referring now to FIG. 19, an exemplary process flow generating a report based on data generated by a sensing unit is illustrated. Some or all of the blocks of the process flow in this disclosure may be performed in a distributed manner across any number of devices (e.g., a server such as server 108 of FIG. 1A and/or analysis device 110 of FIG. 1A). Some or all of the operations of the process flow may be optional and may be performed in a different order.

At block 202, computer-executable instructions stored on a memory of a device, such as a server, may be executed to receive user account information (e.g., from a mobile device such as mobile device 106 of FIG. 1A) during a set up process. The user may provide information on their sleep quality such as by recording responses to questions about their sleep quality entered into the mobile application. At block 204, computer-executable instructions stored on a memory of a device, such as a server, may be executed to save user account information (e.g., to a server such as server 108 of FIG. 1A), including information from the user on their sleep quality.

At block 206, computer-executable instructions stored on a memory of a device, such as a server, may be executed to receive raw data and/or physical parameters. For example, a sensing unit (e.g., sensing unit 102 of FIG. 1A) may generate sensor data such as gyroscope data and/or accelerometer data and/or physical parameter data and may send this information to a mobile device and the mobile device may send the information to the server. At block 208, computer-executable instructions stored on a memory of a device, such as a server, may be executed to store the data and physical parameters.

At block 210, computer-executable instructions stored on a memory of a device, such as a server, may be executed to analyze the raw data and/or physical parameters to determine sleep parameters. For example, sleep parameters may be sleep quality parameters and may be determined using any approach described herein. In one example, sleep parameters may include total sleep time (TST), sleep onset latency (SOL), wake after sleep onset (WASO), awakening index, sleep efficiency (SE), ratios of REM, nonREM sleep, REM sleep latency, and other sleep quality metrics. At block 212, computer-executable instructions stored on a memory of a device, such as a server, may be executed to generate a report corresponding to the sleep parameters. For example, the server may generate the report which may be available for viewing on the analysis device and/or mobile device. In one example, the report may further include a presence or a likelihood of a presence of one or more sleep related conditions and/or disorders. At optional block 214, computer-executable instructions stored on a memory of a device, such as a server, may be executed to send a healthcare provider an alert indicating that a report has been generated. For example, the server may send the analysis device a message that a report is available for viewing. At optional block 216, computer-executable instructions stored on a memory of a device, such as a server, may be executed to cause the report to be presented on the healthcare provider device (e.g., the analysis device). The healthcare provider can then interpret the report to diagnose a sleep event(s).

At block 218, computer-executable instructions stored on a memory of a device, such as a server, may be executed to receive information that is indicative of an error in the report and/or sleep parameters. For example, the healthcare provided may analyze the report and determine that certain parameters are inaccurate and/or that a presence or absence of a sleep disorder or condition in a report is inaccurate. This information may be provided to the server from the analysis device. At block 220, computer-executable instructions stored on a memory of a device, such as a server, may be executed to adjust one or more algorithms, models, and/or parameters of the analysis software used to process the data at block 210 based on the information received at block 218.

Figure 20:
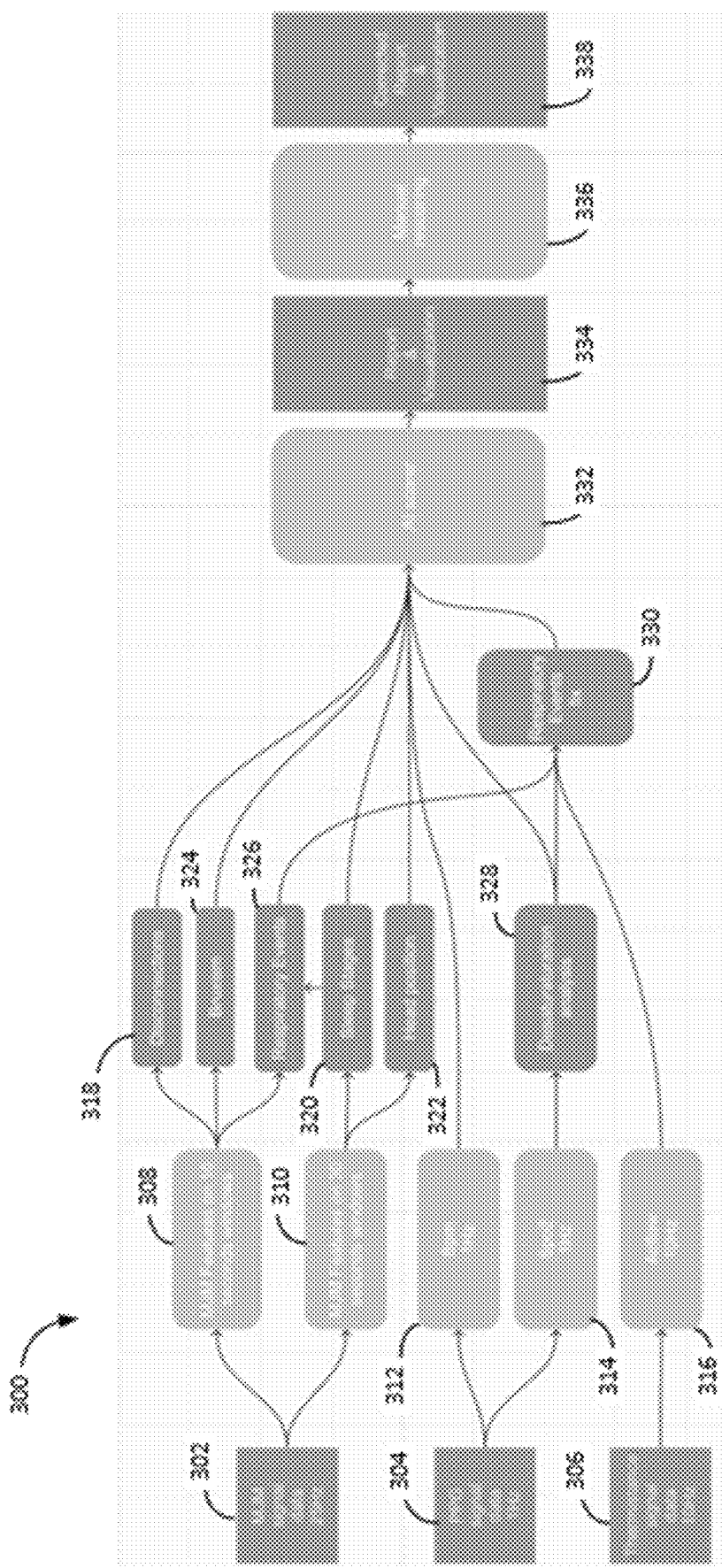
FIG. 20 shows an exemplary data flow for processing data generated by the sensing unit to determine, detect, assess, and/or diagnose various sleep related disorders and/or conditions.

Referring now to FIG. 20, an exemplary data flow for processing data generated by the sensing unit to determine, detect, asses, and/or diagnose various sleep related disorders and/or conditions is illustrated. As shown in FIG. 20, Mandibular Jaw Movement (MJM) signal data 302 may be received from a sensing unit. MJM signal data 302 may include gyroscope data and/or accelerometer data sampled at a certain frequency (e.g., 25 Hz). MJM signal data 302 may be used to determine movements of the user's head that indirectly or directly cause movement of the mandible and movements of the user's mandible that are independent of movements of the user's head. For example, data from the accelerometer is well-suited for detecting movements of the user's head and may be used to detect position changes of the head (e.g., from supine to lateral) and detecting tracheal tug. Position changes may be detected based on distribution of gravity on three axes of the accelerometer. Tracheal tug may be detected based on signal data that indicates movements that are more linear than rotational. Detection of position changes of the head and/or tracheal tug may be indicative of movements of the head that cause movement of the mandible. Additionally, the gyroscope is well-suited for detecting movement of the mandible. Movements of the mandible that are not caused by movements of the head are understood to be linked to brain control. For example, brain control may be detected by measuring the angular speed of the mandible movements which are typically rotational movements.

As movement of the mandible may be indicative of sleep stages, sleep state, sleep disorders, respiratory effort, motor events, endotyping, and/or sleep diagnostic parameters, it is desirable to discern between movement of the mandible caused, either directly or indirectly, by the head, and movement of the mandible independent of head movement. Accordingly, if signal data from the accelerometer in the MJM signal data is a significant value (e.g., above a certain threshold value) indicative of a presence of head movement (e.g., a change in head position), then data from the gyroscope during this time is not relevant or useful as movement of the mandible may be the result of the head movement. In one example, the threshold for a significant value may be 0.9 and the value of the signal data may be between 0.0 and 1.0. Conversely, if the MJM signal data from the accelerometer is insignificant (e.g., below a certain threshold value) representing an absence of acceleration of the head, then the MJM signal data from the gyroscope is indicative of brain control and thus the likelihood of a respiratory event may be high and/or such gyroscope data may be indicative of one or more of sleep stages, sleep state, sleep disorders, respiratory effort, motor events, endotyping, sleep diagnostic parameters, and the like. In one example, the threshold for an insignificant value may be 0.1 and the value of the signal data may be between 0.0 and 1.0. Such MJM signal data may be useful for determining the likelihood of a of sleep stages, sleep state, sleep disorders, degree of respiratory effort, motor events, endotyping, sleep diagnostic parameters, and the like. In another example, if the signal data from the accelerometer is significant and thus indicates the presence of movement (e.g., the signal data from the accelerometer is above a certain threshold) but the signal data from the gyroscope is insignificant (e.g., below a certain threshold), the subject is likely experiencing a tracheal tug and thus a probability of a respiratory event is low. In one example, the threshold for a significant value may be 0.9, the threshold for an insignificant value may be 0.1 and the value of the signal data may be between 0.0 and 1.0. Accordingly, based on the accelerometer signal data and the gyroscope signal data in the MJM signal data, diagnostic information may be determined and/or generated which may indicate the presence or likelihood of a presence of a sleep disorder, a degree or amount of respiratory effort, endotyping, motor events, respiratory events, sleep states, sleep stages and/or any other sleep diagnostic parameters.

Photoplethysmography (PPG) signal data 304 may also be received from a sensing unit. PPG signal data 304 may include data from the PPG sensor of the sensing unit (e.g., oximeter). In one example, PPG signal data 304 may be sampled at 1 Hz. PPG signal data 304 may be useful for determining a heart rate of the user (e.g., beats per minute) and/or oxygen saturation levels. Data indicative of a user's heart rate and oxygen saturation levels may be processed by the data analysis unit to inform or otherwise contribute to a determination of a presence or likelihood of a presence of a sleep disorder, a degree or amount of respiratory effort, endotyping, motor events, respiratory events, sleep states, sleep stages and/or any other sleep diagnostic parameters. For example, a low oxygen saturation level may be indicative of an obstruction. In another example, a high heart rate may be indicative of arousals or awakenings.

Thermistor signal data 306 may optionally be received from the sensing unit. Thermistor signal data 306 may be generated by thermistor sensors and may include temperature information. In one example, the thermistor signal data 306 may be sampled at 10 Hz. Thermistor signal data 306 may be indicative of a temperature value which may be compared to temperature thresholds or ranges to determine if a user is inhaling or exhaling. In one example, inhaling may correspond to a lower temperature than exhaling as air leaving the body is often a higher temperature than the ambient environment. If the temperature value is above a certain threshold then the thermistor signal data 306 may be determined to indicate exhaling and if the temperature value is below a certain threshold value then thermistor signal data 306 may be determined to indicate exhaling. Such airflow information may be used by a data analysis unit to determine a presence or likelihood of a presence of a sleep disorder, a degree or amount of respiratory effort, endotyping, motor events, respiratory events, sleep states, sleep stages and/or any other sleep diagnostic.

A data analysis unit may process MJM signal data 302 to determine MJM features 308 for a first predetermined time window (e.g., 10 second windows) and MJM features 310 for a second predetermined time window (e.g., 30 second windows) using advanced signal processing features (e.g., resampling, filtering, Fourier transforms, entropy analysis, etc.). For example, a data analysis unit may perform feature extraction based on the approach described with respect to FIG. 15 and/or any other approach described herein. Additionally, a data analysis unit may determine beats per min data 312 and oxygen saturation data 314 from PPG signal data 304. For example, a pulse rate may be determined from PPG signal data 304 to determine beats per min data 312 and/or PPG signal data 304 may be analyzed to determine blood oxygen saturation. Also, a data analysis unit may also analyze thermistor signal data 306 (e.g., using signal processing filters) to determine airflow data 316 which may be indicative of whether or not the user is breathing (e.g., inhaling or exhaling) at a given time.

Based on MJM features 308, a data analysis unit may determine disconnections data 318, bruxism data 324 and respiratory events data 326. For example, the data analysis unit may process MJM features 308 using one or more algorithms to detect disconnections between the sensing unit and the user in MJM signal data 308. If it is determined that certain portions of MJM signal data 308 were generated during a disconnection, the data analysis unit may disregard the MJM signal data. Additionally, a bruxism detection machine learning model may be applied to MJM signal data 308 to determine whether there is bruxism in each window (e.g., 10 second windows). MJM signal data 308 may further be analyzed to determine a presence or absence of respiratory events. Optionally MJM signal data 310 may be additionally processed to make this determination. In one example, a presence or absence of respiratory event may be determined using a machine learning model that inputs each 10 second MJM features windows and outputs a multiple class (normal/obstructive/central/arousal), a machine learning model that inputs each 10 second MJM features windows and outputs a binary class "end of event" for obstructive/central events, an attention layer to improve the model, a model to classify obstructive events as 3% hypopneas or 4% hypopneas, and/or a last attention model to improve the model. Prior to processing the 10 second MJM features windows by the machine learning model, the data analysis unit may analyze the MJM signal data from the accelerometer to determine that data from the accelerometer is insignificant (e.g., below a certain threshold value) and that MJM signal data from the gyroscope is significant (e.g., above a certain threshold), and thus there is a high likelihood of a respiratory event.

The data analysis unit may process MJM signal data 310 to determine sleep stages data 320 and head position data 322. For example, a 2-step algorithm to detect sleep stages based on MJM signal data 310 may be used. In the first stage a machine learning model may process MJM signal data 310 and output class probabilities for awake/light sleep/deep sleep/REM sleep. At the second stage, the outputs of the class probabilities for awake/light sleep/deep sleep/REM sleep are applied to an attention layer that improves the classification of sleep class. For example, at the second stage, the values of windows of MJM signal data occurring a predetermined amount of time before and after (e.g., 12.5 min before/after) certain MJM signal data in question are considered, and/or probability averages for time periods before and after each predetermined time (e.g., 30 seconds) window are determined and these outputs are fed into logistic regressions. Head position data 322 may be determined by applying MJM signal data to head position detection algorithm to output a classification such as lying, side, back, or other. Desaturation analysis data 328 may be determined by the data analysis unit based on oxygenation saturation data 314 and may be indicative of oxygen desaturation in the user's blood stream.

Data from desaturation analysis data 328, airflow 316, and respiratory events 326 may be used to determine respiratory events fix 330. For example, the data analysis unit may remove an obstructive event if it meets all the following conditions: (1) there is a valid Spo2 signal during the event and one minute after its ending, (2) there is no Spo2 desaturation on the period (higher than or equal to 4%) overlapping the event, and (3) the event is not an apnea (an apnea being identified by having more than 10 s of the event airflow less than or equal to 10% of the airflow baseline).

The data analysis unit may then process airflow data 316, desaturation analysis data 328, beats per minute data 312, head position data 322, sleep stages data 320, respiratory events data 326, bruxism data 324, and disconnections data 318 using AI scorer 332 to determine a list of medical scores indicative of a likelihood of a presence or absence of one or more sleep related conditions or disorders, a degree or amount of respiratory effort, endotyping, motor events, respiratory events, sleep states, sleep stages and/or any other sleep diagnostic parameters. For example, airflow data 316 may be indicative of inhale and/or exhale amplitudes and may be informative with respect to the presence of a respiratory event, respiratory effort, a sleep stage, and/or sleep disorder; desaturation analysis data 328 may be generated by or derived by data generated by a pulse oximeter and may be informative oxygen levels in the user's blood stream and may be informative with respect mean, minimum, and maximum oxygen saturation levels as well as the presence of a respiratory event, respiratory effort, a sleep stage, and/or sleep disorder; head position data may be informative with respect to a respiratory event and/or sleep stage or stage; sleep stages may be informative with respect to durations of time in certain sleep states or stages as well as start and end times of certain sleep stages or events; and respiratory events may be informative with respect to respiratory effort, respiratory event scoring, durations of time for certain respiratory events, as well as start and end times of certain respiratory events. For example, data generated by a pulse oximeter and/or thermistor may be used for diagnosing a sleep event and/or may be used to determine an absence of a sleep event.

At report and visualization 334, the scores and any inferences and/or determinations regarding sleep related conditions or disorders may then be uploaded to a portal and made available (e.g., in report form) for review by healthcare provider and/or user. Manual rescoring data 336 may be generated by a healthcare provider and provided to the data analysis unit to make adjustments to the scores. The adjusted scores, inferences, and/or determinations may then be made available in a corrected report at corrected report and visualization 338.

Figure 21:
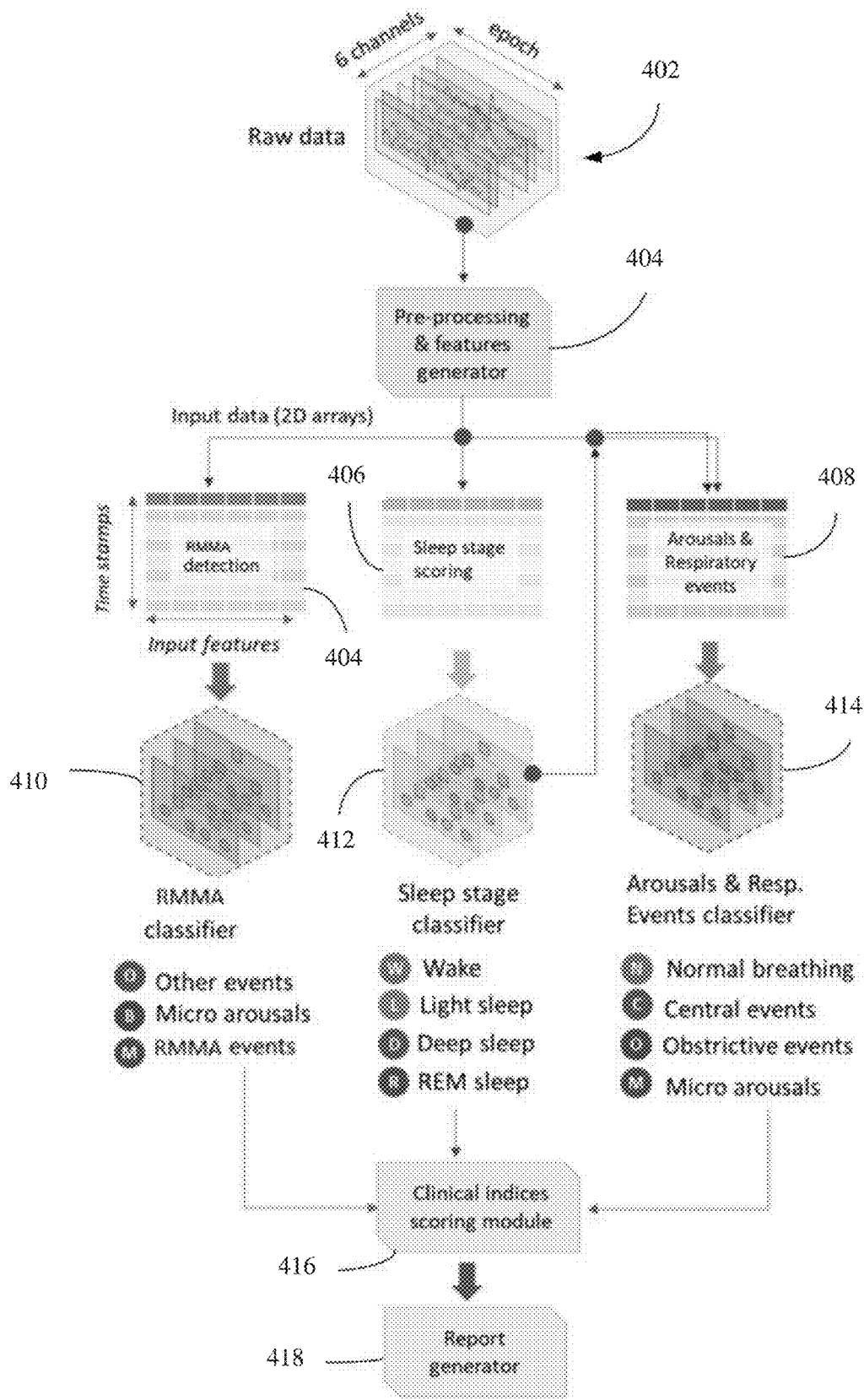
FIG. 21 shows an exemplary data flow for classifying sleep and generating a report.

Referring now to FIG. 21, an exemplary data flow for classifying sleep and generating a report is depicted. As shown in FIG. 21, data 402, which may be data from various sensors of a sensing unit (e.g., gyroscope, accelerometer, PGG, thermistor, etc.) is provided to pre-processing and features generator module 404. For example, the acquired raw data may be pre-processed then consecutively segmented into epochs of the predetermined time periods (e.g., 10 and/or 30 seconds). Relevant features may then be estimated for each epoch then stacked (e.g., into 2D arrays). For example, the output of pre-processing and features generator 404 may be Rhythmic Masticatory Muscle Activity (RMMA) detection array 404, sleep stage scoring array 406, and arousals and respiratory events array 408.

As shown in FIG. 21, classification may include RMMA classifier 410, sleep stage classifier 412, arousals and respiratory events classifier 414. For example, RMMA classifier 410 may process RM MA detection array 404, sleep stage classifier 412 may classify sleep stage scoring array 406, and arousals and respiratory events classifier 414 may classify arousals and respiratory events array 408. RM MA classifier 410 may classify micro arousals, RMMA events, and/or other sleep related events, for example. Sleep stage classifier 412 may classify awake, light sleep, deep sleep, and/or REM sleep, for example. Arousals and respiratory events classifier 414 may classify normal breathing, central events, obstructive events, and/or micro arousals, for example.

Outputs from each of RMMA classifier 410, sleep stage classifier 412, arousals and respiratory events classifier 414 may then then pass through clinical indices scoring module 416, which may handle computation of clinical indices for use by healthcare providers to assess the quality of sleep and occurring rate of sleep respiratory disturbances of the patient. Report generator 416 may generate a report including clinical indices, inferences and/or determinations relating to sleep conditions and/or disorders, and/or any other relevant information.

In one example, indices may include, total sleep time (TST), which may be the sum of the time periods that are not classified as awake, sleep onset latency (SOL), which may be the duration between the start of the recording and the start of the first classified continuous sleep period, wake time after sleep onset (WASO), which may be the sum of the time periods that are classified as awake appearing after the start of the first classified continuous sleep period, sleep efficiency (SE), which may be the total sleep time divided by the recording duration, awakening index, which may be the number of awakenings per hour, arousal index (ArI), which may be number of arousals per hour, proportions of light sleep, deep sleep and REM sleep, and/or REM sleep latency, which may be time lapse between SOL and first REM period. Other indices are also provided in the table below.

| Parameter | Full name (unit) | Definition |
| --- | --- | --- |
| AHI | Apnea hypopnea index (events/hour) | (# of apneas + # of hypopneas) × 60/total sleep time |

-continued

| Parameter | Full name (unit) | Definition |
|---|---|---|
| ORDI | Obstructive respiratory disturbance index (events/hour) | (# of obstructive apneas + # of mixed apneas + # of obstructive hypopneas + # of RERAs) × 60/total sleep time |
| RDI | Respiratory disturbance index (events/hour) | (# of apneas + # of hypopneas + # of RERAS) × 60 / total sleep time |
| OAHI | Obstructive apnea hypopnea index (events/hour) | (# of obstructive apneas + # of mixed apneas + # of obstructive hypopneas) × 60/total sleep time |
| CAHI | Central apnea hypopnea index (events/hour) | (# of central apneas + # of central hypopneas) × 60/total sleep time |
| AHI (4%) | Apnea hypopnea index with AASM's '1B Rule' for the scoring of hypopnea) (events/hour) | (# of apneas + # of hypopneas) × 60/total sleep time (with AASM's '1B Rule' for the scoring of hypopnea) |
| RERA index | Respiratory effort related arousals index (events/hour) | # of RERAs × 60/total sleep time |
| RE | Cumulative duration of increased respiratory effort (%) | (Cumulative duration of obstructive apneas, mixed apneas, obstructive hypopneas and RERAs)/total sleep time × 100 |

Figure 22C:
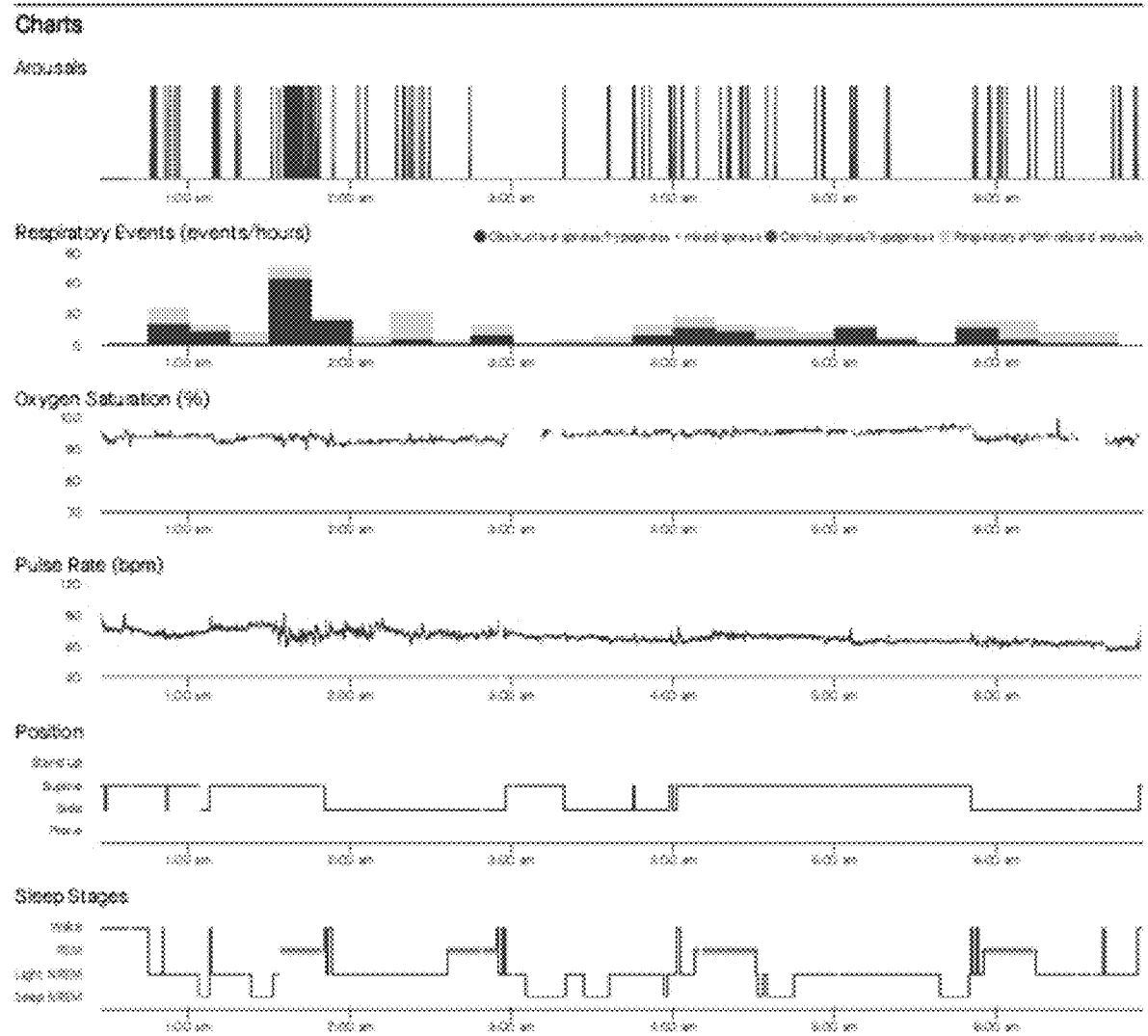

Referring now to FIGS. 22A-22C, an exemplary report is depicted including sleep/wake states, sleep stages, respiratory events, awakenings and arousals events, oxygen saturation information, pulse rate information, position information and interpretation. For example, the report included in FIG. 22A may be a cover page and may include patient information such as patient identifier, name, date of birth, age, sex, contact information, weight and/or height, medical and/or behavioral information (e.g., smoking, high blood pressure, complaints, etc.), physician information and the like. Additional patient comments about alcohol use, stimulant use, medical treatment and other information may be included. Recording information may also be included and may include the study date, time, duration and the like. The cover page may also summarize sleep/wake states (e.g., TST, sleep start/end, wake percentage, etc.) and sleep stages (e.g., REM percentage, light non-REM, and deep non-REM). A summary spectrum for apnea hypopnea index (AHI) may also be included which may indicate with the patient is non-obstructive sleep apnea, mild, moderate, and/or severe.

Referring now to FIG. 22B, information such as respiratory events, awakenings and arousals events, oxygen saturation, and pulse rate (bpm) may be included in the report. The respiratory events may include indices such as AHI, RDI, OAHI, CAHI, ORDI, RERA index, and/or respiratory effort, for example. Awakenings and arousals events may include an awakening index. Oxygen saturation information may include mean, max, min, and/or other relevant information. Pulse rate information may include mean, min and/or max. Position may include a position changes index, a percentage of time in supine and a percentage of time in non-supine. As shown in FIG. 22B, the report may further include an interpretation section which may provide a diagnosis (e.g., moderate OSA) as well as recommendations. Recommendations may include recommendations for treatment devices (e.g., Continuous Positive Airway Pressure, Mandibular Advancement Device, etc.) testing, therapy, and other suggestions (e.g., patient should avoid alcohol).

Referring now to FIG. 22C, the report may include several charts, graphics, plots, or other data or representations. For example, an arousals plot showing arousals over time, a respiratory events plots showing a number of events over time, an oxygen saturation plot showing oxygen saturation over time, a pulse rate plot showing pulse rate (e.g., beats per minute) over time, a position plot showing position over time, and/or a sleep stages plot showing various sleep stages over time may be included in the report. It is understood that any other data, plots, inferences, determinations, or information may be included in the report.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

It should be understood that any of the computer operations described herein above may be implemented at least in part as computer-readable instructions stored on a computer-readable memory. It will of course be understood that the embodiments described herein are illustrative, and components may be arranged, substituted, combined, and designed in a wide variety of different configurations, all of which are contemplated and fall within the scope of this disclosure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

TABLE 1 waking or sleeping (N1, N2, N3, or REM) state, positions/movements of the mandible and positions/movements of the head in a state that is assumed to be normal.

| State (asleep or awake) | Movements of the mandible | Position of the mandible | Typical head movements | Position of the head during sleep | Analysts window | Example of preprocessing of raw signals in the frequency domain | Example of preprocessing of raw signals | Example of features to extract and compare |
|---|---|---|---|---|---|---|---|---|
| Awake | Unpredictable, duration of more than 15 seconds | Instable | Presence of head movements | Lying or standing | 30 seconds | Band-pass filter | Exponential moving average | Normalized average (bigger for waking than sleeping state) |
| Asleep | Varies with the respiratory frequency | Stable | No head movements | Lying | | | | |
| N1 sleep | Varies with the respiratory frequency with variable peak-to-peak amplitude, limited duration of several minutes | Stable | No head movements | Lying | 30 seconds | N/A | Entropy of the frequency of the signal | Normalized average (bigger for N1 and REM than for N2 and N3) Amplitude variance |
| REM sleep | Varies with the respiratory frequency, with a net variability of the peak-to-peak amplitude, non-periodic | Stable with a tendency to lowering | No head movements | Lying | | | | (bigger for N1 and REM than for N2 and N3) Frequency variance (bigger for N1 and REM than for N2 and N3) |
| N2 sleep | Varies with the respiratory frequency with a minor variation of the peak-to-peak amplitude | Stable | No head movements | Lying | 30 seconds | Band-pass filter Low-pass filter | Exponential moving average | Normalized median (lower for N2 and N3) Normalized mean (lower for N2 and N3) |
| N3 sleep | Varies with the respiratory frequency with minor long-term (more than 10 minutes) variation of the peak-to-peak amplitude | Very Stable | No head movements | Lying | | | | |

TABLE 2 cerebral activations - cortical and sub-cortical activations

| Cerebral activations | Typical mandible movements | Typical mandible position | Typical head movements | Typical head position during sleep | Exemplary analysis | Example of preprocessing of raw signals in the frequency domain | Example of preprocessing of raw signals | Example of features to extract |
|---|---|---|---|---|---|---|---|---|
| Cortical | Abrupt and high-amplitude closing or opening duration between 3 and 15 seconds | Unstable between two extremes | With or without position changes of the head | Lying, typically with position changes of the head | 10 seconds | Low-pass filter | N/A | Amplitude and duration |
| Sub-cortical | Break in the oscillation/respiratory frequency Mandible movement of small amplitude or of moderate amplitude Short duration | Stable | With or without position changes of the head | Lying | 10 seconds | Band-pass filter | Exponential moving average | Amplitude and duration |

TABLE 3 typical behavior of cerebral contral far the detection of respiratory and non-respiratory motor events

| Events | Centrality of the signal that provides information on the state of the cerebral control | Amplitude of the signal that provides information on the state of the cerebral control | Variance of the signal that provides information on the state of the cerebral control | Frequency of the signal that provides information on the state of the cerebral control | Examples of relevant analysis windows | Example of preprosessing of raw signals in the frequency domain | Example of preprocessing of raw signals | Example of features to extract |
|---|---|---|---|---|---|---|---|---|
| Obstructive apnea-hypopnea | On the decline (other behaviours may be observed as well) | Significant, may strongly increase | Non-cyclical during the event but the event may be periodical | Respiratory | 10 seconds | Band pass filter | Exponential moving average | Centrality (e.g. average, mean, modes) Extremities (e.g. maximum, centiles) Distribution (e,g, shape) Duration Variance |
| Respiratory Effort Related Arousal (RERA) | Unchanged or slightly down | Significant, may slightly increase | None (stable), or week, or increasing | Respiratory | | | | |
| Central apnea-hypopnea | On the decline (other behaviors may be observed as well) | Very weak or zero | None (stable), or weak, sometimes periodical (increase-decrease or not) | Respiratory | | | | Trend |
| Bruxism | Stable | Very significant | Non-cyclical | Non-respiratory (typically1 Hz) | 30 seconds | Band pass filter | Entropy of the frequency of the signal | Centrality (e.g. average, mean, modes) Extremities (e.g. maximum, centiles) |
| No event | Stable | Very weak or zero | None (stable) | Respiratory | 30 seconds | N/A | N/A | N/A |

What is claimed is:

1. A method for diagnosing a sleep event of a subject, the method comprising:
    receiving mandibular rotational data generated by a gyroscope mounted on an exterior of a mandible of the subject, the mandibular rotational data corresponding to a time period during sleep and indicative of rotational movement of the mandible of the subject;
    receiving mandibular acceleration data generated by an accelerometer mounted on the exterior of the mandible of the subject, the mandibular acceleration data corresponding to the time period during the sleep and indicative of acceleration of the mandible of the subject, wherein the gyroscope and the accelerometer are disposed within a housing adhered to the exterior of the mandible of the subject;
    determining the mandibular rotational data is above a first threshold value;
    determining the mandibular acceleration data is below a second threshold value; and
    generating information for diagnosing the sleep event of the subject based on the mandibular rotational data being above the first threshold value and the mandibular acceleration data being below the second threshold value.

2. The method of claim 1, wherein an oximeter, a thermistor, an audio sensor, an electromyography (EMG) unit, and/or a photoplethysmography (PPG) sensor are further disposed within the housing adhered to the exterior of the mandible of the subject.

3. The method of claim 1, wherein the sleep event corresponds to one of a normal event, an obstructive event, a central event, an arousal event, or a motor event.

4. The method of claim 1, further comprising applying the mandibular rotational data and the mandibular acceleration data to a machine learning model to determine a presence of the sleep event, the machine learning model trained to output likelihoods of a presence of a set of plurality of sleep events based on the mandibular rotational data and the mandibular acceleration data.

5. The method of claim 4, further comprising applying the mandibular rotational data and the mandibular acceleration data to a second machine learning model to determine a presence of a sleep stage corresponding to the time period.

6. The method of claim 5, wherein the sleep stage is one of awake, light sleep, deep sleep, or rapid eye movement (REM) sleep.

7. The method of claim 5, further comprising applying the sleep stage to the machine learning model to determine the presence of the sleep event.

8. The method of claim 5, further comprising receiving third data generated by a pulse oximeter worn by the subject and corresponding to the time period, the third data indicative of an oxygen level of the subject, wherein the information generated for diagnosing the sleep event of the subject is further based on the third data.

9. The method of claim 8, further comprising determining an absence of the sleep event based on the third data.

10. The method of claim 5, further comprising receiving third data generated by a thermistor positioned on the exterior of the mandible of the subject and corresponding to the time period, the third data indicative of an airflow generated by respiration of the subject, wherein the information generated for diagnosing the sleep event of the subject is further based on the third data.

11. The method of claim 10, further comprising determining an absence of the sleep event based on the third data.

12. The method of claim 1, further comprising generating a report indicating a presence of the sleep event of the subject at the time period.

13. The method of claim 1, wherein the mandibular rotational data above the first threshold value are indicative of a presence of rotation of the mandible of the subject.

14. The method of claim 1, wherein the mandibular acceleration data below the second threshold value are indicative of an absence of acceleration of a head of the subject.

15. A system for diagnosing a sleep event of a subject, the system comprising:
  memory configured to store computer-executable instructions; and
  at least one computer processor configured to access memory and execute the computer-executable instructions to:
    receive mandibular rotational data generated by a gyroscope mounted on an exterior of a mandible of the subject, the mandibular rotational data corresponding to a time period during sleep and indicative of rotational movement of the mandible of the subject;
    receive mandibular acceleration data generated by an accelerometer mounted on the exterior of the mandible of the subject, the mandibular acceleration data corresponding to the time period during the sleep and indicative of acceleration of the mandible of the subject, wherein the gyroscope and the accelerometer are disposed within a housing adhered to the exterior of the mandible of the subject;
    determine the mandibular rotational data is above a first threshold value;
    determine the mandibular acceleration data is below a second threshold value; and
    generate information for diagnosing the sleep event of the subject based on the mandibular rotational data being above the first threshold value and the mandibular acceleration data being below the second threshold value.

16. The system of claim 15, wherein an oximeter, a thermistor, an audio sensor, an electromyography (EMG) unit, and/or a photoplethysmography (PPG) sensor are further disposed within the housing adhered to the exterior of the mandible of the subject.

17. The system of claim 15, wherein the sleep event corresponds to one of a normal event, an obstructive event, a central event, an arousal event, or a motor event.

18. The system of claim 15, wherein the computer processor is further configured to execute the computer-executable instructions to apply the mandibular rotational data and the mandibular acceleration data to a machine learning model to determine a presence of the sleep event, the machine learning model trained to output likelihoods of a presence of a set of plurality of sleep events based on the mandibular rotational data and the mandibular acceleration data.

19. The system of claim 18, wherein the computer processor is further configured to execute the computer-executable instructions to apply the mandibular rotational data and the mandibular acceleration data to a second machine learning model to determine a presence of a sleep stage corresponding to the time period.

20. The system of claim 19, wherein the sleep stage is one of awake, light sleep, deep sleep, or rapid eye movement (REM) sleep.

21. The system of claim 19, wherein the computer processor is further configured to execute the computer-executable instructions to apply the sleep stage to the machine learning model to determine the presence of the sleep event.

22. The system of claim 19, wherein the computer processor is further configured to execute the computer-executable instructions to receive third data generated by a pulse oximeter worn by the subject and corresponding to the time period, the third data indicative of an oxygen level of the subject, wherein the information generated for diagnosing the sleep event is further based on the third data.

23. The system of claim 22, wherein the computer processor is further configured to execute the computer-executable instructions to determine an absence of the sleep event based on the third data.

24. The system of claim 19, wherein the computer processor is further configured to execute the computer-executable instructions to receive third data generated by a thermistor positioned on the exterior of the mandible of the subject and corresponding to the time period, the third data indicative an airflow generated by respiration of the subject, wherein the information generated for diagnosing the sleep event of the subject is further based on the third data.

25. The system of claim 24, wherein the computer processor is further configured to execute the computer-executable instructions to determine an absence of the sleep event based on the third data.

26. The system of claim 15, wherein the computer processor is further configured to execute the computer-executable instructions to generate a report indicating the presence of the sleep event of the subject at the time period.

27. The system of claim 15, wherein the mandibular rotational data above the first threshold value are indicative of a presence of rotation of the mandible of the subject.

28. The system of claim 15, wherein the mandibular acceleration data below the second threshold value are indicative of an absence of acceleration of a head of the subject.

29. The system of claim 15, wherein the sleep event is sleep apnea and the system is configured to generate the information for diagnosing the sleep apnea of the subject.

30. The method of claim 1, wherein the sleep event is sleep apnea and generating the information comprises generating the information for diagnosing the sleep apnea of the subject.

* * * * *